(12) United States Patent
Chalana et al.

(10) Patent No.: US 7,611,466 B2
(45) Date of Patent: Nov. 3, 2009

(54) ULTRASOUND SYSTEM AND METHOD FOR MEASURING BLADDER WALL THICKNESS AND MASS

(75) Inventors: Vikram Chalana, Mill Creek, WA (US); Stephen Dudycha, Bothell, WA (US); Gerald McMorrow, Kirkland, WA (US); Jongtae Yuk, Redmond, WA (US); Tim Shelton, North Bend, WA (US); Bill Barnard, Woodinville, WA (US)

(73) Assignee: Verathon Inc., Bothell, WA (US)

( * ) Notice: Subject to any disclaimer, the term of this patent is extended or adjusted under 35 U.S.C. 154(b) by 789 days.

(21) Appl. No.: 11/061,867

(22) Filed: Feb. 17, 2005

(65) Prior Publication Data
US 2005/0228278 A1    Oct. 13, 2005

Related U.S. Application Data

(63) Continuation-in-part of application No. 11/064,114, filed on Feb. 17, 2005, and a continuation-in-part of application No. 11/010,539, filed on Dec. 13, 2004, and a continuation-in-part of application No. 10/704,996, filed on Nov. 10, 2003, which is a continuation-in-part of application No. 10/701,955, filed on Nov. 5, 2003, now Pat. No. 7,087,022, which is a continuation-in-part of application No. 10/633,186, filed on Jul. 31, 2003, now Pat. No. 7,004,904, which is a continuation-in-part of application No. 10/443,126, filed on May 20, 2003, application No. 11/061,867, which is a continuation-in-part of application No. PCT/US03/24368, filed on Aug. 1, 2003, and a continuation-in-part of application No. 10/165,556, filed on Jun. 7, 2002, now Pat. No. 6,676,605, application No. 11/061,867, which is a continuation-in-part of application No. PCT/US03/14785, filed on May 9, 2003, which is a continuation-in-part of application No. 10/165,556, application No. 11/061,867, which is a continuation-in-part of application No. 10/633,186, which is a continuation-in-part of application No. 10/443,126.

(60) Provisional application No. 60/566,823, filed on Apr. 30, 2004, provisional application No. 60/566,818, filed on Apr. 30, 2004, provisional application No. 60/545,576, filed on Feb. 17, 2004, provisional application No. 60/423,881, filed on Nov. 5, 2002, provisional application No. 60/400,624, filed on Aug. 2, 2002, provisional application No. 60/470,525, filed on May 12, 2003.

(51) Int. Cl.
*A61B 8/00* (2006.01)

(52) U.S. Cl. .................. 600/443; 600/448; 600/449; 600/437; 382/128

(58) Field of Classification Search ............... 600/443, 600/448; 382/128, 254, 266, 274
See application file for complete search history.

(56) References Cited

U.S. PATENT DOCUMENTS 5,235,985 A    8/1993    McMorrow et al.

(Continued)

OTHER PUBLICATIONS

Kojima et al. Ultrasonic estimation of bladder weight as a measure of bladder hypertrophy in men with infravesical obstruction: a preliminary report. Urology. 47(6):942-947. 1996.*

(Continued)

*Primary Examiner*—Brian Casler
*Assistant Examiner*—Parikha S Mehta
(74) *Attorney, Agent, or Firm*—Black Lowe & Graham PLLC

(57) ABSTRACT

An ultrasound transceiver scans an organ and processes the echogenic signals to produce three-dimensional, two-dimensional, and one-dimensional information of the organ. The 3-D, 2-D, and 1-D information is utilized to determine the thickness, surface area, volume, and mass of the organ wall.

8 Claims, 64 Drawing Sheets

U.S. PATENT DOCUMENTS

| | | | |
|---|---|---|---|
| 5,698,549 | A | 12/1997 | Steers et al. |
| 5,841,889 | A * | 11/1998 | Seyed-Bolorforosh ...... 382/128 |
| 5,908,390 | A | 6/1999 | Matsushima |
| 5,964,710 | A | 10/1999 | Ganguly et al. |
| 6,110,111 | A * | 8/2000 | Barnard ...................... 600/438 |
| 6,213,949 | B1 | 4/2001 | Ganguly et al. |
| 6,443,894 | B1 | 9/2002 | Sumanaweera et al. |
| 6,511,426 | B1 | 1/2003 | Hossack et al. |
| 6,676,605 | B2 | 1/2004 | Barnard et al. |
| 6,755,787 | B2 | 6/2004 | Hossack et al. |

OTHER PUBLICATIONS

Naya et al., Intraobserver and Interobserver Variance in the Measurment of Ultrasound-Estimated Bladder Weight, Dept. Of Urology, Kyoto Prefectural University of Medicine, Ultrasound in Med & Biol, vol. 24, No. 5, pp. 771-773 (1998).

Kuzmic, Brkljacic & Ivankovic, Sonographic Measurement of Detrusor Muscle Thickness in Healthy Children, Pediatr Nephrol (2001) 16:1122-1125.

Muller, Jacobsson, Marild & Hellstrom, Detrusor Thickness in Healthy Children Assessed by a Standardized Ultrasound Method, The Journal of Uriology vol. 166, 2364-2367, Dec. 2001.

Muller et al., Standardized Ultrasound Method for Assessing Detrusor Muscle Thickness in Children, The Journal of Uriology, vol. 164, 134-138, Jul. 2000.

Kuzmic et al., Ultrasound Assessment of Detrusor Muscle Thickness in Children with Non-neuropathic Bladder/Sphincter Dysfunction, European Urology 41, 214-219 (2002).

Kojima et al., Ultrasonic Estimation of Bladder Weight as a Measure of Bladder Hypertrophy in Men with Infravesical Obstruction: A Priliminary Report, Dept. of Urology, Kyoto, Urology 47(6), 942-947 (1996).

Kojima et al, Reversible Change of Bladder Hypertrophy due to Benign Prostatic Hyperplasia After Surgical Relief of Obstruction, Journal of Urology, vol. 158, 89-93, Jul. 1997.

Manieri et al., The Diagnosis of Bladder Outlet Obstruction in Men by Ultrasound Measurement of Bladder Wall Thickness, The Journal of Urology, vol. 159, 761-765, Mar. 1998.

Miyashita et al., Ultrasonic Measurement of Bladder Weight as a Possible Predictor of Acute Urinary Retention in Men with Lower Urinary Tract Symptoms Suggestive of Benign Prostatic Hyperplana, Ultrasound in Med & Biol, vol. 28, No. 8, pp. 985-990 (2002).

Oelke, Hofner, Wiese, Grunewald & Jonas, Increase in Detrusor Wall Thickness Indicates Bladder Outlet Obstruction (BOO) in Men, World J Urol (2002) 19: 443-452.

* cited by examiner

| ClonedExams | 820 |
|---|---|
| PK | iOriginalExamID |
| | iNewExamID |
| | iUserID |
| | siOriginalResultCode |
| | dtTimeStamp |

ULTRASOUND SYSTEM AND METHOD FOR MEASURING BLADDER WALL THICKNESS AND MASS

PRIORITY CLAIM

This application claims priority to U.S. Provisional Patent Application Ser. No. 60/566,823, filed Apr. 30, 2004; to U.S. Provisional Patent Application Ser. No. 60/566,818, filed Apr. 30, 2004; and to U.S. Provisional Patent Application Ser. No. 60/545,576, filed Feb. 17, 2004. This application also claims priority to and is a continuation-in-part of U.S. patent application Ser. No. 11/064,114 filed Feb. 17, 2005.

This application is also a continuation-in-part of and claims priority to U.S. application Ser. No. 11/010,539 filed Dec. 13, 2004, which claims priority to PCT/EP03/07807 filed Jul. 17, 2003, which is also a continuation of and claims priority to UK Application Serial No. 0218547.8 filed Aug. 9, 2002; and a continuation-in-part of and claims priority to U.S. patent application Ser. No. 10/704,996, filed Feb. 3, 2005, which is a continuation-in-part of and claims priority to PCT/EP03/07807 filed Jul. 17, 2003, which also is a continuation-in-part of and claims priority to UK Application Serial No. 0218547.8 filed Aug. 9, 2002.

This application is also a continuation-in-part of and claims priority to U.S. patent application Ser. No. 10/704,996, filed Nov. 10, 2003, which claims priority to, and is a continuation-in-part of U.S. patent application Ser. No. 10/701,955 filed Nov. 5, 2003, now U.S. Pat. No. 7,087,022, which also is a continuation-in-part and claims priority to U.S. patent application Ser. No. 10/633,186, filed Jul. 31, 2003, now U.S. Pat. No. 7,004,904, which claims priority to and is a continuation-in-part of U.S. patent application Ser. No. 10/443,126 filed May 20, 2003, which claims priority to U.S. Provisional Patent Application Ser. No. 60/423,881, filed Nov. 5, 2002 and to U.S. Provisional Patent Application Ser. No. 60/400,624, filed Aug. 2, 2002.

This application is also a continuation-in-part of, and claims priority to U.S. patent application Ser. No. 10/165,556, filed Jun. 7, 2002 now U.S. Pat. No. 6,676,605.

This application is also a continuation-in-part of, and claims priority to Patent Cooperation Treaty (PCT) Application Serial Number PCT/US03/24368, filed Aug. 1, 2003, which claims priority to U.S. Provisional Patent Application Ser. No. 60/423,881, filed Nov. 5, 2002, and U.S. Provisional Patent Application Ser. No. 60/400,624, filed Aug. 2, 2002.

This application is also a continuation-in-part of, and claims priority to Patent Cooperation Treaty (PCT) Application Serial No. PCT/US03/14785, filed May 9, 2003, which is a continuation of U.S. patent application Ser. No. 10/165,556, filed Jun. 7, 2002.

This application is also a continuation-in-part of, and claims priority to U.S. patent application Ser. No. 10/633,186, which claims priority to U.S. Provisional Patent Application Ser. No. 60/423,881, filed Nov. 5, 2002, and U.S. Provisional Patent Application Ser. No. 60/400,624, filed Aug. 2, 2002, and is a continuation-in-part of and claims priority to U.S. patent application Ser. No. 10/443,126, filed May 20, 2003, which claims priority to U.S. Provisional Patent Application Ser. No. 60/423,881, filed Nov. 5, 2002, and to U.S. Provisional Patent Application No. 60/400,624, filed Aug. 2, 2002.

This application also claims priority to U.S. Provisional Patent Application Ser. No. 60/470,525, filed May 12, 2003, and also claims priority to and is a continuation-in-part of U.S. patent application Ser. No. 10/165,556, filed Jun. 7, 2002. All of the foregoing applications are incorporated by reference in their entirety, as if fully set forth herein.

FIELD OF THE INVENTION

This invention relates generally to ultrasound imaging systems and methods, and more particularly, to ultrasound systems and methods used in diagnosing various disease states.

BACKGROUND OF THE INVENTION

A variety of ultrasound methods may be used to evaluate a bladder dysfunction. In general, such methods estimate a bladder volume containing an amount of urine. For example, U.S. Pat. No. 6,110,111 to Barnard discloses an ultrasound system for estimating bladder pressure by comparing the estimated bladder surface area with the surface area of a comparable sphere. According to Barnard, as the bladder surface area approaches the surface area of the comparable sphere, a greater pressure within the bladder is inferred.

Other bladder measurements are possible using ultrasound methods, and are similarly useful in the diagnosis of several different bladder conditions. For example, a bladder wall thickness and bladder mass may be estimated using ultrasound, and may be used to indicate a bladder outlet obstruction and/or a bladder distension. In general, a bladder outlet obstruction results in an elevated internal pressure in the bladder that must be overcome by the surrounding muscle as the bladder contracts during urination. Accordingly, an undesired hypertrophy of the bladder muscle often results. Symptoms of bladder muscle hypertrophy generally include increased bladder wall thickness and increased bladder wall mass. See, for example, P. N. Matthews, J. B. Quayle, A. E. A. Joseph, J. E. Williams, K. W. Wilkinson and P. R. Riddle; "The Use of Ultrasound din the Investigation of Prostatism", *British Journal of Urology*, 54:536-538, 1982; and C. J. Cascione, F. F. Bartone and M. B. Hussain; "Transabdominal Ultrasound Versus Excretory Urography in Preoperative Evaluation of Patients with Prostatism", *Journal of Urology*, 137:883-885, 1987). Using an estimated bladder wall thickness to infer a bladder wall volume, or, alternately, a bladder wall mass (obtained by multiplying the estimated bladder wall volume by a specific gravity of the bladder tissue) yields a value that is generally independent of the bladder volume. While the bladder wall thins as the volume increases, the total bladder wall volume (or the bladder wall mass) remains generally unchanged.

Another indicator of the bladder condition is bladder distension. As the bladder volume increases in response to increased internal bladder pressure, the bladder walls elongate and decrease in thickness, resulting in the distention. Bladder distention is generally associated with numerous bladder ailments, including incontinence and hyperdistension. Incontinence occurs when sphincter muscles associated with the bladder are unable to retain urine within the bladder as the bladder pressure and bladder distension increases. In many individuals, incontinence occurs when the bladder volume achieves a consistent maximum volume in the individual. Consequently, if the maximum volume is known, and if the bladder volume can be measured while the volume is approaching the maximum value, incontinence may be prevented. When hyperdistension occurs, the bladder fills with an excessive amount urine and generates an internal bladder pressure that may cause serious adverse effects, including renal damage, renal failure, or even death of the patient from autonomic dysreflexia if the patient has spinal cord damage.

It is further observed that normal bladder response is relatively constant at small bladder volumes in typical adult humans. Accordingly, normal healthy adults encounter little physical difficulty voiding, and typically leave less than about 50 milliliters (ml) of urine in the bladder. Thus at the present time, it is relatively easy to distinguish a normal post-void-residual (PVR) volume from an abnormal PVR volume that may be indicative of a potential medical problem. At low bladder volumes, bladder distension information is not typically useful since normal humans have widely varying bladder capacities. Thus, it is more difficult to establish a volume threshold at which over-distension occurs or when incontinence occurs for a selected individual. Consequently, as the bladder fills, measurement of bladder distension becomes more useful as an indicator of hyperdistension and bladder capacity in an individual.

Current ultrasound methods measure bladder wall thicknesses using one-dimensional (A-mode) and two-dimensional (B-mode) ultrasound modes. Unfortunately, the application of these current methods to determine bladder wall thickness are susceptible to operator error, are time consuming, and generally lead to inaccurate estimations of the bladder wall thickness. For example, in one known ultrasound method, an operator applies an ultrasound probe to an external portion of the patient and projects ultrasound energy into the patient to image a bladder region. Since the operator must repeatedly reposition the ultrasound probe until a bladder wall image is sufficiently visible, inaccuracies may be introduced into the ultrasound data. Consequently, current ultrasound methods to determine bladder wall thickness is an unreliable or ineffective means to measure bladder distension.

Thus, there is a need for an ultrasound method and system that permits a bladder wall thickness to be accurately measured.

SUMMARY OF THE INVENTION

Systems and methods for ultrasound imaging an abdominal region in a patient to detect and measure underlying organ structures, and in particular, to image a bladder to determine the thickness, volume and mass of the bladder detrussor are disclosed. In an aspect of the invention, echogenic data is obtained by scanning the abdominal region to obtain a three-dimensional scancone assembly comprised of two-dimensional scanplanes, or an array of three-dimensional distributed scanlines. Selected two-dimensional and one-dimensional algorithms are then applied to the echogenic data to measure the bladder wall thickness and surface area.

The pixel location of initial wall loci are determined in two-dimensional scanplanes via B-mode echo signal processing algorithms applied to scanlines crossing the organ wall. The pixel location of the initial wall loci serve as an initial approximation of wall location from which more exacting algorithms are applied to either reconfirm the initially selected wall loci, or more likely, to select other loci positions. The reconfirmed or newly selected loci positions are achieved by the application of higher resolving, echo signal processing algorithms to define final wall loci pixel locations. Thereafter, verification of the final wall loci pixel locations are established by cost function analysis using neighboring final pixel locations of scanlines within the same scanplane.

The final wall pixel loci as determined include the organ outer-wall and the organ inner-wall pixel locations. The distance separating the organ outer-wall and inner-wall final pixel loci determines the thickness of the organ wall. B-mode algorithms applied to the final outer-wall loci pixel locations, as determined by the A-mode algorithms, determine the outer boundary of the organ wall within a given scanplane. Surface area of the inner-wall boundary is determined by analysis of the scanplane arrays within the scancone. Organ wall volume is calculated as a product of organ wall surface area and thickness. Organ wall mass is determined as a product of organ wall volume and density. When the organ is a bladder, the bladder wall thickness and wall mass is calculated to provide information to assess bladder dysfunction.

The collection of two-dimensional and one-dimensional algorithms includes ultrasound B-mode based segmentation and specialized snake algorithms to determine the surface area of the organ wall and to provide an initial front wall location. The initial front wall location determined by the B-mode algorithms is sufficiently precise to be further processed by the one-dimensional algorithms. The one-dimensional algorithms are unique sequences of A-mode based algorithms applied to the echogenic ultrasound scanlines to further improve the accuracy and precision of wall location loci as initially determined by the B-mode algorithms. The one-dimensional A-mode based algorithms provide for adjusting the position of the wall loci by applying a one-dimensional analysis of the pulse echoes associated with the two-dimensional image to a second position and a third position.

In accordance with the preferred embodiment of the invention, a microprocessor-based ultrasound apparatus, placed on the exterior of a patient, scans the bladder of the patient in multiple planes with ultrasound pulses, receives reflected echoes along each plane, transforms the echoes to analog signals, converts the analog signals to digital signals, and downloads the digital signals to a computer system.

Although a variety of scanning and analysis methods may be suitable in accordance with this invention, in a preferred embodiment the computer system performs scan conversion on the downloaded digital signals to obtain a three-dimensional, conically shaped image of a portion of the bladder from mathematical analysis of echoes reflecting from the inner (submucosal) and outer (subserosal) surfaces of the bladder wall. The conical image is obtained via ultrasound pulse echoing using radio frequency (RF) ultrasound (approximately 2-10 MHz) to obtain a three-dimensional array of two-dimensional scanplanes, such that the scanplanes may be a regularly spaced array, an irregular spaced array, or a combination of a regularly spaced array and irregularly spaced array of two-dimensional scanplanes. The two-dimensional scanplanes, in turn are formed by an array of one-dimensional scanlines (ultrasound A-lines), such that the scanlines may be regularly spaced, irregularly spaced, or a combination of regularly spaced and irregularly spaced scanlines. The three-dimensional array of two-dimensional scanplanes results in a solid angle scan cone.

Alternatively, a solid angle scan cone is obtained by three-dimensional data sets acquired from a three-dimensional ultrasound device configured to scan a bladder in a three-dimensional scan cone of three-dimensional distributed scanlines. The three-dimensional scan cone is not a three-dimensional array of two-dimensional scanplanes, but instead is a solid angle scan cone formed by a plurality of internal and peripheral one-dimensional scanlines. The scanlines are ultrasound A-lines that are not necessarily confined within a scanplane, but would otherwise occupy the inter-scanplane spaces that are in the three-dimensional array of two-dimensional scanplanes.

The solid angle scan cones, either as a three-dimensional array of two-dimensional scanplanes, or as a three-dimensional scan cone of three-dimensional distributed scanlines, provides the basis to locate bladder wall regions or surface patches of the inner and outer surfaces of the bladder wall. The location of each surface patch is determined and the distance or thickness between the inner and outer surface patches is measured. The bladder wall mass is calculated as a product of the surface area of the bladder, the bladder wall thickness, and the specific gravity of the bladder wall. The entire bladder wall or various regions, including anterior, posterior, and lateral portions of the bladder, may be measured for thickness and mass. Preferred embodiments of the programs to analyze scanline or scanplane data to determine bladder thickness and mass employ algorithms.

An alternate embodiment of the invention configures the downloaded digital signals to be compatible with a remote microprocessor apparatus controlled by an Internet web-based system. The Internet web-based system has multiple programs that collect, analyze, and store organ thickness and organ mass determinations. The alternate embodiment can measure the rate at which internal organs undergo hypertrophy over time. The programs can include instructions to permit disease tracking, disease progression, and provide educational instructions to patients.

BRIEF DESCRIPTION OF THE DRAWINGS

The preferred and alternative embodiments of the present invention are described in detail below with reference to the following drawings:

FIG. 53 is a screen shot of Exam Quality Report;

DETAILED DESCRIPTION OF THE PREFERRED EMBODIMENT

Figure 1:
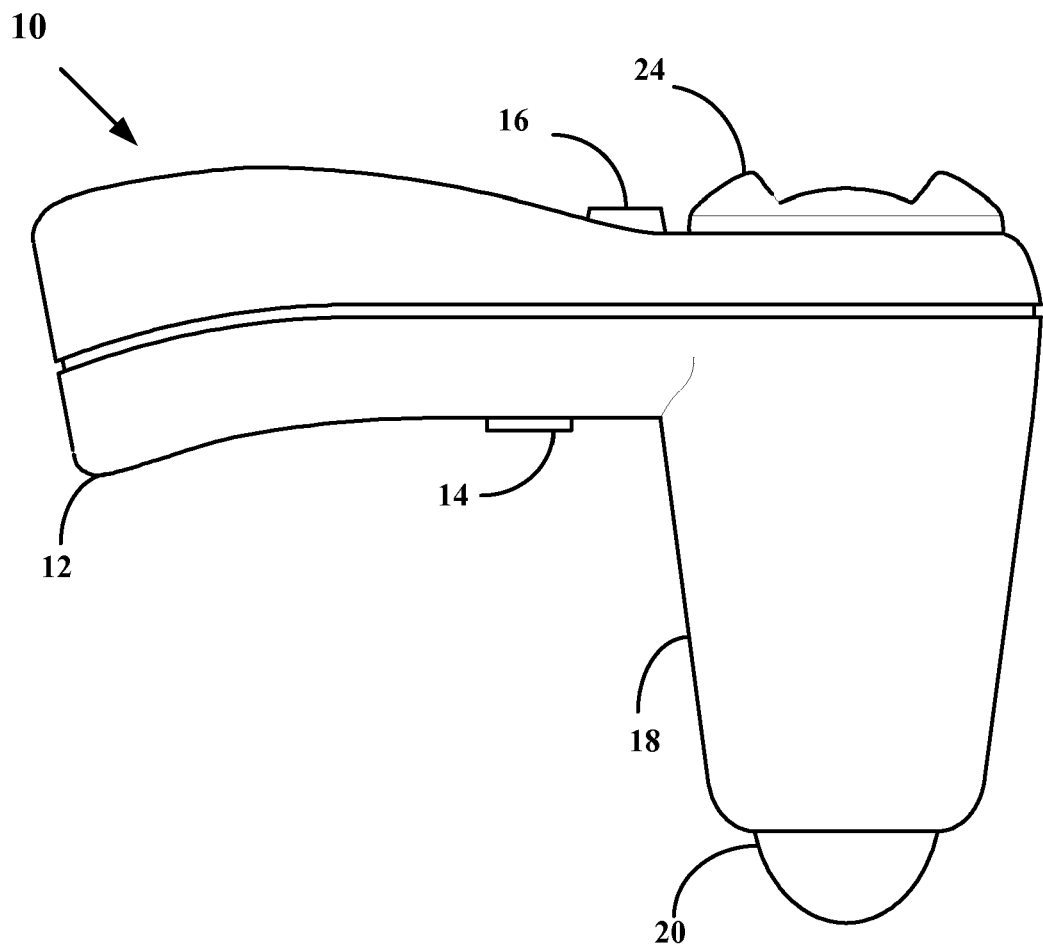
FIG. 1 is a side elevational view of an ultrasound transceiver according to an embodiment of the invention.

FIG. 1 is a side elevational view of an ultrasound transceiver 10. Transceiver 10 includes a transceiver housing 18 having an outwardly extending handle 12 suitably configured to allow a user to manipulate transceiver 10. The handle 12 includes a trigger 14 that allows the user to initiate an ultrasound scan of a selected anatomical portion, and a cavity selector 16, described below. Transceiver 10 includes a transceiver dome 20 that contacts a surface portion of the patient when the selected anatomical portion is scanned to provide an appropriate acoustical impedance match and to properly focus ultrasound energy as it is projected into the anatomical portion. The transceiver 10 further includes an array of separately excitable ultrasound transducer elements (not shown in FIG. 1) positioned within the housing 18. The transducer elements are suitably positioned within the housing 18 to project ultrasound energy outwardly from the dome 20, and to permit reception of acoustic reflections generated by internal structures within the anatomical portion. The array of ultrasound elements may include a one-dimensional, or a two-dimensional array of piezoelectric elements that are moved within the housing 18 by a motor, of a transceiver dome 20 that contacts a surface portion of the patient when the selected anatomical portion is scanned, or other similar actuation means to scan the selected anatomical region. Alternately, the array may be stationary with respect to the housing 18 so that the selected anatomical region is scanned by selectively energizing the elements in the array. Transceiver 10 includes a display 24 operable to view processed results from the ultrasound scan, and to allow operational interaction between the user and the transceiver 10. Display 24 may be configured to display alphanumeric data that indicates a proper and/or optimal position of the transceiver 10 relative to the selected anatomical portion. In other embodiments, two- or three-dimensional images of the selected anatomical region may be displayed on the display 24. The display 24 may be a liquid crystal display (LCD), a light emitting diode (LED) display, a cathode ray tube (CRT) display, or other suitable display devices operable to present alphanumeric data and/or graphical images to a user.

Still referring to FIG. 1, the cavity selector 16 is structured to adjustably control the transmission and reception of ultrasound signals to the anatomy of a patient. In particular, the cavity selector 16 adapts the transceiver 10 to accommodate various anatomical details of male and female patients. For example, when the cavity selector 16 is adjusted to accommodate a male patient, the transceiver 10 is suitably configured to locate a single cavity, such as a urinary bladder in the male patient. In contrast, when the cavity selector 16 is adjusted to accommodate a female patient, the transceiver 10 is configured to image an anatomical portion having multiple cavities, such as a bodily region that includes a bladder and a uterus. Alternate embodiments of the transceiver 10 may include a cavity selector 16 configured to select a single cavity scanning mode, or a multiple cavity-scanning mode that may be used with male and/or female patients. The cavity selector 16 may thus permit a single cavity region to be imaged, or a multiple cavity region, such as a region that includes a lung and a heart to be imaged.

To scan a selected anatomical portion of a patient, the transceiver dome 20 of the transceiver 10 is positioned against a surface portion of a patient that is proximate to the anatomical portion to be scanned. The user then actuates the transceiver 10 by depressing trigger 14. In response, transceiver 10 transmits ultrasound signals into the body, and receives corresponding return echo signals that are at least partially processed by the transceiver 10 to generate an ultrasound image of the selected anatomical portion. In a particular embodiment, the transceiver 10 transmits ultrasound signals in a range that extends from approximately about two megahertz (MHz) to approximately about ten MHz.

In one embodiment, the transceiver 10 is operably coupled to an ultrasound system that is configured to generate ultrasound energy at a predetermined frequency and/or pulse repetition rate and to transfer the ultrasound energy to the transceiver 10. The system also includes a processor that is configured to process reflected ultrasound energy that is received by the transceiver 10 to produce an image of the scanned anatomical region. Accordingly, the system generally includes a viewing device, such as a cathode ray tube (CRT), a liquid crystal display (LCD), a plasma display device, or other similar display devices, that may be used to view the generated image. The system may also include one or more peripheral devices that cooperatively assist the processor to control the operation of the transceiver 10, such a keyboard, a pointing device, or other similar devices. The ultrasound system will be described in greater detail below. In still another particular embodiment, the transceiver 10 may be a self-contained device that includes a microprocessor positioned within the housing 18 and software associated with the microprocessor to operably control the transceiver 10, and to process the reflected ultrasound energy to generate the ultrasound image. Accordingly, the display 24 is used to display the generated image and/or to view other information associated with the operation of the transceiver 10. For example, the information may include alphanumeric data that indicates a preferred position of the transceiver 10 prior to performing a series of scans. In yet another particular embodiment, the transceiver 10 may be operably coupled to a general-purpose computer, such as a laptop or a desktop computer that includes software that at least partially controls the operation of the transceiver 10, and also includes software to process information transferred from the transceiver 10, so that an image of the scanned anatomical region may be generated.

Although transceiver 10 of FIG. 1 may be used in any of the foregoing embodiments, other transceivers may also be used. For example, the transceiver may lack one or more features of the transceiver 10. For example, a suitable transceiver may not be a manually portable device, and/or may not have a top-mounted display, or may selectively lack other features or exhibit further differences.

Figure 2:
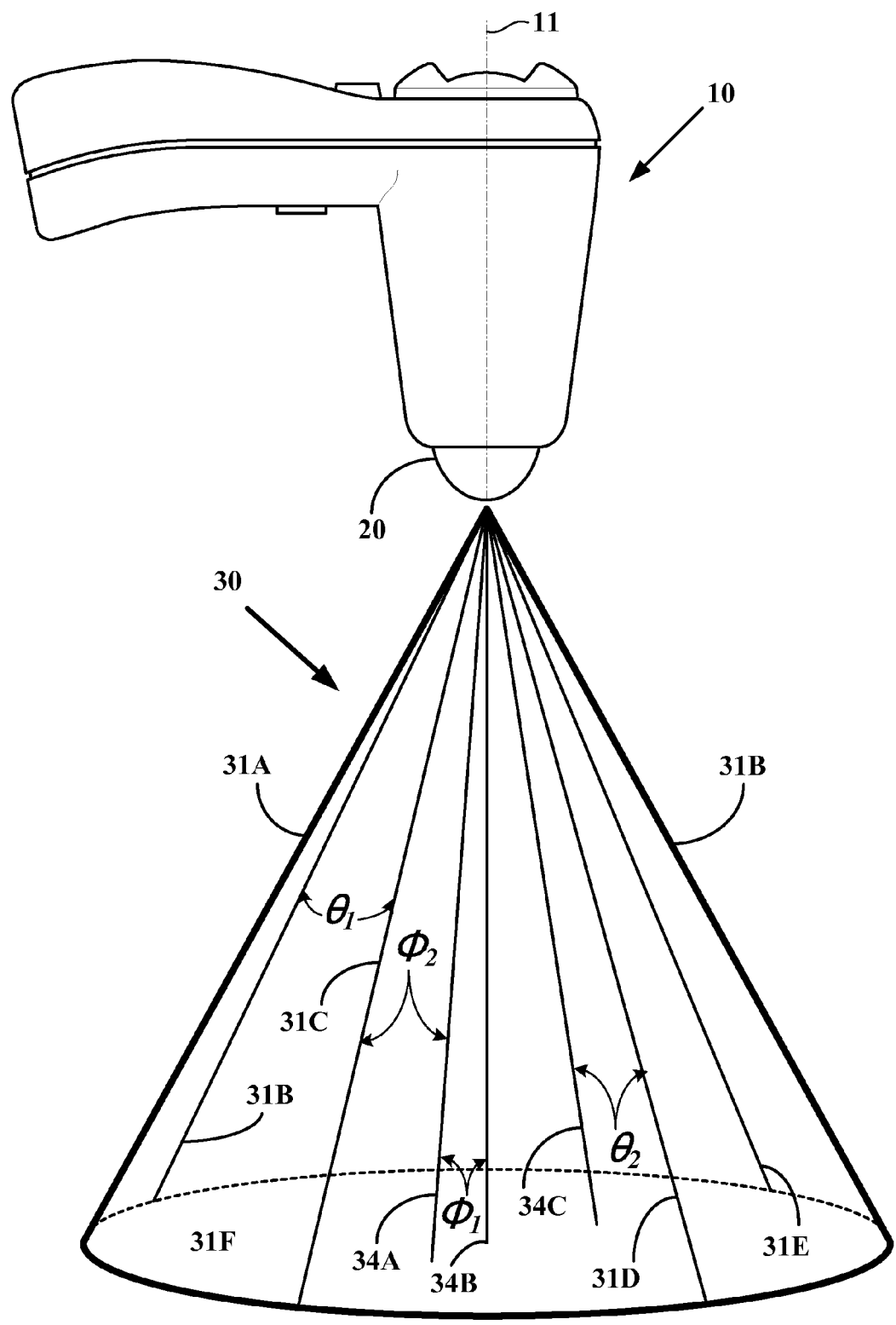
FIG. 2 is an isometric view of an ultrasound scancone that projects outwardly from the transceiver of FIG. 1.

FIG. 2 is an isometric view of an ultrasound scancone 30 that projects outwardly from the transceiver 10 of FIG. 1 that will be used to further describe the operation of the transceiver 10. The ultrasound scancone 30 extends outwardly from the dome 20 of the transceiver 10 and has a generally conical shape comprised of a plurality of discrete scanplanes having peripheral scanlines 31A-31F that define an outer surface of the scancone 30. The scanplanes also include internal scanlines 34A-34C that are distributed between the respective peripheral scanlines 31A-31F of each scanplane. The scanlines within each scanplane are one-dimensional ultrasound A-lines that taken as an aggregate define the conical shape of the scancone 30.

Figures 3A, 3B:
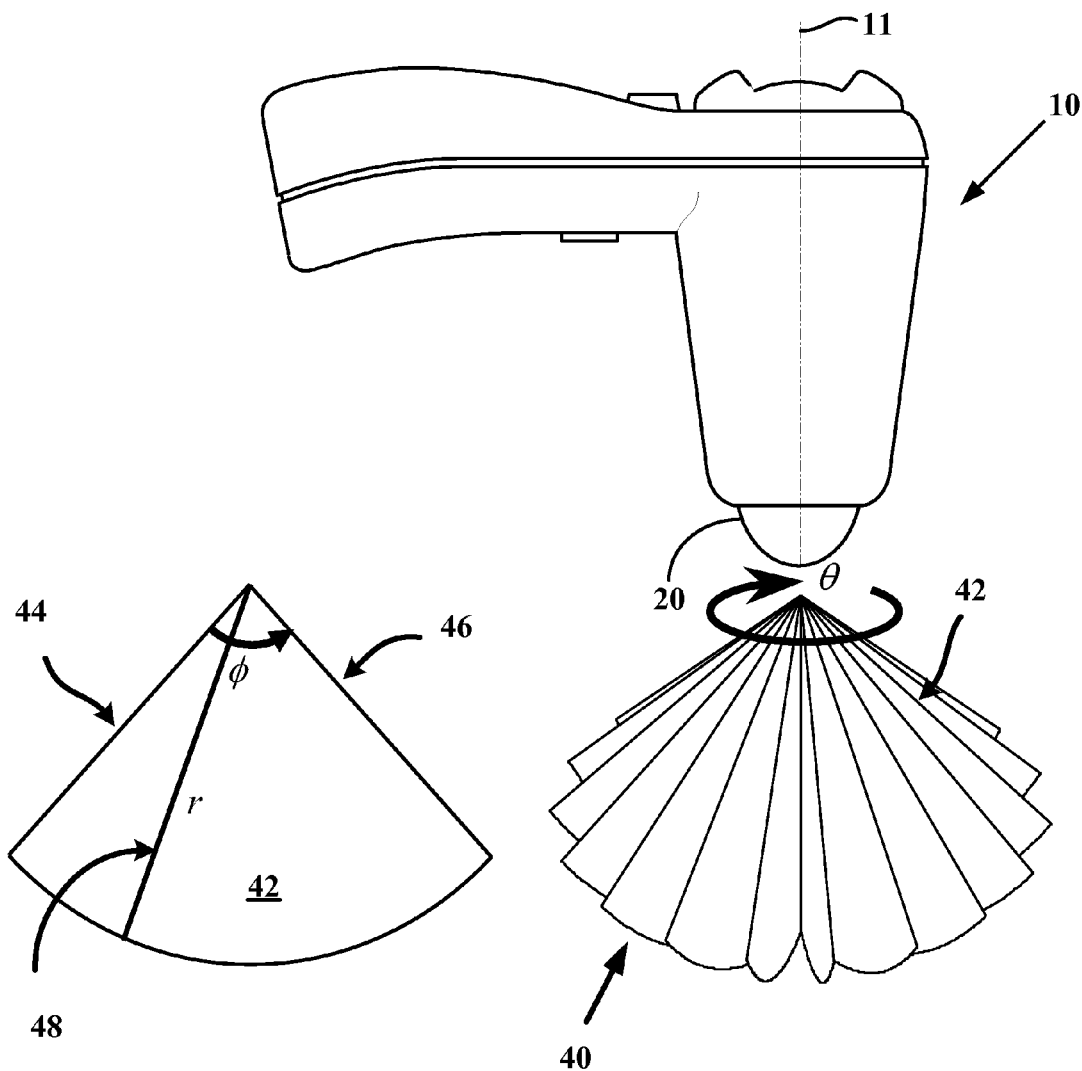
FIG. 3A is a plan view of an ultrasound scanplane representation of an ultrasound scancone that projects outwardly from the transceiver of FIG. 1.
FIG. 3B is an isometric view of an ultrasound scancone that projects outwardly from the transceiver of FIG. 1.

With reference still to FIG. 2 and now also to FIG. 3A, an ultrasound scancone 40 formed by a rotational array of two-dimensional scanplanes 42 projects outwardly from the dome 20 of the transceiver 10. The plurality of scanplanes 40 are oriented about an axis 11 extending through the transceiver 10. Each of the scanplanes 42 are positioned about the axis 11 at a predetermined angular position θ. The scanplanes 42 are mutually spaced apart by angles $\theta_1$ and $\theta_2$. Correspondingly, the scanlines within each of the scanplanes 42 are spaced apart by angles $\phi_1$ and $\phi_2$. Although the angles $\theta_1$ and $\theta_2$, are depicted as approximately equal, it is understood that the angles $\theta_1$ and $\theta_2$ may have different values. Similarly, although the angles $\phi_1$ and $\phi_2$ are shown as approximately equal, the angles $\phi_1$ and $\phi_2$ may also have different angles.

Referring now also to FIG. 3B, the peripheral scanlines 44 and 46, and an internal scanline 48 is further defined by a length r that extends outwardly from the transceiver 10 (FIG. 3A). Thus, a selected point P along the peripheral scanlines 44 and 46 and the internal scanline 48 may be defined with reference to the distance r and angular coordinate values $\phi$ and $\theta$.

With continued reference to FIGS. 2, 3A and 3B, the plurality of peripheral scanlines 31A-E and the plurality of internal scanlines 34A-D are three dimensional-distributed A-lines (scanlines) that are not necessarily confined within a scanplane, but instead may sweep throughout the internal regions and along the periphery of the scancone 30 (FIG. 2). Thus a given point P within the scancone 30 may be identified by the coordinates r, $\phi$, and $\theta$ whose values can vary. The number and location of the internal scanlines emanating from the transceiver 10 may thus be distributed within the scancone 30 at different positional coordinates as required to sufficiently visualize structures or images within the scancone 30. As described above, the angular movement of the transducer may be mechanically effected, or it may be electronically generated. In either case, the number of lines and the length of the lines may vary, so that the tilt angle $\phi$ sweeps through angles approximately between −60° and +60° for a total arc of approximately 120°. In one embodiment, the transceiver 10 is configured to generate a plurality of scanlines between the first limiting scanline 44 and the second limiting scanline 46 of approximately about seventy-seven, each having a length of approximately about 18 to 20 centimeters (cm).

As previously described, the angular separation between adjacent scanlines 34 (FIG. 2) may be uniform or non-uniform. For example, and in another particular embodiment, the angular separation $\phi_1$ and $\phi_2$ (as shown in FIG. 2) may be about 1.5°. Alternately, and in another particular embodiment, the angular separation $\phi_1$ and $\phi_2$ may be a sequence wherein adjacent angles are ordered to include angles of 1.5°, 6.8°, 15.5°, 7.2°, and so on, where a 1.5° separation is between a first scanline and a second scanline, a 6.8° separation is between the second scanline and a third scanline, a 15.5° separation is between the third scanline and a fourth scanline, a 7.2° separation is between the fourth scanline and a fifth scanline, and so on. The angular separation between adjacent scanlines may also be a combination of uniform and non-uniform angular spacings, for example, a sequence of angles may be ordered to include 1.5, 1.5, 1.5°, 7.2°, 14.3°, 20.2°, 8.0°, 8.0°, 8.0°, 4.3°, 7.8°, so on.

After a scanplane 42 is generated, the transceiver 10 rotates the transducer through a rotational angle θ (FIG. 3A) to position the transducer assembly within the transceiver 10 to a different angular increment, to generate another scanplane. As the transducer assembly is rotated in the direction θ, a series of scanplanes is generated, with each scanplane slightly rotated in relation to the prior scanplane by a selected increment of the rotational angle θ. As previously described, the increment between adjacent scanplanes may be uniform or no uniform. For example, and with reference still to FIG. 3B, in another particular embodiment, each scanplane 42 may be projected at an approximately 7.5° rotational angle increment. In other embodiments, the angular increment may be non-uniform and arranged in a sequence wherein the spacing between adjacent scanplanes includes 3.0°, 18.5°, 10.2°, and so on. Accordingly, an increment of approximately 3.0° is present between a first scanplane and a second scanplane, an increment of approximately 18.5° is present between the second scanplane and a third scanplane, and an increment of approximately 10.2° is present between the third scanplane and a fourth scanplane, and so on. The scanplane interval may also be a combination of uniform and non-uniform rotational angle increments, such as, for example, a sequence of incremental angles ordered in a sequence including 3.0°, 3.0°, 3.0°, 18.5°, 10.2°, 20.6°, 7.5°, 7.5°, 7.5°, 16.0°, 5.8° and so on.

Figure 3C:
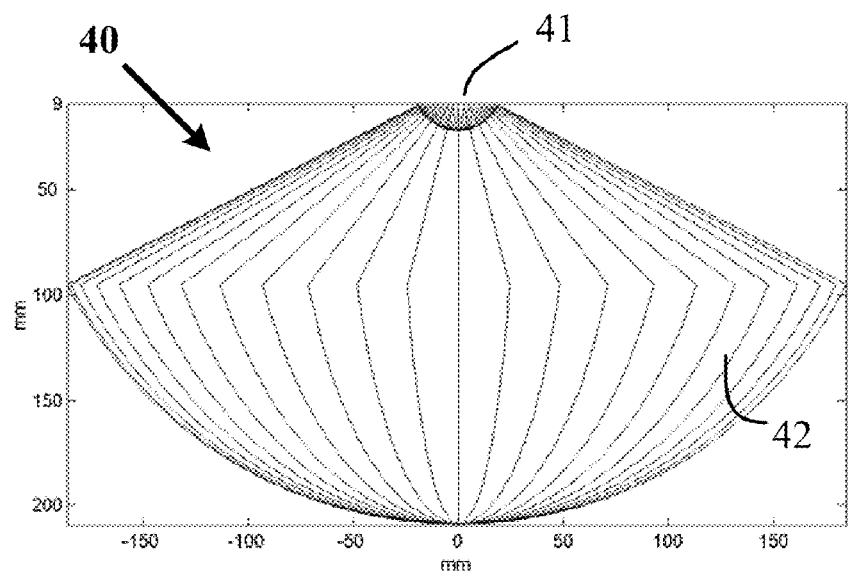
FIG. 3C is a scancone that is generated by the transceiver of FIG. 1.
Figure 3D:
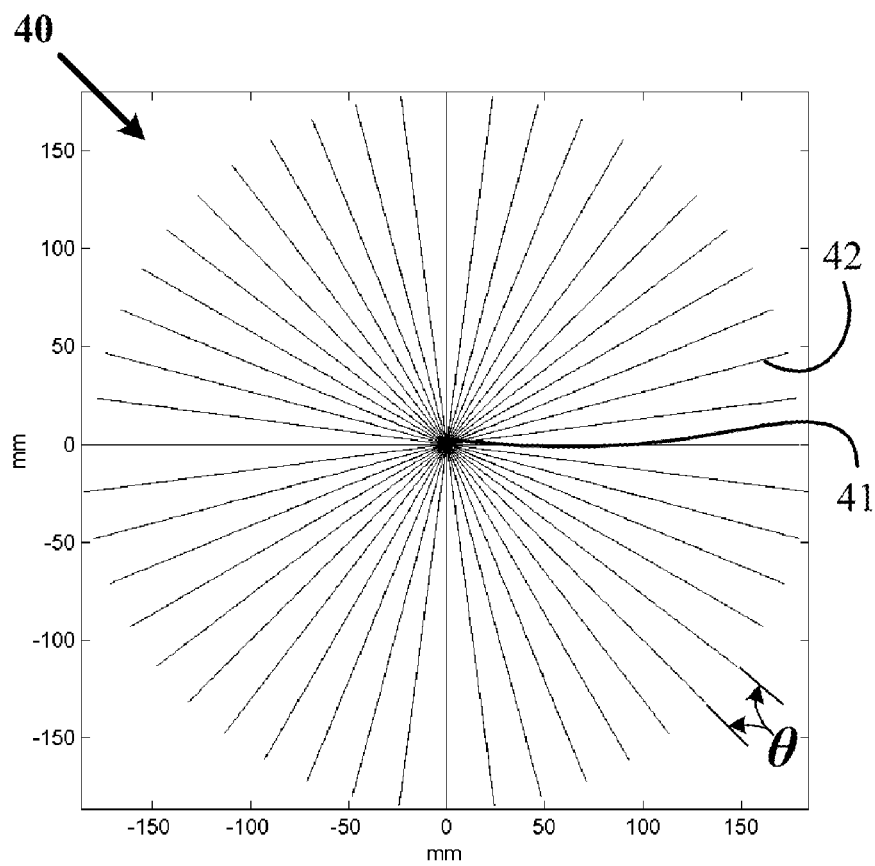
FIG. 3D is a plan view of the scancone of FIG. 3C.

FIG. 3C is a scancone 40 that is generated by the transceiver 10. The scancone 40 includes a dome cutout 41 near an apex of the scancone 40 that is formed, at least in part, to the presence of the transceiver dome 20 (as shown in FIG. 1). Referring now to FIG. 3D, a plan view of the scancone 40 of FIG. 3D is shown. The dome cutout 41 is positioned at an approximate center of the scancone 40, with each of the scanplanes 42 mutually spaced apart by the angular increment θ. Although the scancone 40 includes forty-eight scanplanes 42 that are mutually uniformly spaced apart, the number of scanplanes 42 in the scancone 40 may include at least two, but can be varied to include any desired number of scanplanes 42.

Figure 3E:
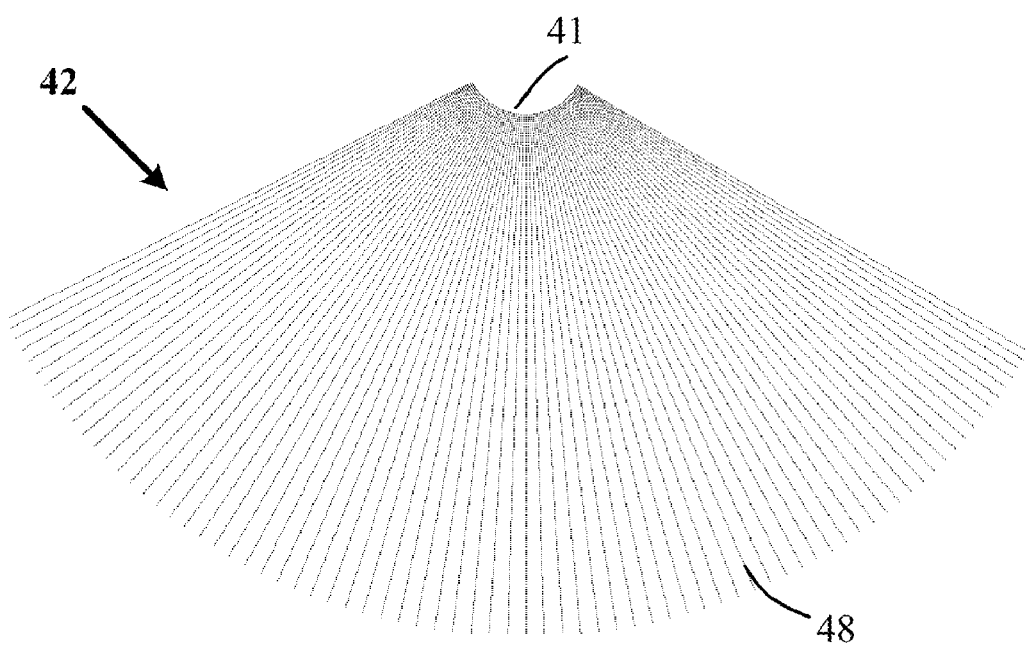
FIG. 3E is side-elevational view of the scanplane of FIG. 3C and FIG. 3D.

FIG. 3E is side-elevational view of the scanplane 42 of FIG. 3C and FIG. 3D that includes approximately about seventy-seven scanlines 48 that extend outwardly from the dome cutout 41. Other scancone configurations are possible. For example, a wedge-shaped scancone, or other similar shapes may be generated by the transceiver 10 (FIG. 1).

Figures 4A, 4B:
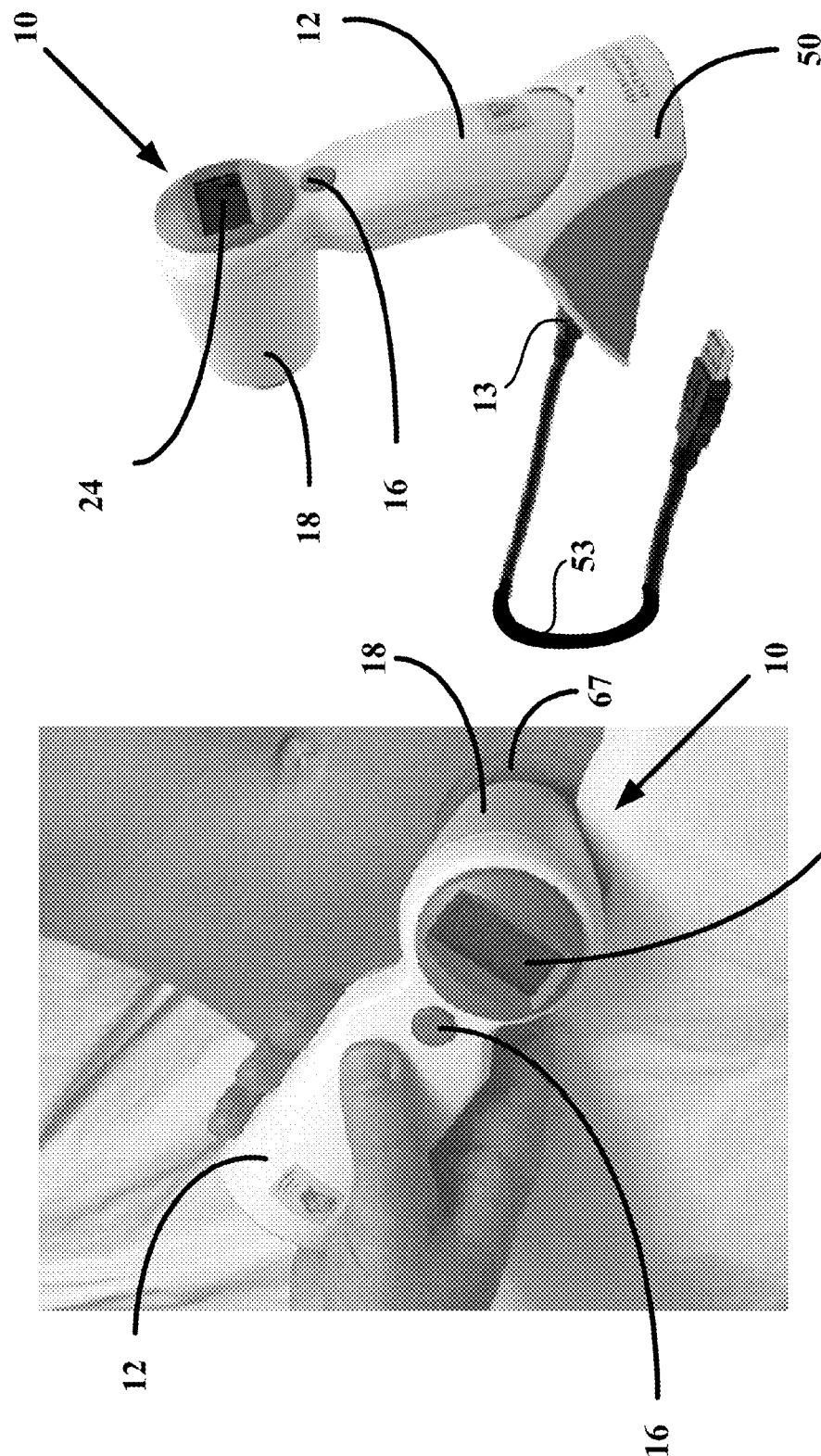
FIG. 4A is an isometric view of the transceiver of FIG. 1 applied to an abdominal region of a patient.
FIG. 4B is a perspective view of the transceiver of FIG. 1 positioned in a communication cradle according to another embodiment of the invention.

FIG. 4A is an isometric view of the transceiver 10 of FIG. 1 applied to an abdominal region of a patient, which is representative of a data acquisition method for a bladder wall mass determination in the patient. In contact with the patient is a pad 67 containing a sonic coupling gel to minimize ultrasound attenuation between the patient and the transceiver 10. Alternatively, sonic coupling gel may be applied to the patient's skin. The dome 20 (not shown) of the transceiver 10 contacts the pad 67. The transceiver 10 may the used to image the bladder trans-abdominally, and initially during a targeting phase, the transceiver 10 is operated in a two-dimensional continuous acquisition mode. In the two-dimensional continuous mode, data is continuously acquired and presented as a scanplane image as previously shown and described. The data thus acquired may be viewed on a display device, such as the display 24, coupled to the transceiver 10 while an operator physically translates the transceiver 10 across the abdominal region of the patient. When it is desired to acquire data, the operator may acquire data by depressing the trigger 14 of the transceiver 10 to acquire real-time imaging that is presented to the operator on the display device.

FIG. 4B is a perspective view of the transceiver 10 of FIG. 1 positioned in a communication cradle 50 according to another embodiment of the invention. The communication cradle 50 is operable to receive the transceiver 10, and to transfer data and/or electrical energy to the transceiver 10. In another particular embodiment of the invention, the cradle 50 may include a data storage unit configured to receive imaging information generated by the transceiver 10 (not shown), and may also include a data interface 13 that may be employed to transfer the acquired imaging information to other processors or systems for further image processing. In a particular embodiment, the data interface may include a universal serial bus (USB) interface having a connecting cable 53. In other embodiments, the data interface 13 may include a FIREWIRE interface, an RS-232 interface, or other similar and known interface devices. In still another particular embodiment, the data interface 13 may be used to transfer programmed instructions to a processing device positioned within the transceiver 10.

Figure 5:
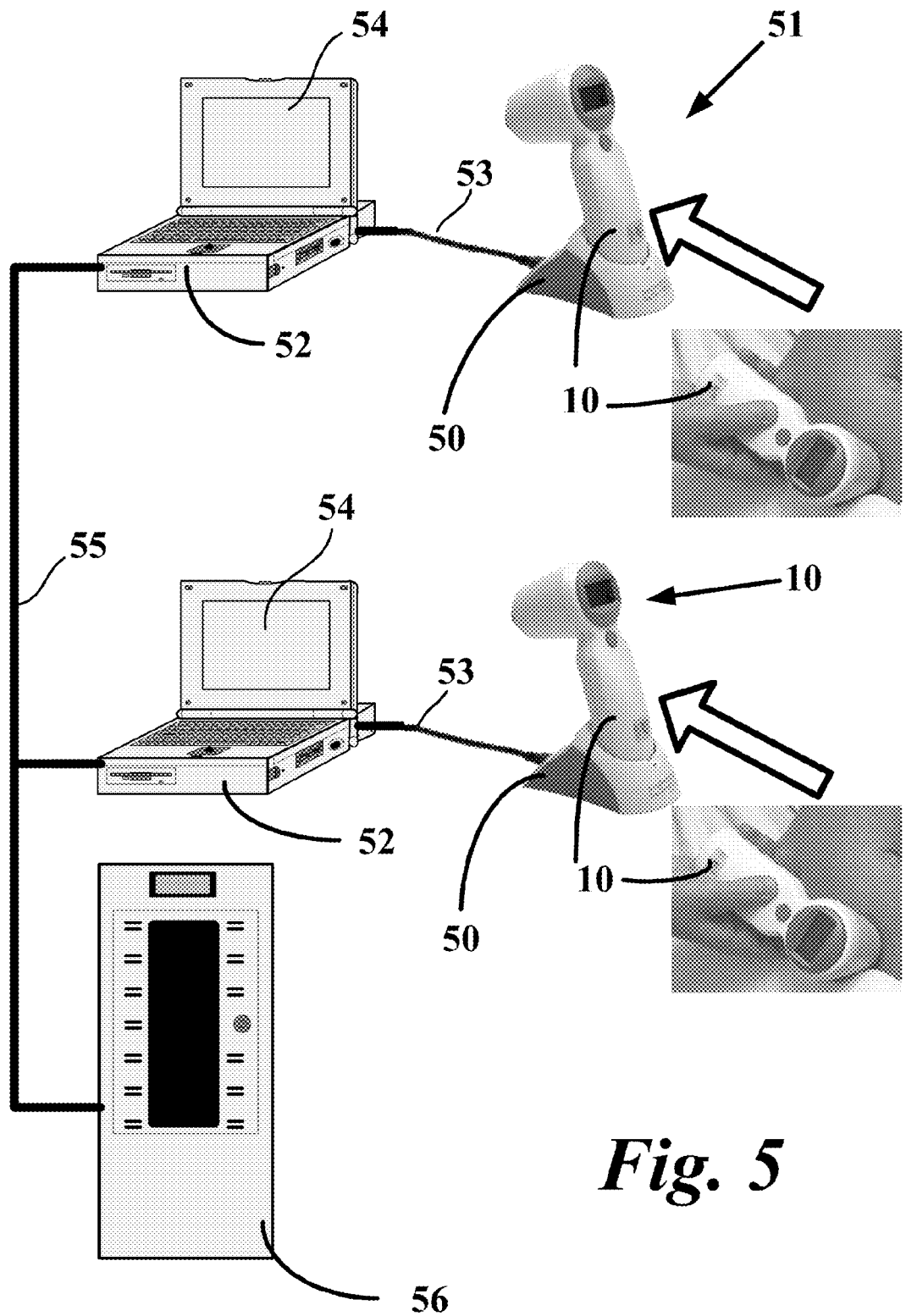
FIG. 5 is a partially-schematic view of an imaging system according to another embodiment of the invention.

FIG. 5 is a partially schematic view of an imaging system 51 according to another embodiment of the invention. The system 51 includes at least one transceiver 10 in communication with a computer device 52 that is further in communication with a server 56. The at least one transceiver 10 is operable to project ultrasound energy into a patient and to receive the resulting ultrasound echoes, as previously described. The ultrasound echoes may be converted to digital signals within the transceiver 10, or alternately within the computer device 52 that is coupled to the transceiver 10. Similarly, the digital signals may be stored and processed in the transceiver 10, or within the computer device 52 to generate ultrasound images that may be viewed on a display 54 that is coupled to the computer device 52. In either case, the transceiver 10 may be coupled to the computer device 52 by the connecting cable 53, or by means of a wireless link, such as an ETHERNET link, or an infrared wireless link. The transceiver 10 and/or the computer device 52 are configured to process the digital signals using algorithms that will be explained in greater detail below.

Still referring to FIG. 5, the computer device 52 may communicate information to the server 56, which is configured to receive processed images and/or image data from the computer device 52 and/or the transceiver 10. The server 56 may include any computer software and/or hardware device that is responsive to requests and/or issues commands to or from at least one client computer (not shown in FIG. 5). The server 56 is coupled to the computer device 52 by a local communications system 55, such as a telephone network or a local area network (LAN) or other similar networks.

The operation of the imaging system 51. Each transceiver 10 may be separately and independently used to project ultrasound information into a selected region of the patient and to transmit the signals proportional to the received ultrasound echoes to the computer device 52 for storage and/or further processing. If the image processing occurs in the computer device 52, each computer device 52 includes imaging software having instructions to prepare and analyze a plurality of one dimensional images from the stored signals and to transform the plurality of images into a plurality of two-dimensional scanplanes, as previously described. Additionally, the imaging software programs may also present three-dimensional renderings from the plurality of two-dimensional scanplanes. Each computer device 52 may also include instructions to perform other additional ultrasound image enhancement procedures, which may include instructions to implement the image processing algorithms.

In another embodiment of the system 51, the imaging software programs and other instructions that perform additional ultrasound enhancement procedures are located on the server 56 Each computer device 52 coupled to the system 51 receives the acquired signals from the transceiver 10 using the cradle 50 and stores the signals in the memory of the computer device 52. The computer device 52 subsequently retrieves the imaging software programs and the instructions to perform the additional ultrasound enhancement procedures from the server 56. Thereafter, each computer device 52 prepares the one-dimensional images, the two-dimensional images, and the three-dimensional renderings, as well as enhanced images from the retrieved imaging and ultrasound enhancement procedures. Results from the data analysis procedures may then be sent to the server 56 for storage.

In still another embodiment of the system 51, the imaging software programs and the instructions to perform the additional ultrasound enhancement procedures are located in the server 56 and executed on the server 56. Each computer device 52 in the system 51 receives the acquired signals from the transceiver 10 and sends the acquired signals to the memory of the computer 52 through the cradle 50. The computer device 52 subsequently sends the stored signals to the server 56. In the server 56, the imaging software programs and the instructions to perform the additional ultrasound enhancement procedures are executed to prepare the one-dimensional images, two-dimensional images, three-dimensional renderings, and enhanced images from the signals. Results from the data analysis procedures may be stored by the server 56, or alternatively, sent to a client computer coupled to the server for archival storage, or for other purposes.

Figure 6:
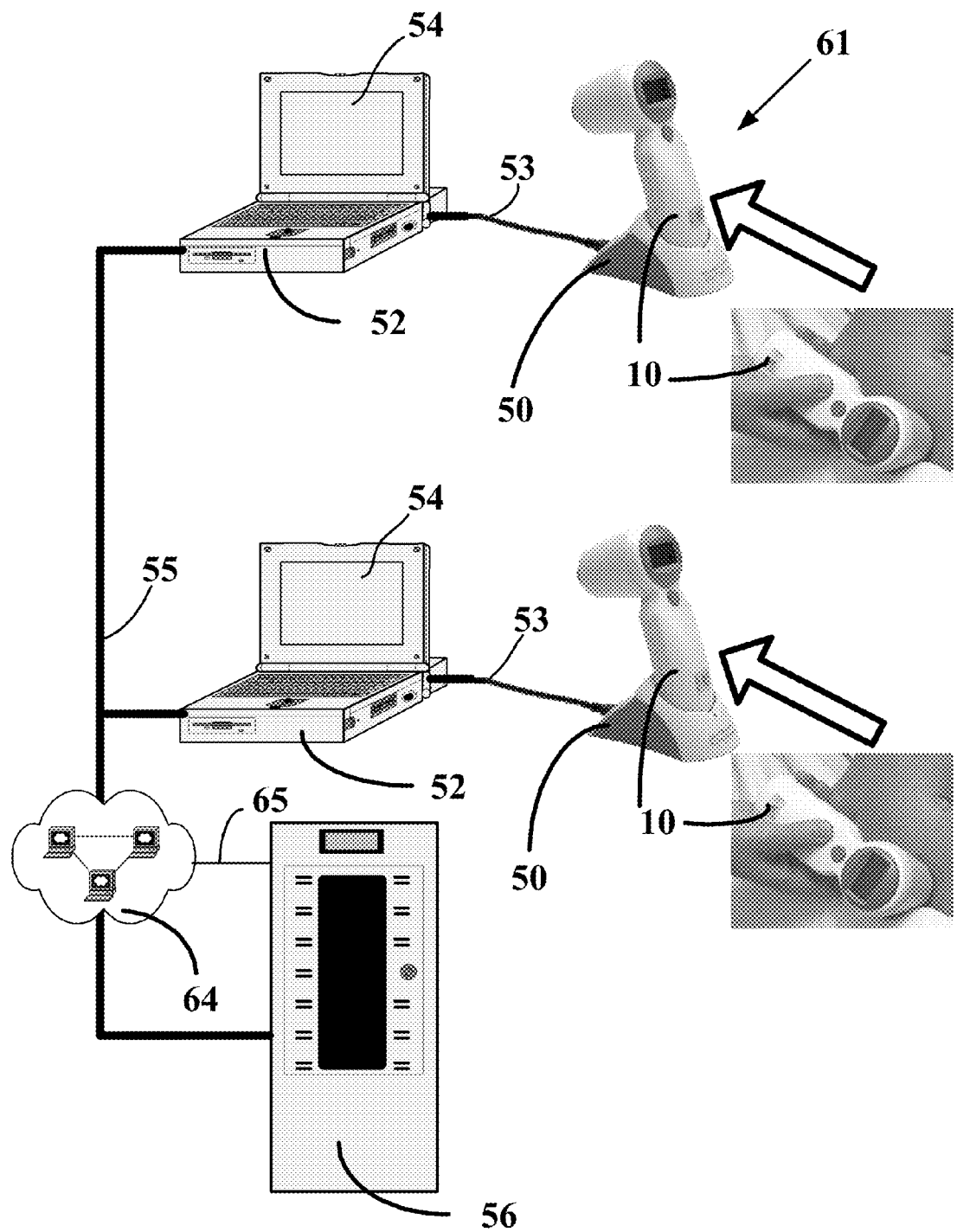
FIG. 6 is a partially-schematic view of a networked imaging system according to still another embodiment of the invention.

FIG. 6 is a partially schematic view of a networked imaging system 61 according to still another embodiment of the invention. Many of the elements of the present embodiment have been discussed in detail in connection with other embodiments, and in the interest of brevity, will not be discussed further. The networked imaging system 61 includes a public data network 64 interposed between the computer device 52 and the server 66. The public data network 64 may include a LAN, a WAN, or the Internet. Accordingly, other computational devices associated with the public data network 64 may communicate imaging data and/or ultrasound images with the portable computing devices 52 and the server 56. Although two transceivers 10 are shown in the networked imaging system 61 shown in FIG. 6, fewer that two, or more than two transceivers 10 may be present. The public data network 64 advantageously permits the system 61 to communicate images and data to other computer devices and/or processors.

Figure 7:
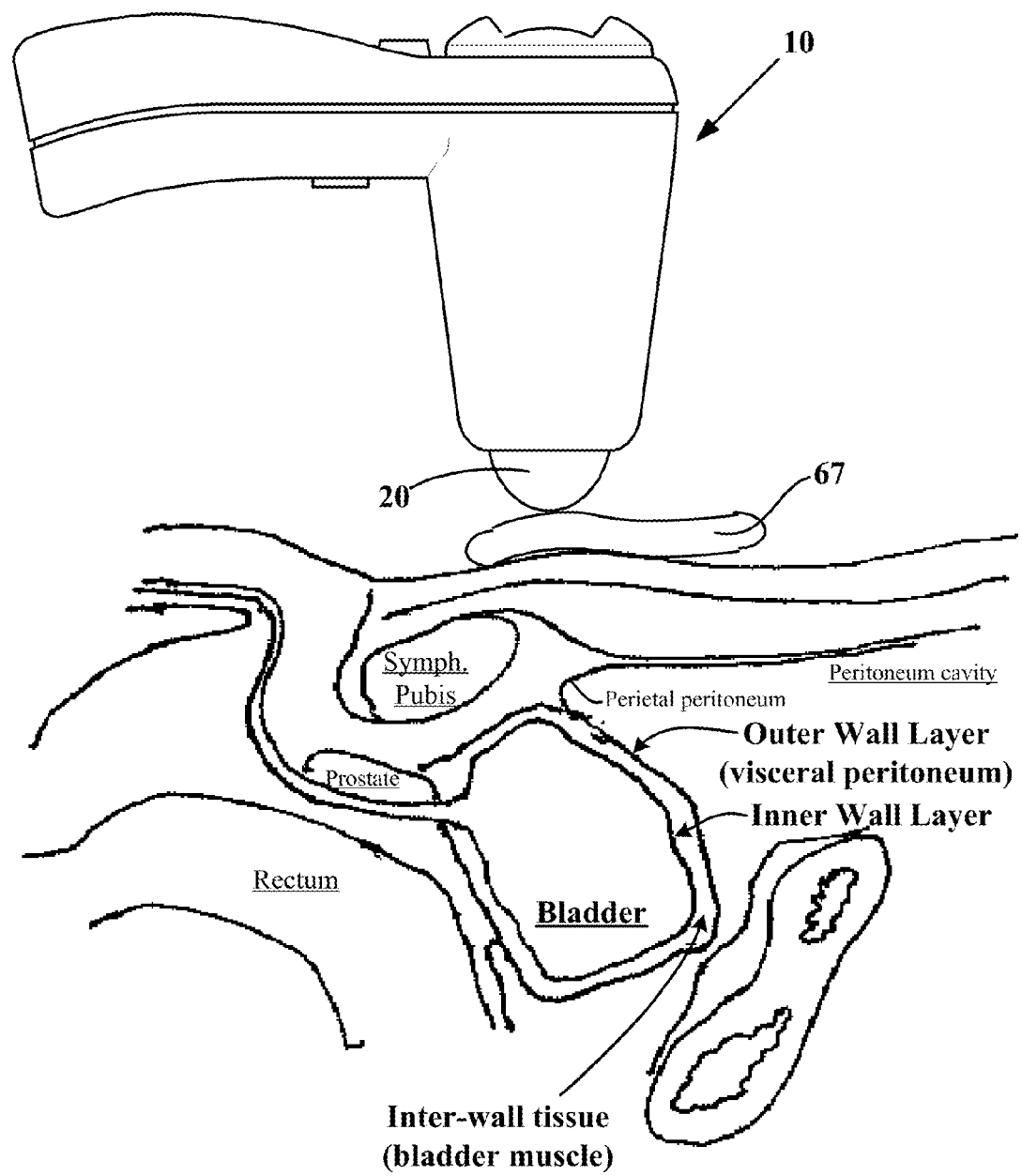
FIG. 7 is a cross sectional view of a selected anatomical portion that will be used to further describe the various embodiments of the present invention.

FIG. 7 is a cross sectional view of a selected anatomical portion that will be used to further describe the various embodiments of the present invention. As shown in FIG. 7, the transceiver 10 is placed over the anatomical portion, which may include a urinary bladder and surrounding tissues of a male patient. Also shown, the dome 20 of the transceiver is placed in contact with a sonic coupling gel contained within a pad 67 to minimize ultrasound attenuation between the patient and the transceiver 10. Alternatively, the dome 20 may be placed in contact with a sonic coupling gel applied on the patient's skin. A wall of the urinary bladder may be divided into three distinct and observable layers, including an outer wall layer (visceral peritoneum), an opposing inner wall layer, and an inter-wall layer positioned between the outer layer and the inner layer. In general, muscular contraction in the bladder results from muscular tissue in the inter-wall layer, so that urine within the bladder may be excreted. The bladder wall thickness typically varies between about 1.0 millimeter (mm) and about 4.0 millimeters (mm). Since the volume of the bladder wall is a product of an area of the bladder and the thickness of the bladder wall, an estimation of the bladder wall volume is reasonably accurate if the surface area determination of the bladder wall and the thickness of the bladder wall is sufficiently precise. Assuming the thickness of the bladder wall is substantially uniform around the bladder, a bladder wall mass can be calculated as a product of the bladder wall volume and an estimation of the density of the wall tissue. The bladder wall mass calculations are thus similarly limited by the accuracy of the bladder wall surface area determination and the bladder wall thickness measurement.

Figure 8:
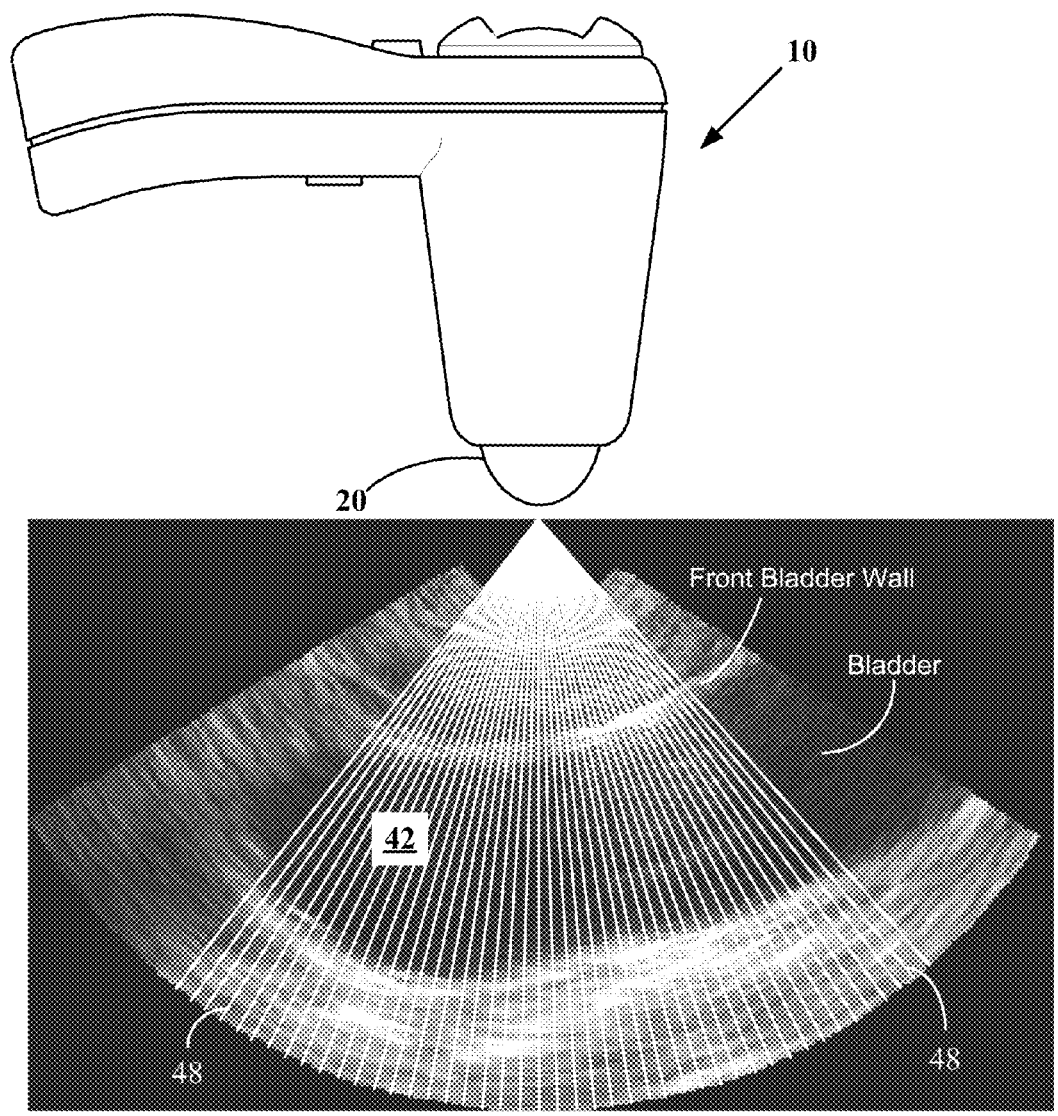
FIG. 8 is a cross sectional view of the anatomical region of FIG. 7 as the region is imaged by the transceiver of FIG. 1.
Figure 9:
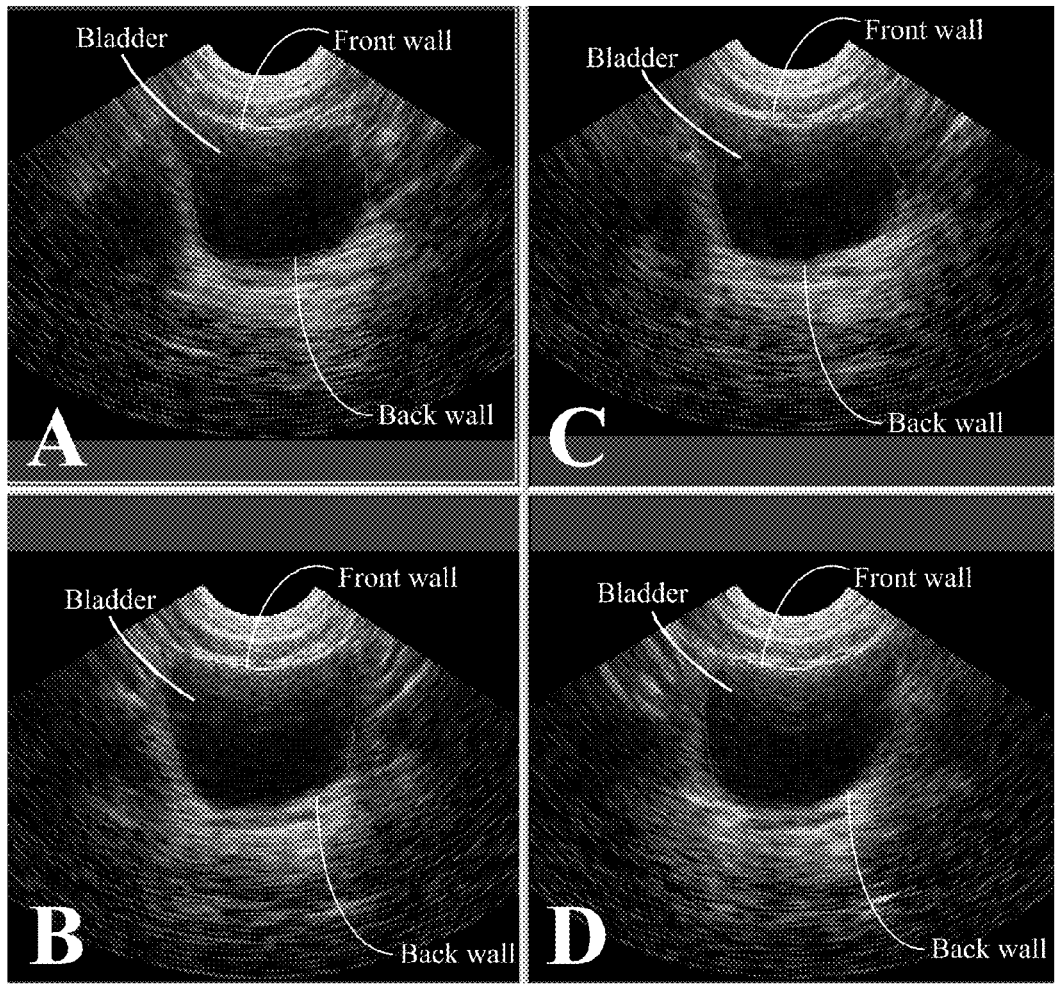
FIGS. 9A through 9D are four exemplary and sequential ultrasound images obtained from a male subject during an ultrasound examination.
Figure 10:
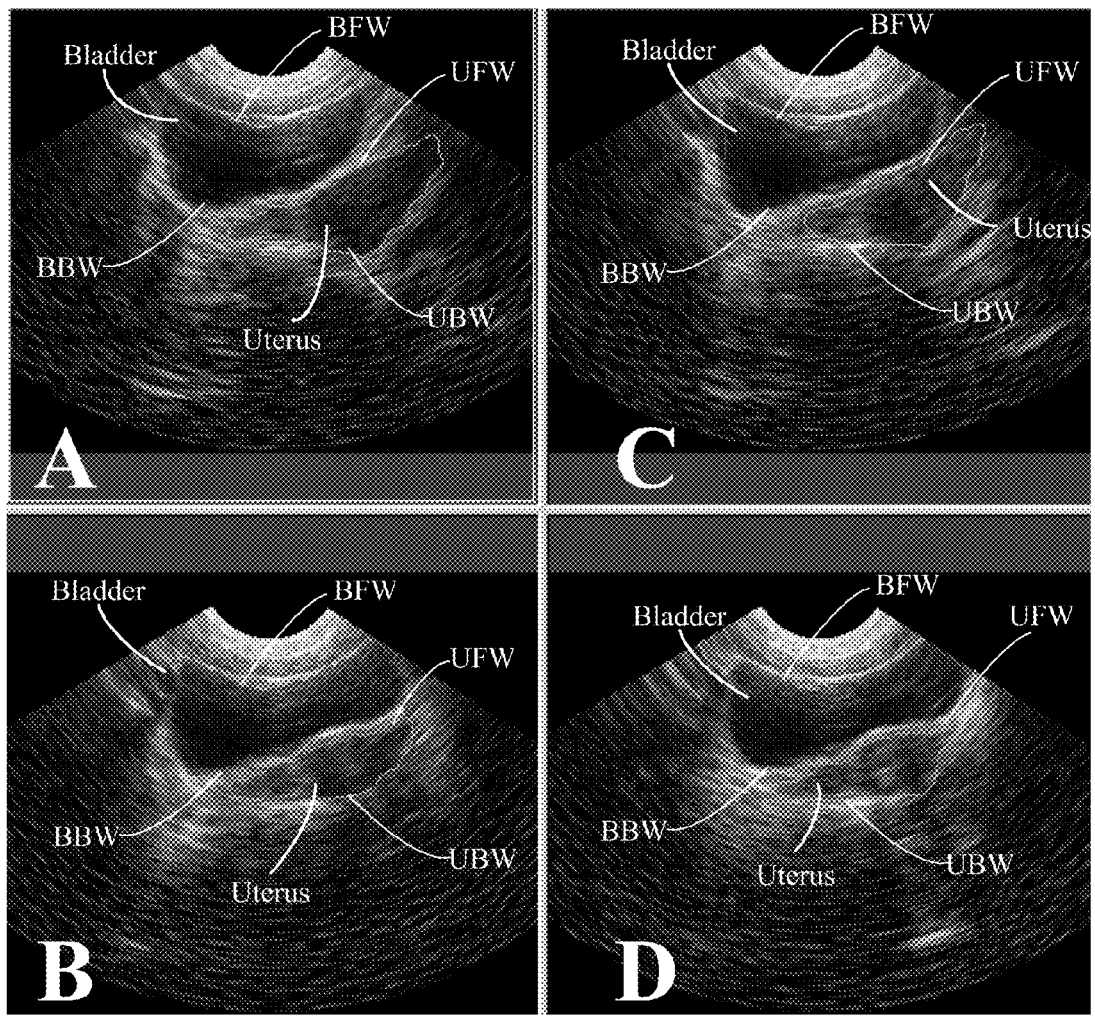
FIGS. 10A through 10D are four exemplary and sequential ultrasound images obtained from a female subject during an ultrasound examination.

FIG. 8 is a cross sectional view of the anatomical region of FIG. 7 as the region is imaged by the transceiver 10. As previously described, the transceiver 10 is operable to image the anatomical region by generating a scanplane 42 that is further comprised of a plurality of scanlines 48. In FIG. 8, the partial scanplane 42 is superimposed on a B-mode ultrasound image of the anatomical region in order to illustrate the plurality of scanlines 48 crossing the front bladder wall (e.g., the wall closer to the dome 20) and extending through the bladder to the back wall of the bladder.

FIGS. 9A through 9D are four exemplary and sequential ultrasound images obtained from a male subject during an ultrasound examination. The ultrasound images were obtained using lower resolving B-mode algorithms, and show a bladder volume surrounded by a bladder wall. In FIGS. 9A through 9D, the front and back walls of the bladder are shown surrounding a generally darker bladder volume. As shown in FIGS. 9A through 9D, the front wall and the back wall of the bladder are relatively poorly defined.

FIGS. 10A through 10D are four exemplary and sequential ultrasound images obtained from a female subject during an ultrasound examination. The ultrasound images in FIGS. 10A through 10D were also obtained using lower resolving B-mode algorithms. In FIGS. 10A through 10D, the bladder is similarly poorly defined, and a uterine structure is detected beyond the bladder. The bladder front wall (BFW) and an opposing bladder back wall (BBW) along with the uterine front wall (UFW) and a uterine back wall (UBW) are imaged, but are still rather poorly defined. Thus, the ability to easily discern the front and back walls of a uterus and a bladder from the same female subject using selected wall locations obtained from B-mode imaging is difficult to establish. In particular, the determination of the narrower distances between the outer and inner wall layer locations of the uterus or bladder is often very difficult to establish.

Figure 11:
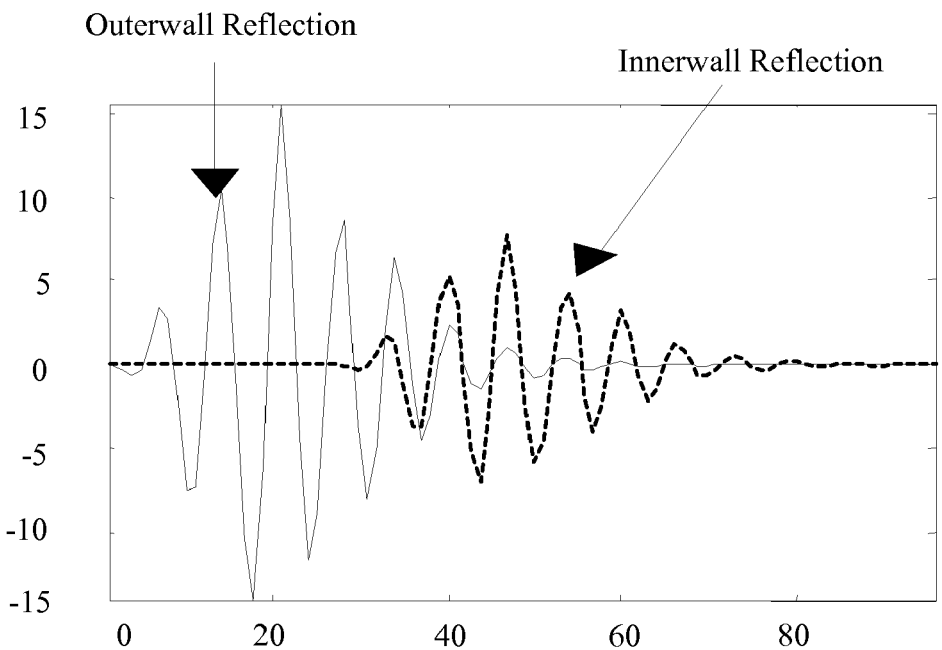
FIG. 11 is an exemplary, non-rectified echogenic signal received along a selected scanline during ultrasound imaging of a bladder.

FIG. 11 is an exemplary, non-rectified echogenic signal received along a selected scanline during ultrasound imaging of a bladder. The echogenic signal pattern includes an outer wall reflection, which is shown as a solid line, which results from a reflection that occurs at the outer wall of a bladder (as best seen in FIG. 7), and an inner wall reflection (as also shown in FIG. 7), resulting from a reflection occurring at an inner wall of the bladder, which is shown as a dashed line. Since the non-rectified inner wall reflection and the outer wall reflection signals at least partially overlap, it may be difficult to accurately discern a location of the inner wall of the bladder from the outer wall location.

Figure 12:
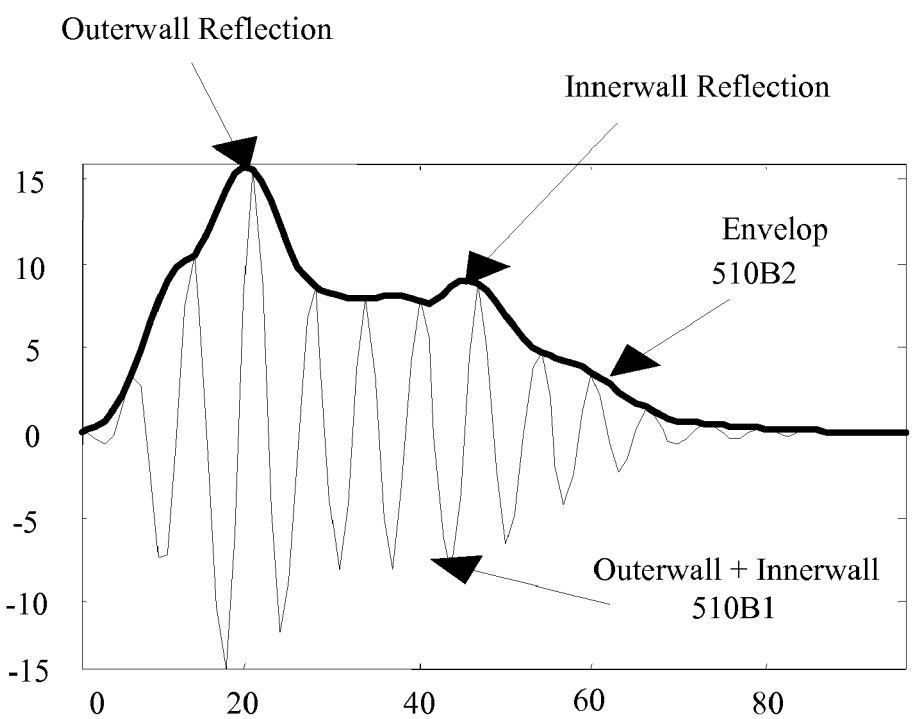
FIG. 12 is an exemplary processed echogenic signal pattern from the selected scanline of the bladder imaging of FIG. 15.

FIG. 12 is an exemplary processed echo signal pattern from the selected scanline of the bladder imaging of FIG. 8. The outer wall and inner wall reflection signals are algebraically summed and rectified to generate a signal envelope waveform. Rectification is achieved by performing a Hilbert transform to the algebraically summed waveform. The positive signal envelope waveform obtained by the Hilbert transform advantageously allows a central location of the outer and the inner layers of the front organ walls to be accurately located since the envelope exhibits a more pronounced signal peak corresponding to the outer and the inner walls.

Figure 13:
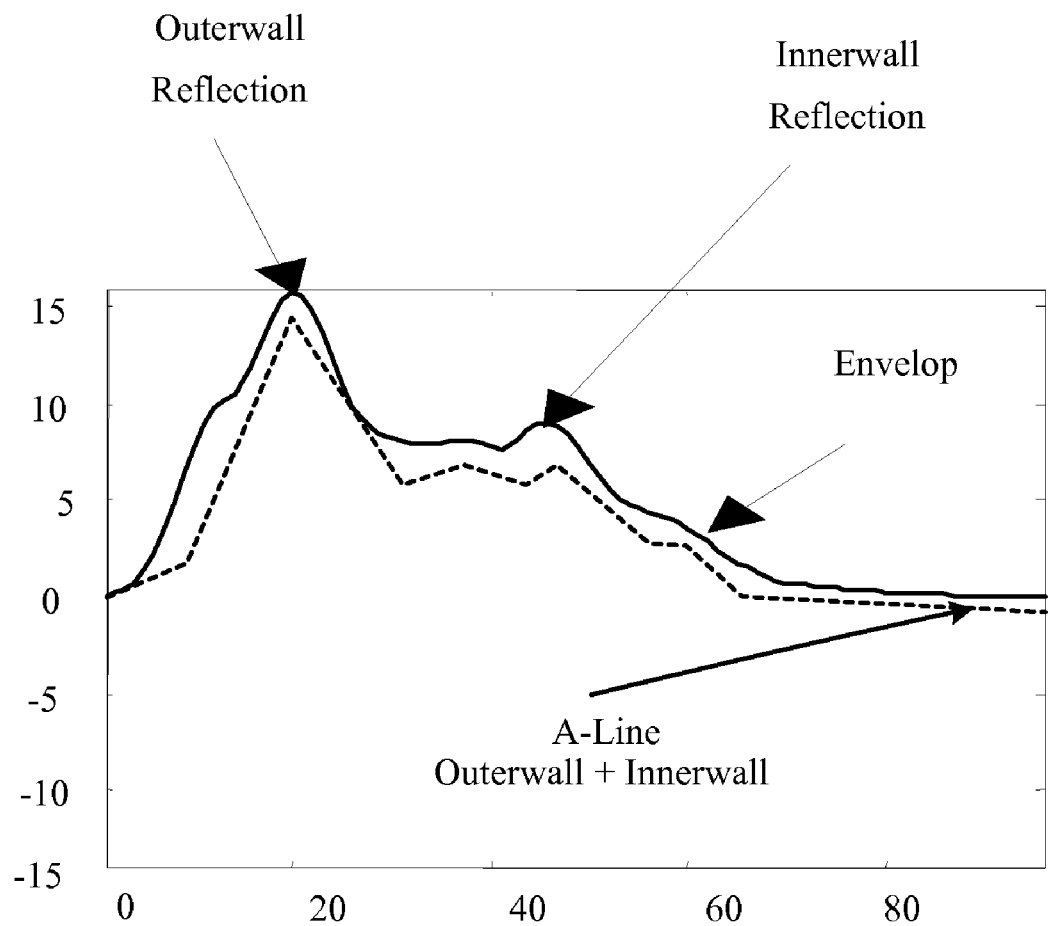
FIG. 13 is the processed echogenic signal pattern of FIG. 12 that further shows a waveform that is generated by additional processing of the rectified waveform.

FIG. 13 is the processed echogenic signal pattern of FIG. 12 that further shows a waveform that is generated by additional processing of the rectified waveform. The waveform (represented by a dotted line in FIG. 13) may be generated by processing the rectified waveform of FIG. 12 using an A-mode algorithm so that selected bladder wall locations may be more easily identified. The processed rectified waveform is generally sharper and/or exhibits peaks that permit various maximum points on the processed rectified waveform may be easily identified. Once identified, the maximum waveform points may then be used to select candidate points for further bladder wall imaging, described below.

Figure 14:
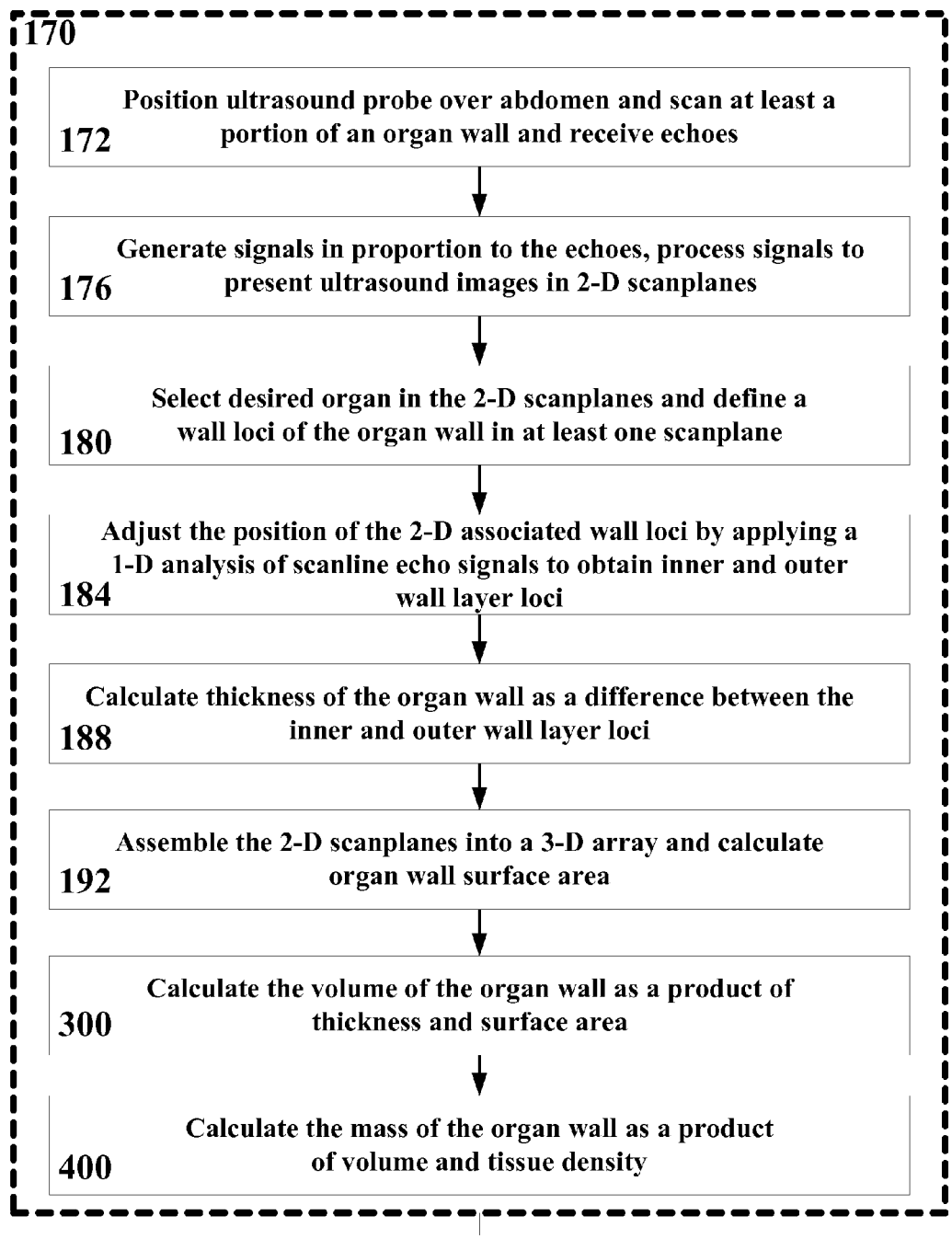
FIG. 14 is a method algorithm of the particular embodiments.

FIG. 14 is a method algorithm of the particular embodiments. The method algorithm 170 is comprised of 8 sub-algorithms that culminate in the calculation of the mass of the organ wall. In block 172, the ultrasound probe is positioned over the abdomen of a patient and a scan is commenced to acquire at least a portion of an organ wall image. The echoes are received and processed in the next block, block 176. A block 176 signals are generated from the echoes in proportion to their signal strength and the signals are processed and presented as a 2-D ultrasound image in the format of two-dimensional scanplanes. This is commonly referred to as B-mode ultrasound. The next block is block 180 in which the desired organ in the 2-D scanplanes is selected and wall loci of the organ wall in at least one scanplane is delineated. Algorithm 170 continues with block 184 in which the initial wall delineation from the 2-D scanplane is now further refined or adjusted. The adjustment of the 2-D wall loci position is achieved by applying a 1-D analysis of the scanline echo signals to obtain inner and outer wall layer loci. The next block is block 188 in which the thickness of the organ wall is calculated as a difference between the inner and outer wall layer loci as determined from block 184. The algorithm 170 continues with block 192 in which 2-D scanplanes obtained from B-mode ultrasound are assembled into a 3D array and the wall surface area of the organ wall is calculated. In block 300, the volume of the organ wall is calculated as a product of the thickness as determined from block 188 and the surface area as determined from block 192. Finally, in block 400, the mass of the organ wall is calculated as a product of the volume obtained from block 300 and the tissue density of the organ wall.

Figure 15:
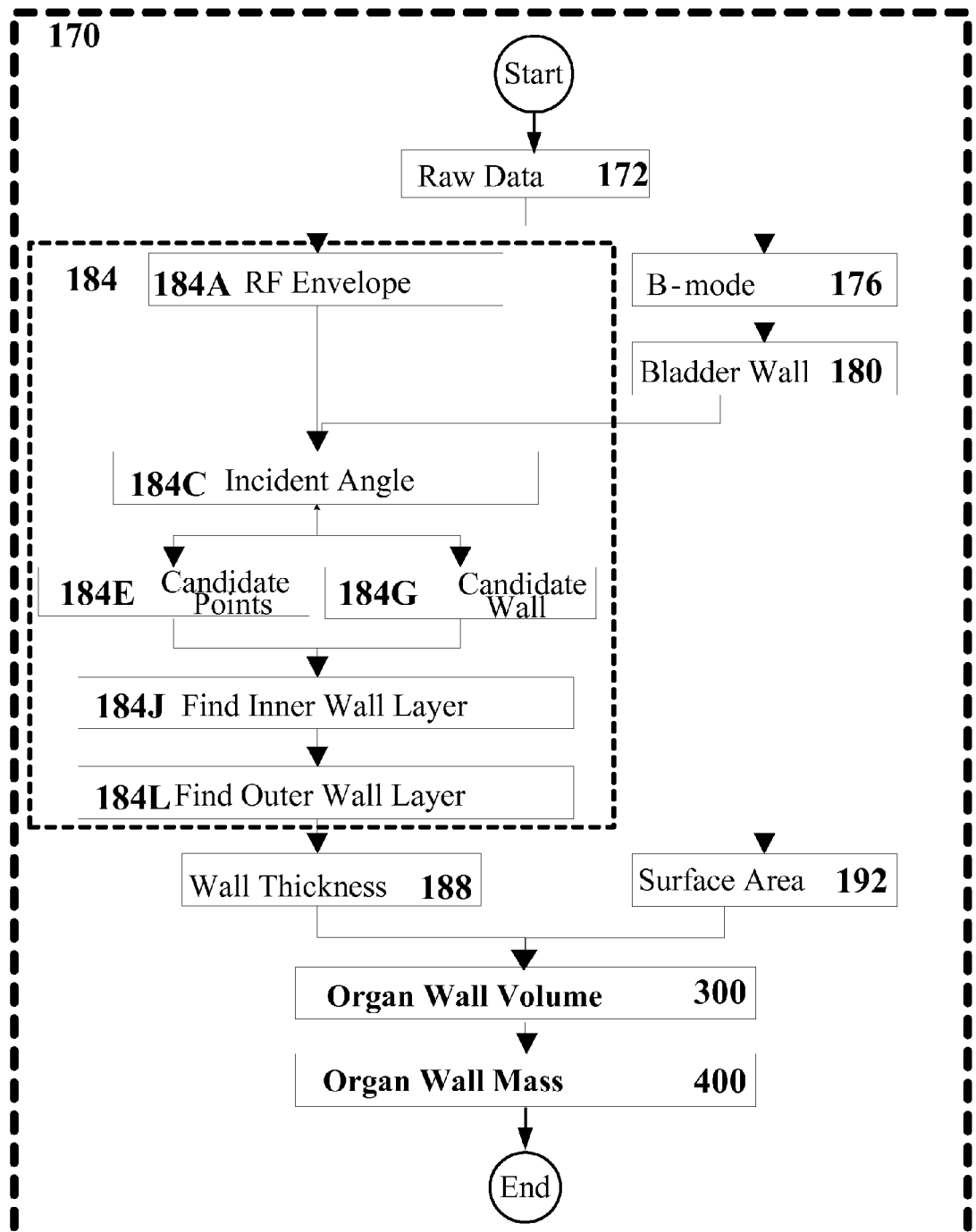
FIG. 15 is a flowchart that describes a method for scanning a bodily organ, according to an embodiment of the invention.

FIG. 15 is a flowchart that will be used to describe a method 170 for scanning a bodily organ, according to an embodiment. At block 172, ultrasound energy is projected into the bodily organ, and reflections from various internal structures are acquired, that constitutes raw ultrasound data. The raw data may be collected, for example, using the device shown in FIG. 1, or in any of the other disclosed embodiments described herein. Block 184 describes the procedures to obtain points for the inner and outer wall layers. At block 184A, the raw data is processed to generate an RF envelope, as earlier described and shown in FIG. 16 and FIG. 17. In addition, at block 176, B-mode scans of the bodily organ are also compiled. Based upon the B-mode data acquired at block 176, a family of bladder wall locations may be generated, as will be described below.

At block 184C, incident angles for each of the scanlines projected into the bodily organ are calculated as will also be described below. In general terms, the calculation of the incident angle permits better discrimination between an inner wall and an outer wall of the organ. At block 184E, candidate points that characterize the position of the inner wall, the outer wall and the position of intermediate layers between the inner wall and the outer wall are determined. The determination of candidate points will also be described in greater detail below. Based upon the candidate points generated at block 184E, candidate walls may be generated at block 184G. The candidate walls comprise a family of possible wall locations, which will be further processed, as described below.

Still referring to FIG. 15, at block 184J, an inner wall layer location is identified from amongst the candidate walls determined at block 184G. An outer wall location is also identified at block 184L, which represents a refined estimate of an actual outer wall layer location. The determination of the inner wall location and the outer wall location will be described in greater detail below. Based upon the inner wall layer and the outer wall layer determinations at blocks 184J and 184L, respectively, and the incident angle determinations at block 184C, a wall thickness may be determined at block 188. A surface area of the bodily organ may be determined based upon the B-mode data collected at block 192. Based upon the surface area determination at block 192 and the wall thickness determination at block 188, an organ volume value 300 and an organ mass value 400 for the organ wall may then be determined by routine calculation.

Figure 16:
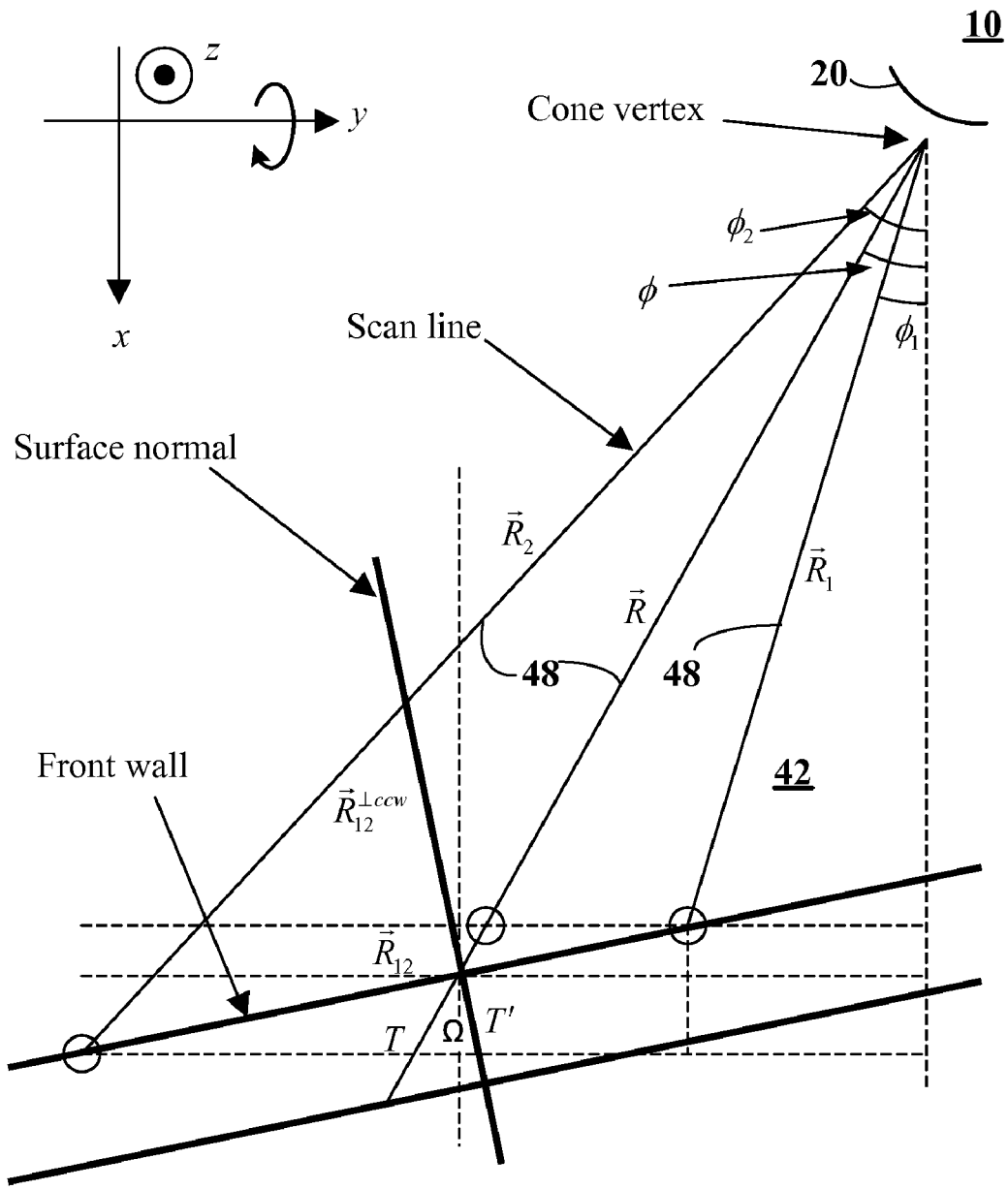
FIG. 16 is a diagram that describes a method for determining incident angles.

In FIG. 16, a method for determining incident angles will now be described. The scancone 20 of the transceiver 10 (FIG. 1) projects ultrasound energy towards an anatomical portion that includes a front wall of a bodily organ, such as a urinary bladder. In general, the scancone 20 is positioned at an angle $\Omega$ with respect to a normal direction relative to the bladder wall of a patient. A wall thickness is defined by a distance between an inner wall and an outer wall of the bladder along the surface normal T. Also, the inner and outer walls are most clearly discerned on scanlines that are normal to the bladder surface. Accordingly, the incident angle of each of the scanlines 48 of the scanplane 42 is supplied. A first vector $R_1$ extends along a first scanline having a tilt angle $\phi_1$ and a second vector $R_2$ extends along a second scanline having a tilt angle $\phi_2$. Accordingly, a vector $R_{12}$ that is a difference between the first vector $R_1$ and the second vector $R_2$ extends between $R_1$ and $R_2$.

Figure 18:
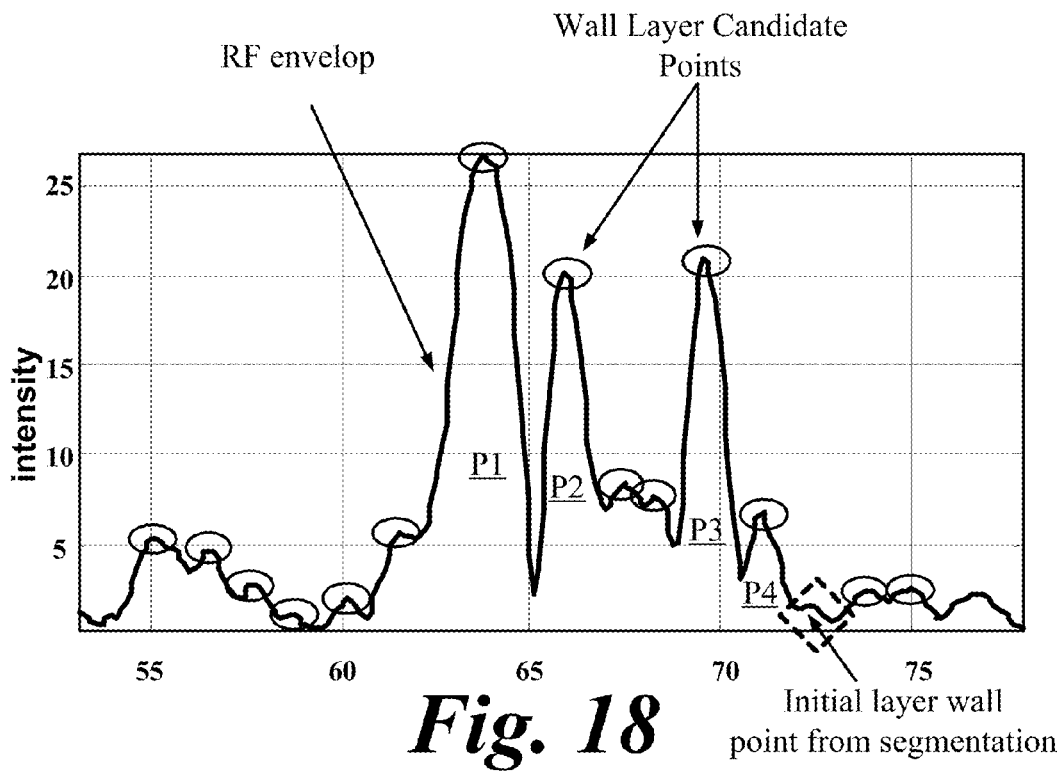
FIG. 18 is an envelope of a scanline having an echogenic intensity distribution that crosses highly reflective adipose.

In general, the vector $\vec{R}$ extends from the cone vertex at an incident angle $\phi$. In the interest of clarity of illustration, a two-dimensional representation of $\vec{R}$ is shown in FIG. 18. It is understood, however, that the vector $\vec{R}$ is oriented in three-dimensional space. Accordingly, in the description that follows, the vector $\vec{R}$ may be expressed in equation E1 as:

$$\vec{R} = (R\cos\phi, R\sin\phi, 0) \qquad \text{E1}$$

where, R is the distance between the cone vertex and a segmentation point positioned on the front wall. The two adjacent neighbor points, $\vec{R}_1$ and $\vec{R}_2$, are expressed similarly in equation E2 and E3:

$$\vec{R}_1 = (R_1\cos\phi_1, R_1\sin\phi_1, 0) \qquad \text{E2}$$

$$\vec{R}_2 = (R_2\cos\phi_2, R_2\sin\phi_2, 0) \qquad \text{E3}$$

The surface vector, $\vec{R}_{12}$, may be expressed in terms of the two adjacent points, $\vec{R}_1$ and $\vec{R}_2$ by a vector addition, as follows in equation E4:

$$\vec{R}_{12} = \vec{R}_2 - \vec{R}_1 \qquad \text{E4}$$

The surface normal vector T is orthogonal to the surface vector, $\vec{R}_{12}$. When the vector T is rotated through an angle $\theta$ about the y-axis, a rotation matrix and an orthogonal matrix may be defined, respectively, as follows:

$$\begin{bmatrix} \cos\theta' & 0 & -\sin\theta' \\ 0 & 1 & 0 \\ \sin\theta' & 0 & \cos\theta' \end{bmatrix} \text{ and } \begin{bmatrix} 0 & -1 & 0 \\ 1 & 0 & 0 \\ 0 & 0 & 1 \end{bmatrix}$$

where in the present case, $\theta'$ is an angle between the orthogonal plane, and if the image is in a first plane, the angle $\theta'$ will be zero, and if the image is the 13th plane (in a 24-plane image), the angle $\theta'$ will be the incident angle of the broadside scanline relative to the first plane.

Therefore, a surface normal vector, $\vec{R}_{12}^{\perp ccw}$ may be calculated using the above rotation and orthogonal matrices as described in equation E5.

$$\vec{R}_{12}^{\perp ccw} = \begin{bmatrix} \cos\theta' & 0 & -\sin\theta' \\ 0 & 1 & 0 \\ \sin\theta' & 0 & \cos\theta' \end{bmatrix} \begin{bmatrix} 0 & -1 & 0 \\ 1 & 0 & 0 \\ 0 & 0 & 1 \end{bmatrix} \vec{R}_{12} \qquad \text{E5}$$

The angle between the two vectors, $\vec{R}$ and $\vec{R}_{12}^{\perp ccw}$ is the incident angle $\theta$, which may be determined as follows in equation E6:

$$\theta = \vec{R} \angle \vec{R}_{12}^{\perp ccw} = \cos^{-1}\left(\frac{\vec{R} \bullet \vec{R}_{12}^{\perp ccw}}{\|\vec{R}\| \cdot \|\vec{R}_{12}^{\perp ccw}\|}\right) \qquad \text{E6}$$

where "$\|\bullet\|$" indicates a vector length and "●" is the dot product of the two vectors.

The above method can be extended to calculate the incidence angle in a three-dimensional space. In case of such a three dimensional extension, a two-dimensional plane is fit to all points in the neighborhood of point $\vec{R}$. The normal direction to this plane is determined $\vec{R}_{12}^{\perp CCW}$ and then the incidence angle is calculated as in Equation E6. To fit the plane to a neighborhood of points and determine the normal direction to the plane, an eigenvector-based approach is used. First calculate a 3 by 3 covariance matrix C for all the points in the neighborhood of point $\vec{R}$. The eigenvalues and the eigenvectors of this 3 by 3 matrix are then calculated. Thereafter, the normal direction is determined the eigenvector corresponding the smallest eigenvalue.

Figure 17:
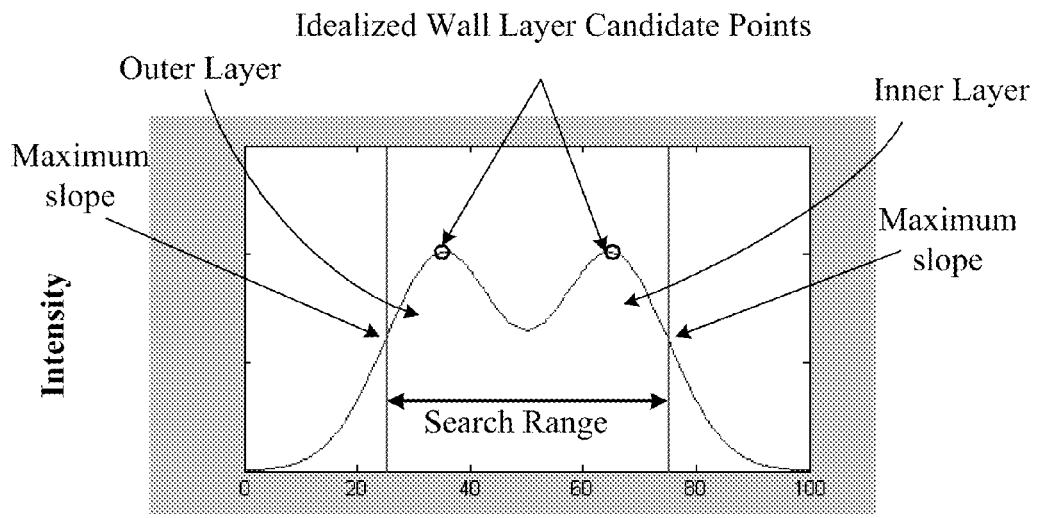
FIG. 17 is an idealized diagram of an echogenic envelope having an intensity pattern that crosses a front bladder organ wall.

FIG. 17 is a diagram that shows an idealized envelope having echogenic intensity distributed along a scanline similar to the scanline 48 of FIG. 8 that crosses the front bladder wall. In FIG. 17, only the echogenic pattern of the front bladder wall is shown, so that the strongly echogenic patterns caused by adipose and peritoneum tissues are not shown. The front wall profile shown in FIG. 17 is bimodal, and where the proximal wall outer layer generates an outer layer peak having a signal midpoint maxima near a distance value of 30, a middle layer (bladder muscle) having a signal minima near a distance value of 50, and a distal inner layer peak that presents another signal midpoint maxima near a distance value of 70. A search region for candidate points may therefore include at least the distance between the exterior slopes the outer and inner layers peaks, indicated by the vertical lines that intersect near a distance value of 25 for the outer layer peak and near a distance value of 75 for the inner layer peak.

FIG. 18 is an actual echogenic envelope distribution along a scanline that crosses highly reflective adipose and peritoneum tissues. The echogenic distribution is therefore more complex than the distribution shown in FIG. 17, since signal variation and/or noise are included. FIG. 18 also shows a plurality of possible candidate points that may be used to identify the inner and the outer wall layers of the bladder. The inner and outer wall layer candidate points are present as local peak maxima, and are shown by ovals in FIG. 18. The candidate points are determined by one-dimensional A-mode algorithms applied to the distribution, as will be discussed in more detail below. Accordingly, FIG. 18 shows, for example, a total of fifteen local maxima, which correspond to fifteen inner and outer layer candidate points, although either more than fifteen, or fewer than fifteen candidate points may be present in other similar distributions.

Still referring to FIG. 18, the inner and outer wall layer candidate points are developed by higher resolution one-dimensional algorithms applied to scanlines 48, (FIG. 8) which use an initial inner layer anchor point determined by a two-dimensional segmentation algorithm having generally less resolution. The initial inner layer anchor point on the scanline 48, which in the present example are determined by the two-dimensional B-mode segmentation algorithms, are shown in FIG. 18 as a diamond with dashed lines. The segmentation anchor point serves as a reference point that permits the adequacy of the one-dimensional inner and outer wall layer candidate points to be determined.

With continued reference to FIG. 18, localized peaks P1, P2, P3, and P4 are shown that resemble the outer-inner layer bimodal pattern of FIG. 17. For example, in the region between a distance 65 and a distance 71, the peaks P2 and P3 appear to closely approximate the bimodal pattern of FIG. 17 since the signal magnitude of the point P2 is approximately the same as for the point P3. A local minimum is present between the points P2 and P3, which correspond to two minor maxima. If the region between and including P2 and P3 represents a front bladder wall, then the higher magnitude P1 could be indicative of the more reflective peritoneal or adipose tissues that are anterior or proximate to the dome 20 (FIG. 7 or 8).

Although the combination of the candidate points P2 and P3 appear to present a favorable candidate for the location of the outer and inner bladder walls, respectively, other combinations are possible. For example, the points P1 and P2, and the points P3 and P4 may also represent the location of the outer and inner bladder walls. Moreover, any combination of the fifteen local maxima or candidate points shown in FIG. 20 may be used to determine a location of the front wall. Algorithms will be described below that may be implemented to select envelope peak candidates within a particular scanline 48 with enhanced confidence. Accordingly, a peak combination representing the location of the bladder wall may be identified with increased accuracy.

Figure 19:
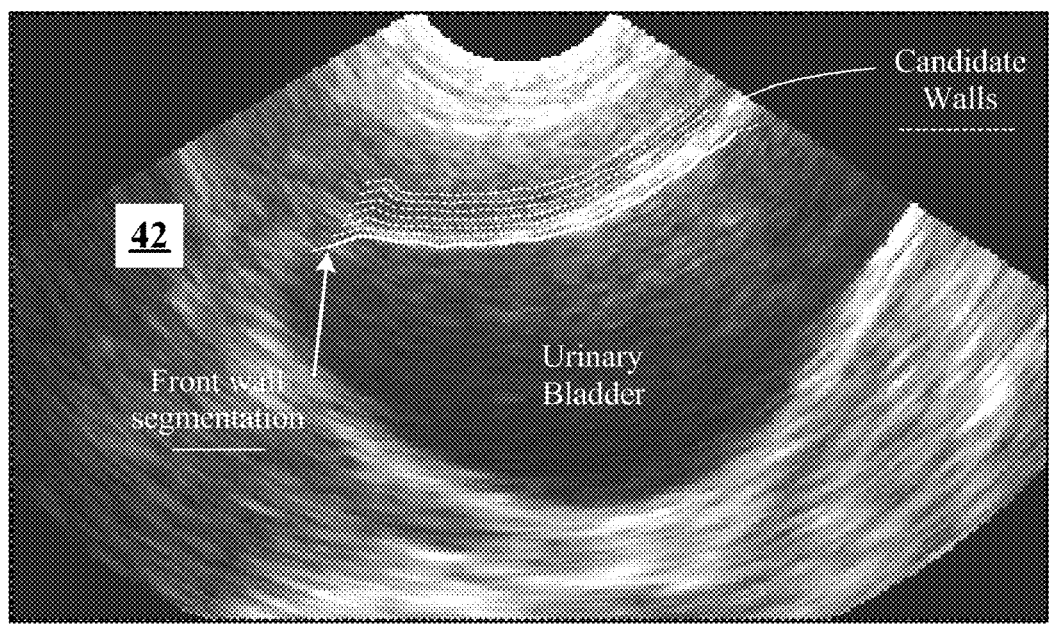
FIG. 19 is a B-mode ultrasound image that shows a family of wall layer locations corresponding to the candidate points of FIG. 18.

FIG. 19 is a B-mode ultrasound image that shows a family of wall layer locations corresponding to the candidate points of FIG. 18 assembled from adjacent scanlines 48. The continuous white line shown in FIG. 19 represents an initial inner wall location of the bladder superimposed onto the image as determined by the two-dimensional B-mode segmentation algorithms. The dashed lines shown in FIG. 19 represent candidates for the location of outer wall layers that, in the present case, progress outwardly towards the dome cutout 41 (FIGS. 3C through 3E). The family of seven dashed lines indicate the seven possible outer layer wall locations, some of which are overlapping with the initial inner wall as determined by the two-dimensional B-mode segmentation algorithms.

As shown in FIG. 19, the application of all the candidate points (FIG. 18) suggests that estimates of the thickness of the bladder wall can vary from nearly zero, to multiple centimeters. Algorithms to identify an optimum set of candidate points from the group of all of the candidate points generated is therefore preferable to select the final wall locations so that a bladder wall thickness within an expected range is determined. In general, an expected range of bladder wall thicknesses is between approximately about one millimeter and about four millimeters. Accordingly, a search range from about −2 millimeters and about 10 millimeters may be used to search for candidate points on scanlines having large incident angles from the initial front inner wall location. The search range can also be determined based on the volume of urine in the bladder. For a given volume assuming a spherical bladder, we can calculate the minimum and the maximum expected wall thickness based on smallest and largest expected bladder masses. A smallest expected bladder mass value may be around 10 grams while a largest expected bladder mass value may be around 100 grams. Candidate points so identified may be defined as inner layer and outer layer candidate points.

Figure 20:
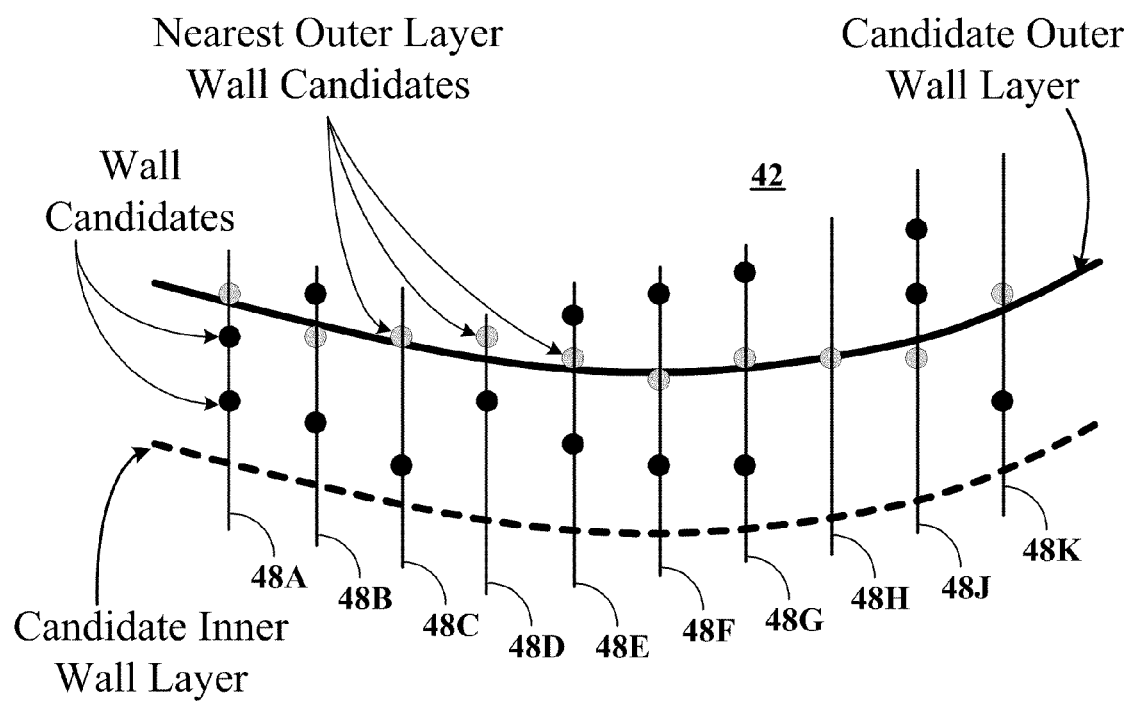
FIG. 20 is a diagrammatic view of a plurality of candidate wall points that result from an echogenic distribution.

FIG. 20 is a diagrammatic view of a plurality of candidate wall points that result from an echogenic distribution, such as the distribution shown in FIG. 19. In FIG. 20, for example, twenty-five wall envelope maxima are identified as candidate points in a relevant portion of the scanplane 42 (FIGS. 8, 15) selected from a series of truncated scanlines 48A through 48K from FIG. 19 that are selected from the scanplane 42. The total number of candidate points may be determined by a candidate points algorithm according to an embodiment of the invention, which will be described in further detail below. The wall layer locations are determined from the segmented front wall (FIG. 20) and the incident angle Ω of a selected scanline 48 (FIG. 15). As shown in FIG. 15, the wall thickness is defined along a surface normal extending outwardly from the front wall of the bladder wall. Alternate embodiments of the methods described for FIG. 16 permits the determination of organ wall thicknesses from non-normal incidence angles.

Of the wall candidate points shown in FIG. 20, nine of the candidate points are determined by the algorithms below to properly characterize a location of the nearest outer layer. The foregoing candidate points are shown in FIG. 20 as lightly shaded circles, while the remaining points, shown as dark circles, are retained as candidate points for an inner layer location determination. As shown in FIG. 20, the nine selected candidate points closely correlate with a candidate outer wall layer. An outer wall selection method algorithm identifies and selects the outer layer points from the plurality of scanlines 48A through 48K. The algorithm reduces the total number of candidate points while preserving appropriate candidate points.

Figure 21A:
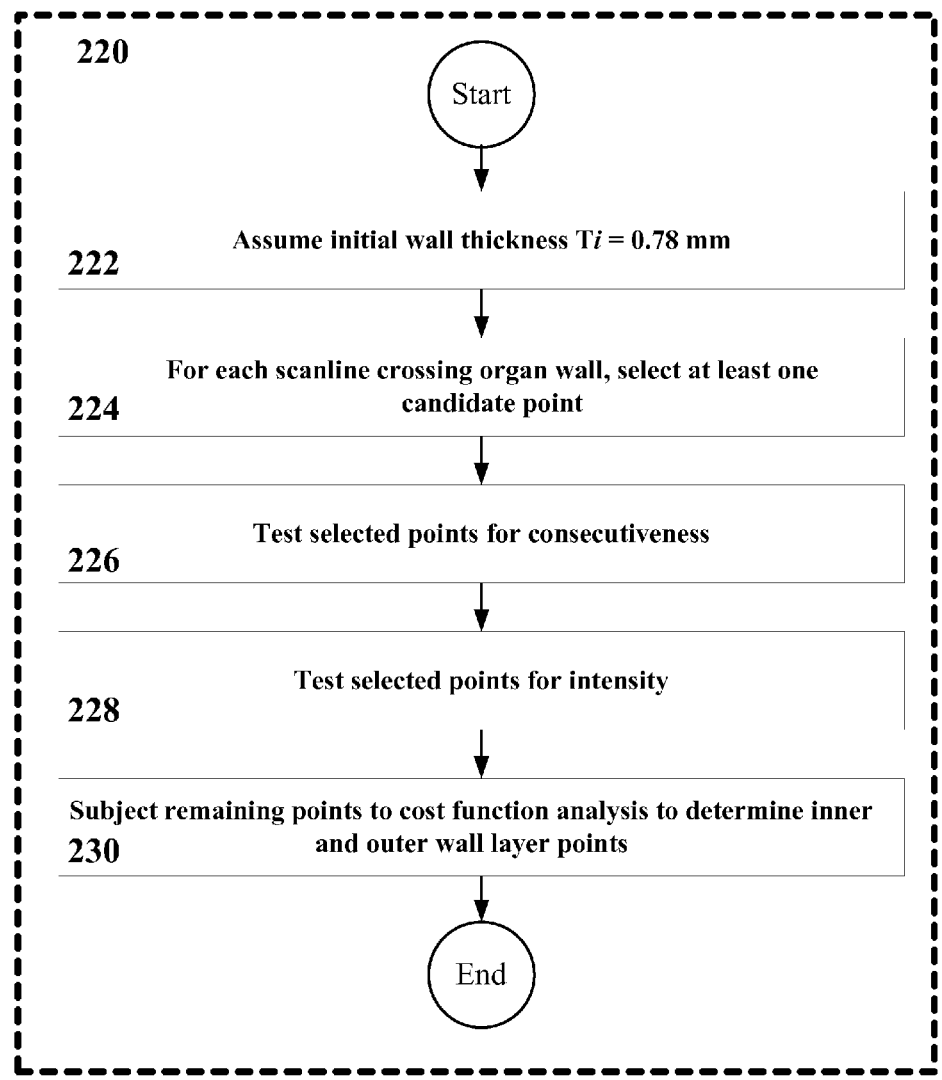
FIG. 21A is a flowchart of a method for identifying an outer wall location according to an embodiment of the invention.

FIG. 21A is a flowchart that will now be used to describe a method 220 for identifying an outer wall location based upon the candidate points, according to an embodiment of the invention. As an initial matter, all candidate points are selected for the analysis described below. In block 222, the outer wall location is first assumed to be at least 0.78 millimeters (mm) away from the inner wall, so that an initial wall thickness is at least about 0.78 mm. Accordingly, the equivalent sample distance is about 0.8 mm (about 20 RF sample points). At block 224, for each of the scanlines 48A through 48K (see FIG. 20), at least one upper most candidate point is selected for each of the respective scanlines 48A through 48K. In one particular embodiment, at least four uppermost candidate points are selected, and characterize the outer wall location, an inside wall location, and a muscular membrane positioned between the outer wall location and the inner wall location. At block 226, the selected candidate points are tested for consecutiveness. Any of the selected candidate points that are more than a predetermined distance away from an assumed inner wall location are rejected. In another particular embodiment, any point candidate point that is more than about 1.2 mm (about 30 RF sample points) away from the assumed inner wall location is discarded. At block 228, of the remaining candidate points, any candidate point having an intensity that is less than about one-half of the intensity among the selected candidates are also rejected. The foregoing blocks in the method are performed for incident angles greater than about 0.2 radian (about 10 degrees). Once the candidate points for the outer wall location have been selected, at block 230, a cost function is employed in order correlate an outer wall location with the candidate points. The cost function is based on the least-square error between the candidate wall locations and the candidate points. The candidate walls are calculated from the known incident angles by varying the wall thickness from 0 to about 78.4 mm. The cost function, Ci, is calculated by the following expression of equation E8:

$$C_i = \left(\frac{1}{n}\sum_{k=1}^{n} \sqrt{\min(|W_k - C|)}\right)^2 \quad \text{E8}$$

Where n is the number of scanlines, $W_k$ is the candidate wall location, and C are the candidate points. An exemplary cost function distribution that characterizes an outer wall location is shown in FIG. 19. Accordingly, an outer wall location is selected by identifying a minimum point in the distribution.

Figure 21B:
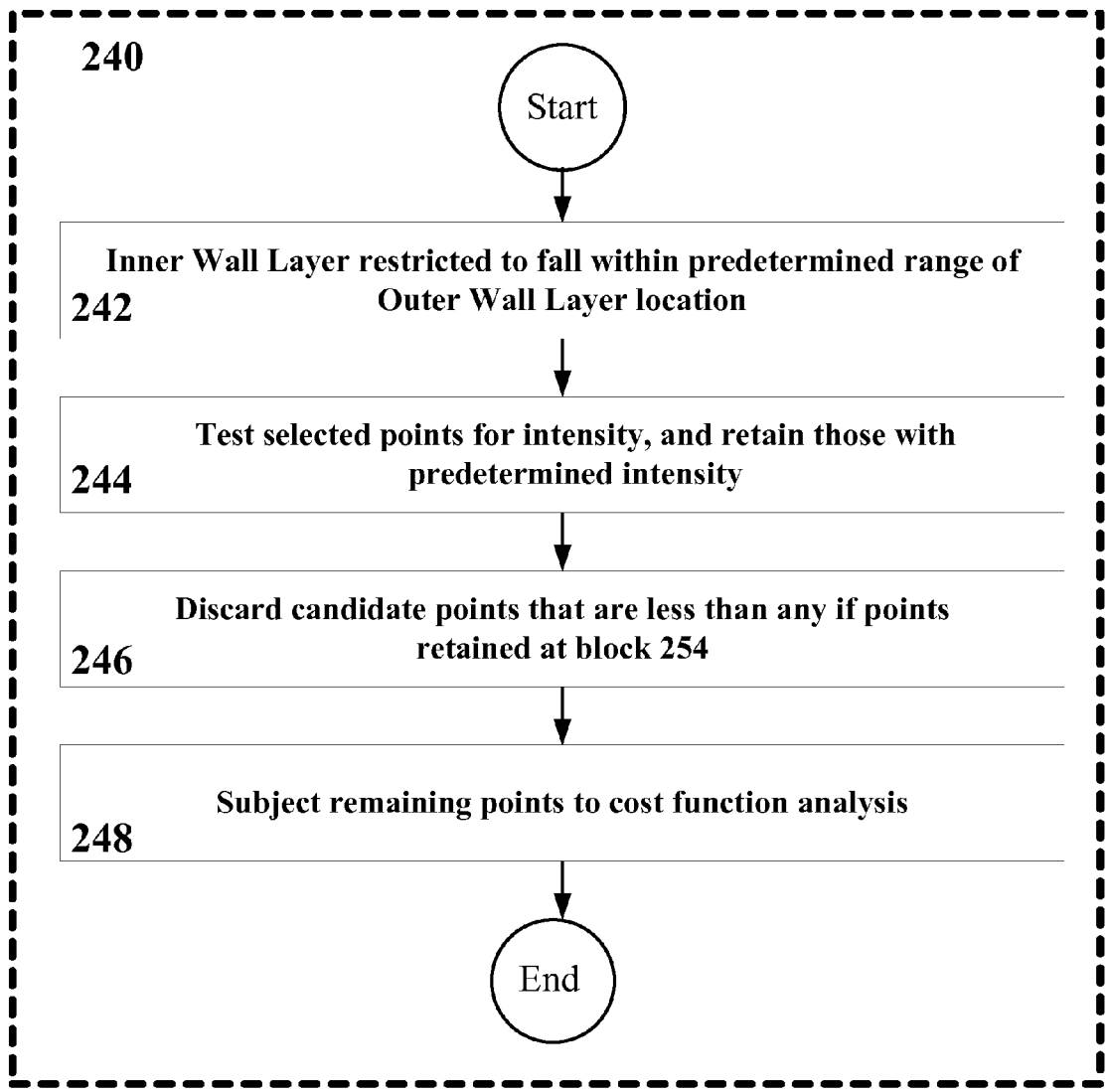
FIG. 21B is a flowchart of a method for identifying an inner wall location according to an embodiment of the invention.

With reference now to FIG. 21B, a flowchart of a method 240 for identifying an inner wall location is shown, in accordance with another embodiment of the invention. At block 242, an inner wall range is restricted to fall within a predetermined range with respect to the outer wall location. In a particular embodiment of the invention, the predetermined range is between approximately about 0.4 mm and approximately about 1.0 mm relative to the outer wall location. At block 244, the intensity of a candidate point is assessed, and if the intensity of the candidate points are greater than approximately about one half of the intensity of a candidate point having a maximum intensity in the inner wall zone, the candidate points are retained. At block 246, if the intensity of a candidate point is less than that of any of the candidate points selected in block 244. During the foregoing inner wall selection, the process is performed only if the incident angle is greater than about 0.2 radian (about 10 degrees). The inner wall location is then selected by reverting to block 248, so that a minimum in cost function distribution may be determined.

Due to acoustic reverberation of the transceiver dome 20 and to additional noise introduced though segmentation, the front wall segmentation of a bodily organ, such as a bladder, may be unacceptable as a thickness measurement estimation. Accordingly, it has been determined that a well-defined wall segmentation may be fitted using a second order polynomial, although other higher order polynomials may be used. The second order polynomial least squares curve fitting will now be described. The segmented points, $y_i$, are known and the second degree polynomial, f(x) is expressed in equation E9 as:

$$f(x) = ax^2 + bx + c \quad \text{E9}$$

The least-square error, Π, may be expressed by equation E10:

$$\Pi = \sum_{i=1}^{n}[y_i - f(x_i)]^2 = \sum_{i=1}^{n}[y_i - (ax_i^2 + bx_i + c)]^2 \quad \text{E10}$$

Π is therefore minimized by varying the coefficient a, b, and c. Consequently, each of the partial derivatives of Π with respect to each coefficient is set to zero, as shown below in equation E11-13:

$$\frac{\partial \Pi}{\partial a} = 2\sum_{i=1}^{n} x_i^2[y_i - (ax_i^2 + bx_i + c)] = 0 \quad \text{E11}$$

$$\frac{\partial \Pi}{\partial b} = 2\sum_{i=1}^{n} x_i[y_i - (ax_i^2 + bx_i + c)] = 0 \quad \text{E12}$$

-continued $$\frac{\partial \Pi}{\partial c} = 2\sum_{i=1}^{n}[y_i - (ax_i^2 + bx_i + c)] = 0 \quad \text{E13}$$

Expanding the above equations, the following expressions are obtained as shown in equation E14-E16:

$$\sum_{i=1}^{n} x_i^2 y_i = a\sum_{i=1}^{n} x_i^4 + b\sum_{i=1}^{n} x_i^3 + c\sum_{i=1}^{n} x_i^2 \quad \text{E14}$$

$$\sum_{i=1}^{n} x_i y_i = a\sum_{i=1}^{n} x_i^3 + b\sum_{i=1}^{n} x_i^2 + c\sum_{i=1}^{n} x_i \quad \text{E15}$$

$$\sum_{i=1}^{n} y_i = a\sum_{i=1}^{n} x_i^2 + b\sum_{i=1}^{n} x_i + c\sum_{i=1}^{n} 1 \quad \text{E16}$$

Expressing the foregoing in matrix form, the following matrix equation is obtained in equation E17:

$$\begin{bmatrix} \sum_{i=1}^{n} x_i^2 y_i \\ \sum_{i=1}^{n} x_i y_i \\ \sum_{i=1}^{n} y_i \end{bmatrix} = \begin{bmatrix} \sum_{i=1}^{n} x_i^4 & \sum_{i=1}^{n} x_i^3 & \sum_{i=1}^{n} x_i^2 \\ \sum_{i=1}^{n} x_i^3 & \sum_{i=1}^{n} x_i^2 & \sum_{i=1}^{n} x_i \\ \sum_{i=1}^{n} x_i^2 & \sum_{i=1}^{n} x_i & \sum_{i=1}^{n} 1 \end{bmatrix} \begin{bmatrix} a \\ b \\ c \end{bmatrix} \quad \text{E17}$$

Therefore, the coefficients a, b, and c for the least squares analysis may be determined as shown in equation E18:

$$\begin{bmatrix} a \\ b \\ c \end{bmatrix} = \begin{bmatrix} \sum_{i=1}^{n} x_i^4 & \sum_{i=1}^{n} x_i^3 & \sum_{i=1}^{n} x_i^2 \\ \sum_{i=1}^{n} x_i^3 & \sum_{i=1}^{n} x_i^2 & \sum_{i=1}^{n} x_i \\ \sum_{i=1}^{n} x_i^2 & \sum_{i=1}^{n} x_i & \sum_{i=1}^{n} 1 \end{bmatrix}^{-1} \begin{bmatrix} \sum_{i=1}^{n} x_i^2 y_i \\ \sum_{i=1}^{n} x_i y_i \\ \sum_{i=1}^{n} y_i \end{bmatrix} \quad \text{E18}$$

If the least-square error between the wall segmentation and the second order polynomial is greater than about five pixels it is rejected from the further processing.

A method for determining a wall thickness, T will now be described. The inner wall location and the outer wall locations previously determined (see FIG. 21A and FIG. 21B) may be used to find the wall thickness by forming a difference between the outer and inner wall locations:

$$T = (\text{Outerwall} - \text{Innerwall}) \cdot \text{RF\_resolution}$$

RF_resolution is the length of a single RF sample, typically but not exclusively 0.08 millimeters. Since a plurality of scancones are developed, during an ultrasound examination, and each scancone has a pair of orthogonal planes having corresponding thickness estimations, a median value may be calculated and accordingly constitutes a best estimate of the wall thickness.

Figure 22:
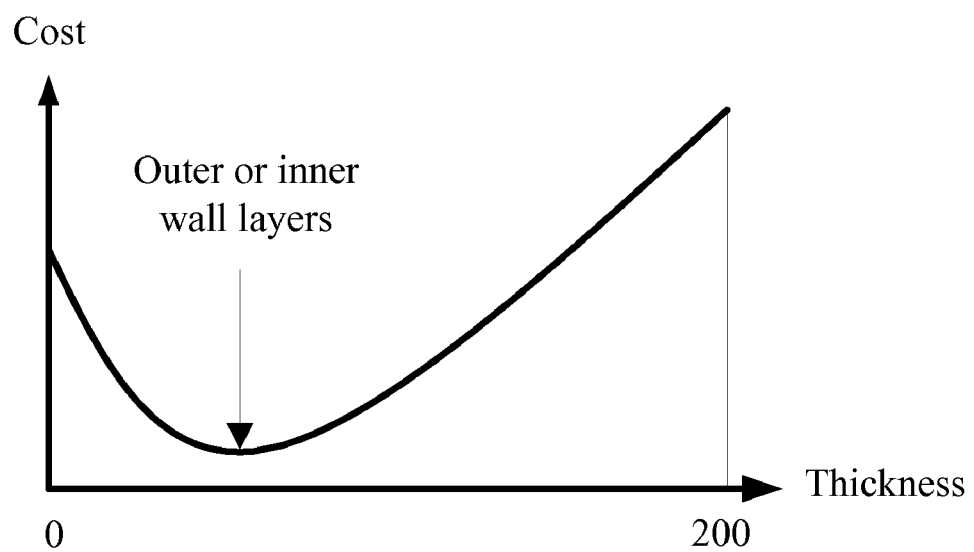
FIG. 22 is an exemplary graph of a cost function generated along a selected scanline.

FIG. 22 is an exemplary graph of a cost function generated along a selected scanline, which was employed in the methods described in FIG. 21A and FIG. 21B. The cost function is thus minimal at a final outer wall layer location exhibiting minimum thickness values. The cost function may therefore be used to identify the minimum thickness value since it is proximate to the minimum cost value.

Figure 23:
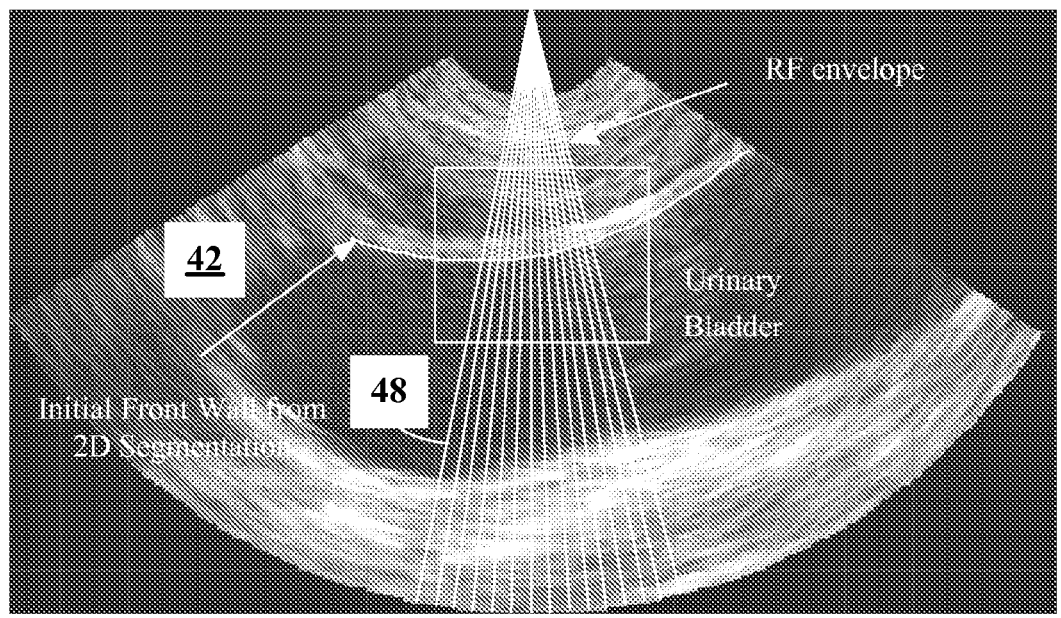
FIG. 23 is an exemplary scanplane of an internal anatomical region having a sector of scanlines superimposed on the scanplane.

FIG. 23 is an exemplary scanplane 42 of an internal anatomical region having a sector of scanlines 48 superimposed on the scanplane 42. The scanlines 48 cross an inner layer border initially determined by the two-dimensional B-mode segmentation algorithms discussed above, in connection with FIGS 14 and 15. The initially determined inner layer border provides a first wall location from which, at the scanline level, a one-dimensional A-mode algorithm may be applied to rectified RF envelopes to determine the nearest outer layer candidates and the nearest inner layer candidates. Either at the scanplane or scanline level, the nearest outer layer candidate points amount to a second wall location. Similarly, the nearest inner layer candidate points amount to a third wall location.

Figure 24:
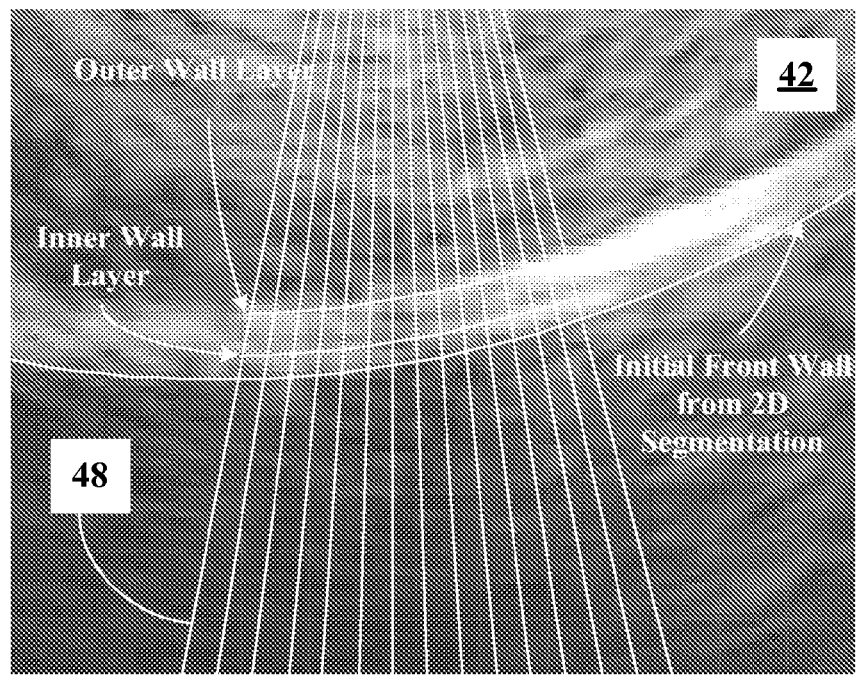
FIG. 24 is an expanded portion of the scanplane 42 of FIG. 23 that shows the initial front wall location in greater detail.

FIG. 24 is an expanded portion of the scanplane 42 of FIG. 23 that shows the initial front wall location in greater detail. The expanded portion of the scanplane 42 shows the outer and inner layer borders of the initial front wall location as determined by the one-dimensional A-mode algorithms with the two-dimensional B-mode inner layer border. Compared with FIG. 19, six of the outer layer candidates were eliminated leaving the nearest outer layer boundary line as shown. The nearest outer layer boundary amounts to the second position loci. Also shown is a nearest inner layer boundary displaced anteriorly to the initial front wall boundary layer as determined from two-dimensional segmentation algorithms.

Figure 25:
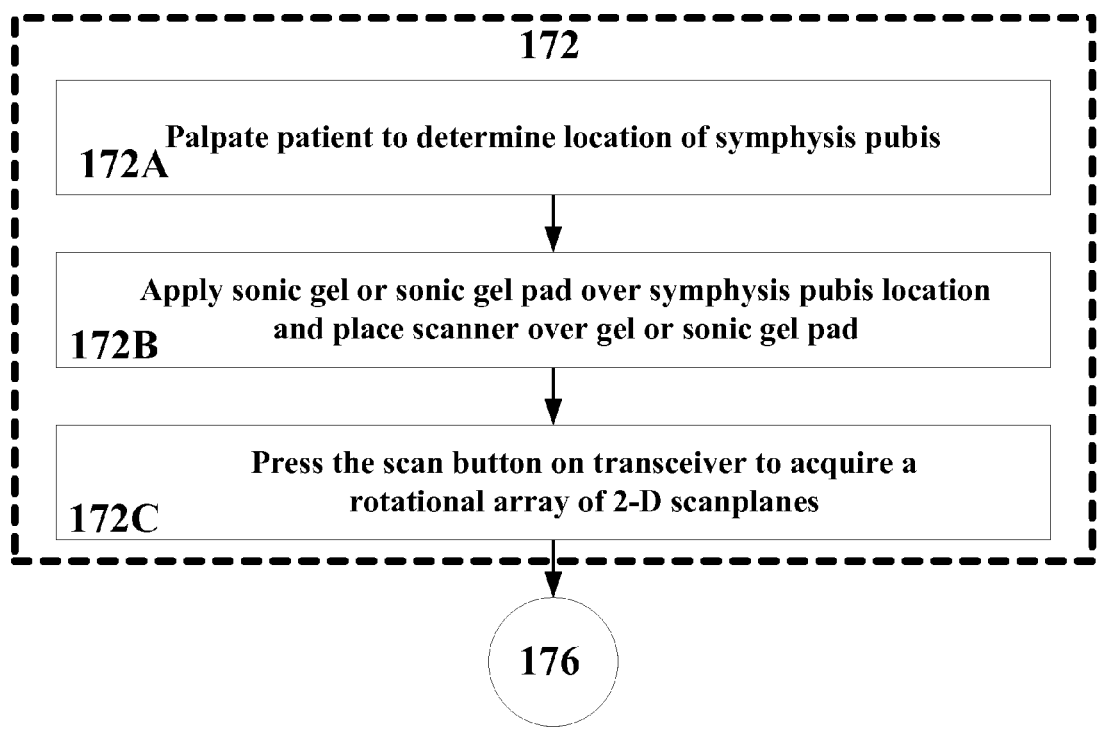
FIG. 25 is an expansion of the sub-algorithm 172 of FIGS. 14 and 15.

FIG. 25 expands sub-algorithm 172 of FIGS. 14 and 15. The sub-algorithm 172 is comprised of three blocks. In block 172A, the patient is palpated to determine the location of the synthesis pubis or as commonly known the pubic bone. Above the synthesis pubis location, a sonic gel pad or a sonic gel is applied and the scanner is either placed in the gel that is applied to the patient or on the sonic gel pad. The sonic gel and the sonic gel pad serve to minimize attenuation of the ultrasound that transverses between the transceiver dome 20 of the transceiver 10 and the patient. The next block is 172C and the scan button is pressed on the transceiver 10 so that a rotational array of 2-D scanplanes is acquired. The method then proceeds to block 176 from FIG. 14.

Figure 26:
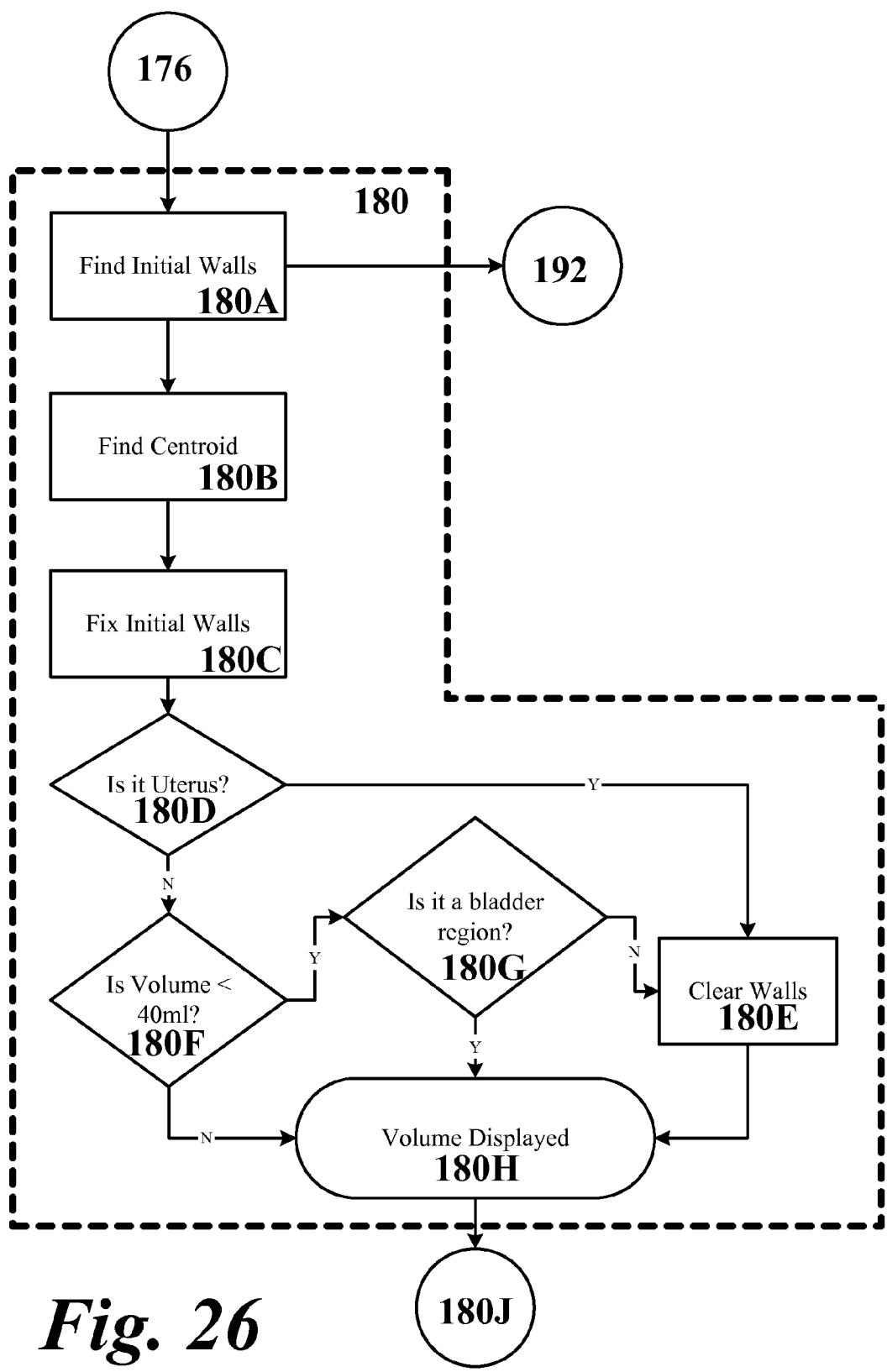
FIG. 26 is an expansion of the sub-algorithm 180 of FIG. 14.

FIG. 26 expands sub-algorithm 180 of FIG. 14. The sub-algorithm 180 is comprised of eight process or decision routines. The first process is block 180A and is called Find Initial Wall. From block 180A is the next block 180B that is Find Centroid. Thereafter, block 180C is Fixed Initial Walls. After Fix Initial Walls is a decision block in which the question is asked, "Is it uterus?" The decision block 180D. If it is a uterus, "yes", the next process is Clear Walls block 180E. Thereafter, the volume is displayed at in process 180H and the process continues on to process 180J. Referring back to decision diamond 180D, if the organ is not a uterus, "no" then we proceed to decision 180F in which the question is asked, "Is volume less than 40 ml.?" If the answer is "no" to the decision diamond 180F, then the volume is displayed at terminator 180H and the algorithm then proceeds to sub-algorithm 180J. If at decision diamond 180F the answer is "yes" to the query, "Is volume less than 40 ml.?" Another decision diamond is presented 180G. At decision diamond 180G, the query is asked, "Is it a bladder region?" If the answer is "no" then the sub-algorithm 180 proceeds to the Clear Walls of block 180E and thence to terminator 180H Volume Displayed. If at the decision diamond 180G, the answer is "yes" to the query, "Is it a bladder region?" then the volume is displayed at terminator 180H and the process then continues on to algorithm 180J. In sub-algorithm 180, an interface line is overweighed on the B-mode scanplane image to approximate an initial location for an organ wall, for example, a uterus or a bladder. This initial interface line is used as a seed or initial reference point in which to further use as a basis to adjust the determination for the inner and outer wall layers of the organ wall. Furthermore, in this algorithm, the detected region in the scanplane is determined to be or not to be a bladder or a uterus. This occurs specifically when the gender button of the transceiver 10 indicates that the scan is for a female. If the regions indeed found to be a uterus, it is cleared and a zero volume is displayed. For a non-uterus region, such as a bladder, if the volume is very small, then checks are made on the size of a signal characteristic inside the detected region to ensure that it is a bladder and not another tissue. If a region is indeed a bladder region it is computed and displayed on the output.

Figure 27:
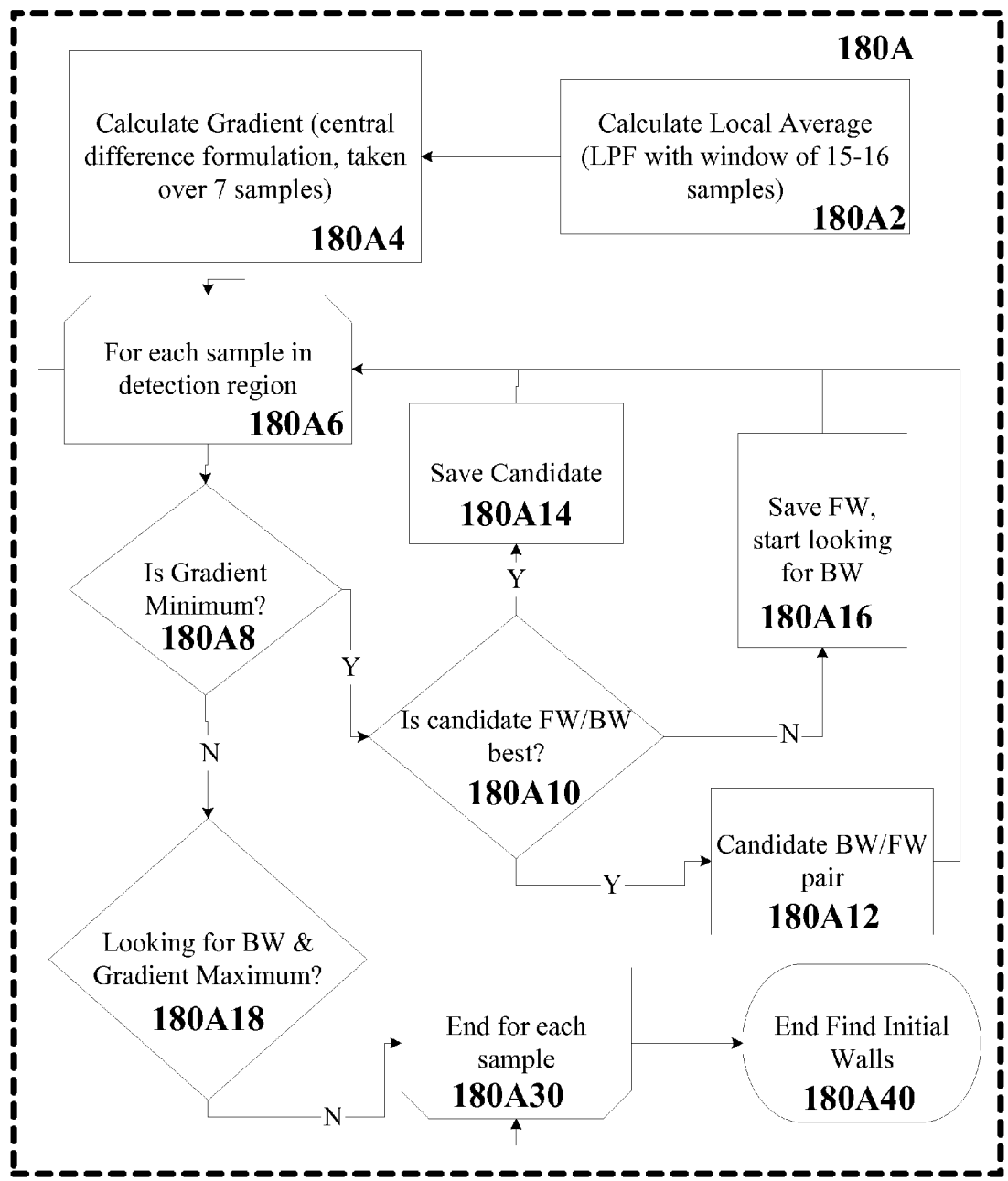
FIG. 27 is an expansion of the sub-algorithm 180A of FIG. 26.

FIG. 27 expands sub-algorithm 180A of FIG. 26. The sub-algorithm 180A is comprised of 11 processes loops, decisions, and terminators. Sub-algorithm 180A begins with process 180A2 in which the Local Average is calculated for the 15 to 16 samples that functions as a low pass filter (LPF) to reduce noise in the signal. Other embodiments allow for calculating averages from less than 15 and more than 16 samples. Next is block 180A4 in which the gradient is calculated using a central difference formulation and has taken over seven sample sets. The process at block 180A4 then proceeds to a beginning loop limit 180A6. In block 180A6, each sample is examined in a detection region. Thereafter, at decision diamond 180A8, the query is, "Is gradient minimum?" If the answer is "no" then another query is presented at decision diamond 180A18, the query being, "Looking for BW and gradient maximum?" BW refers to for back wall. If the answer to the query in block 180A18 is "no" then the end of the loop limit is proceeded to at block 180A30. Thereafter, from the end of the loop limit at 180A30, the terminator end find initial walls is reached at block 180A40. Returning now to the decision diamond 180A8, if the answer to the query, "Is gradient Minimum?" "yes" then another query is presented in decision diamond 180A10. The query in 180A10 is "Is candidate FW/BW best" FW is refers to front wall and BW refers to back wall. If the answer to the query in block 180A10 is "no", then the process 180A62 is used in which the front wall is saved and another back wall is looked for. If the query to in 180A10 is "yes" then the process is Save Candidate occurs at block 180A14. Thereafter, the process returns to beginning loop 180A6 to resume. Returning to the decision diamond 180A10, should the answer be "yes" to the query, "Is candidate FW/BW best, then the process proceeds to block 180A12 in which the candidate is assigned as a pair for back wall/front wall." Thereafter from block 180A12 is returned to the beginning loop 180A6 and then the process will then terminate at end of each sample at end loop 180A30 and thence to terminator 180A40 for end find initial walls sub-algorithm. Sub-algorithm 180A attempts to find the best front wall and back wall pair for the inner and outer wall layer plotting points. The best front wall and back wall pair in each scanline is defined as the front wall and back wall pair for which the difference in the back wall gradient and front wall gradient sometimes referred to as the tissue delta, is the maximum and the smallest local average between the front wall and back wall pair is the minimum for the pixel values.

Figure 28:
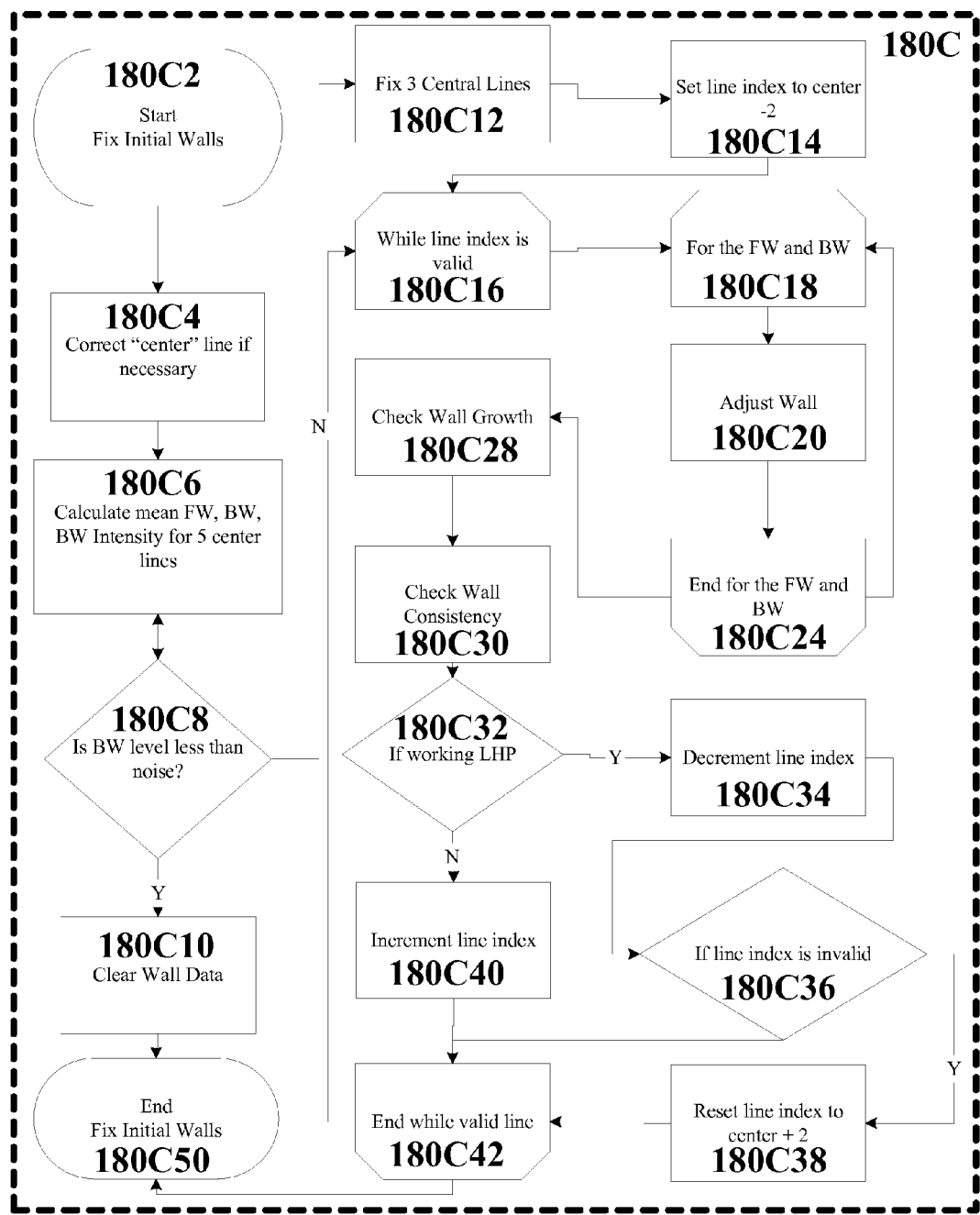
FIG. 28 is an expansion of the sub-algorithm 180C of FIG. 26.

FIG. 28 is an expansion of the sub-algorithm 180C of FIG. 27. Sub-algorithm 180C is comprised of several processes decision diamonds and loops. Sub-algorithm 180C operates on a scanplane by scanplane basis where the first scanplane to be processed is one that is closest to the central aid of the initial walls and then the remaining scanpianes are processed moving in either direction of that initial scanpiane. Sub-algorithm 180C begins at block 180C2 referred to as Start Fix Initial Walls. The first process is at block 180C4 in which the center line is corrected if necessary. The center line is defined as the line on that scanpiane with the maximum gradient difference between the front wall and the back wall. The correction of the front wall and the back wall location at any line is carried out by a match filtering like step where the best location within a search limit is defined as the one for which the difference between points immediately outside the bladder and points immediately inside the bladder is maximum. Of course, this applies to any organ other than the bladder, as the bladder is used here as an example of a particular embodiment. Thereafter, at block 180C6, the front wall and back wall means are calculated for five central lines. The pixel main intensity is computed and if this intensity is less than expected from the noise at that depth, the lines are cleared and the algorithm proceeds to the next plane as shown in decision diamond 180C8 to the query, "Is BW level less than noise?" where BW means the back wall (or posterior wall) of the bladder. If the answer is "yes" to this query, at block 180C10, the process Clear Wall Data is initiated and from that proceeds to terminator 180C50 End Fix Initial Walls. Returning to the decision diamond 180C8, if the answer is "no" to the query, "Is BW level less than noise?" then the sub-algorithm 180C proceeds to the process at block 180C12 described as Fix 3 Central Lines. From this point through the end of sub-algorithm 180C, the purpose is first correct the lines to the left of the central lines, called the left half plane (LHP) until either the edge of the bladder or the edge of the ultrasound cone is found. After the algorithm corrects the LHP, it proceeds to correct the lines to the right of the central lines, called the right half plane. Because the same steps are used for all lines, regardless of their position to the left of center or to the right of center, the process blocks 180C16 through 180C42 are used for both the LHP and once for the right half plane. The "line index" of process 180C14 indicates an identifier for the current line that is processed. The line index is set to 2 indices less than the center line to start processing the LHP. The looping procedure started in block 180C16 continues looping while the line index is a valid index (i.e. it corresponds to a scanline). Sub-loop 180C18 is started with the intent of adjusting the initial wall locations, sub-process 180C20, to their correct location if any correction is necessary. This loop, terminated at process 180C24, completes two iterations. The first iteration uses sub-process 180C20 to correct the front wall of the bladder on the current line and the second iteration to correct the back wall of the bladder, although the ordering of which wall is corrected first can be interchanged. Once the wall locations have been corrected of the current line have been corrected, sub-algorithm 180C proceeds to sub-process 180C28, "Check Wall Growth". This sub-process ensures that the length of the scanline that intersects the bladder in the current line does not grow significantly with respect to the previous line that has already been corrected. In the preferred embodiment, the length of the scanline intersecting the bladder is constrained to be less than 1.125 times longer than in the previous line. If the loop bounded by sub-processes 180C16 and 180C42 is being applied to the LHP, then the previous line is one index number greater than the current line index. Otherwise the previous line index is one index number less than the current index. After completing sub-process 180C28, sub-process 180C30 "Check Wall Consistency" verifies that the portion of the current scanline that intersects the bladder overlaps the portion of the previous scanline that intersects the bladder. After completing sub-process 180C30, decision 180C32 queries "If working LHP?" (i.e. the loop bounded by terminators 180C16 and 180C42 is being applied to the lines left of center). If the answer to the query is yes, then the sub-process 180C34 "Decrement line index" decreases the line index by one index number. Decision 180C36 queries "If line index is invalid". The loop bounded by terminators 180C16 and 180C42 is applied to the next, and now current, scanline. If the decremented line index corresponds to an invalid value, the edge of the LHP has been reached. Sub-process 180C38 is called to reset the line index to the first line to the right of center that has not been adjusted. The loop bounded by terminators 180C16 and 180C42 will now be applied to the right half plane (RHP). Returning to decision 180C32, if the answer to the query is "No", sub-process 180C40 "Increment line index" results with the line index being increased by one index number. Loop terminator 180C42 cause the loop to return to 180C16 as long as the line index corresponds to an actual scanline. As soon as that condition is violated, the loop terminator will cause sub-algorithm 180C to proceed to the terminator 180C50, "End Fix Initial Walls".

Figure 29:
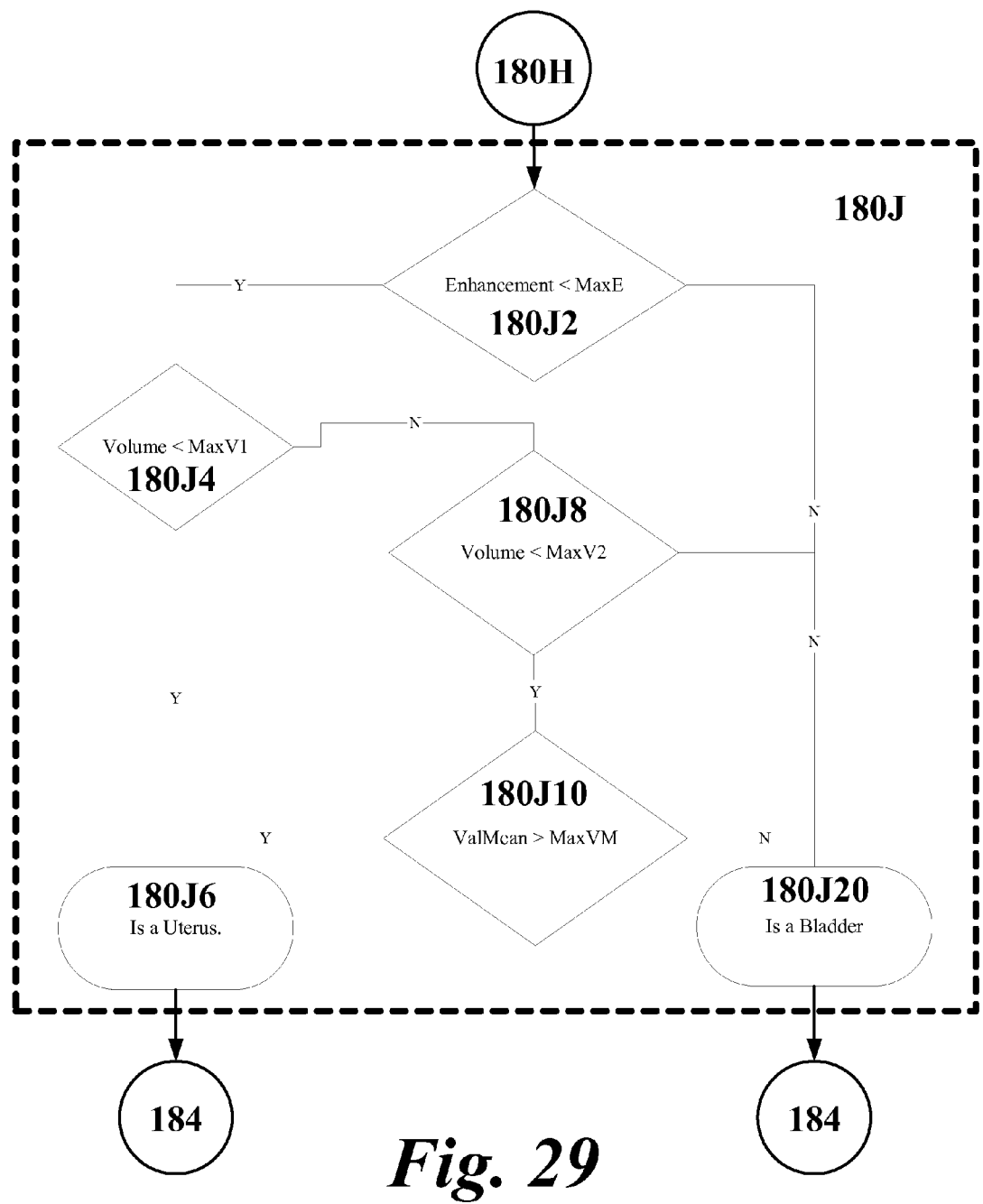
FIG. 29 is an expansion of the sub-algorithm 180J of FIG. 26.

FIG. 29 is an expansion of the sub-algorithm 180J of FIG. 26. The procedures within sub-algorithm 180J provide a decision tree used for ascertaining whether a uterus has been detected. The definitions of the abbreviations in the flow chart blocks are Max E, Max V1, Max V2, ValMean, and MaxVM. Max means maximum, E means enhancement, V1 means volume 1, V2 means volume 2, ValMean refers to a measurement of the minimum local average pixel intensity of the region inside the region identified as urine inside the bladder, Max VM is a pre-defined threshold against which VALMEAN is tested. If VALMEAN is greater than MAXVM, the region identified as urine inside the bladder isn't really urine and the boundaries are actually an outline of the uterus. Depending on the hardware platform used for the various embodiments of the transceiver 10, the decision tree for the sub-algorithm 180J of FIG. 26. The sub-algorithm 180J begins from sub-algorithm 180H in which a decision diamond Enhancement<MaxE (maximum enhancement) at decision diamond 180J2 is reached. If the answer is "yes" for enhancement, then another decision diamond 180J4 is reached and the query is a Volume<Max V1 (maximum Volume 1) is made. If the answer is "yes" to this query, then the determination at terminator 180J6 is reached and the organ that is being examined is a uterus. Thereafter, the algorithm continues to block 184 of FIG. 14. Returning to the decision diamond 180J4, if the answer is "no" to the query Volume<Max V1, then another decision diamond 180J8 is reached having the query "Is the Volume<Max V2?" (Maximum Volume 2). If the answer is "yes", then the next decision diamond is 180J10 is reached with the query, "Is the ValMean>MaxVM?" If the answer is "yes", then terminus 180J6 is reached and the organ being viewed is the uterus. If the answer is "no", then terminus 180J20 is reached and the organ being viewed is a bladder, the algorithm then completes block 184 of FIG. 14. Returning back to decision diamond 180J8, if the answer is "no" to the query, "Is the volume<than MaxV2", then the answer is that a bladder is being viewed as indicated by the terminal 180J20." From terminus 180J20 the algorithm continues to block 184 of FIG. 14.

Figure 30:
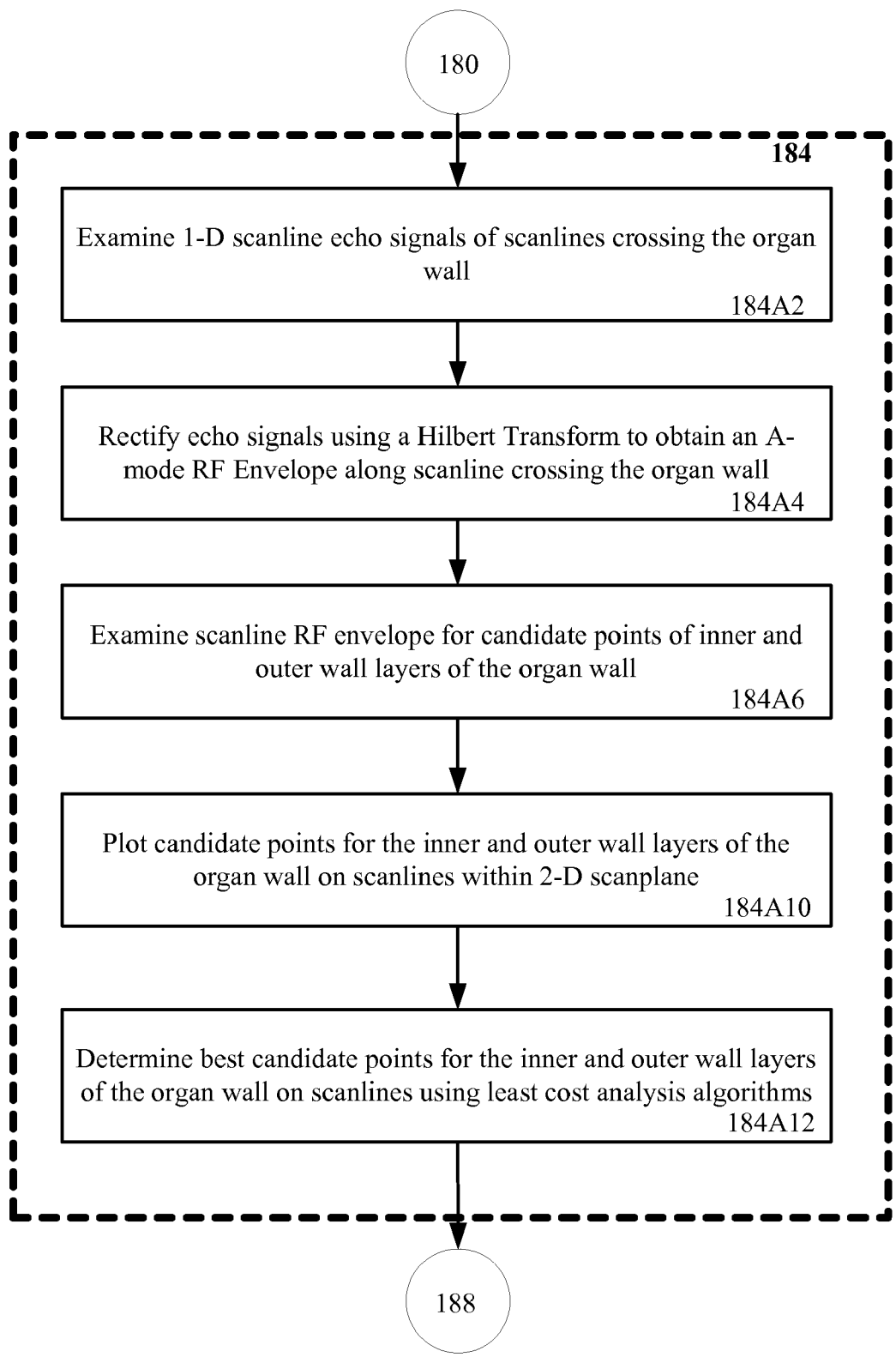
FIG. 30 is an expansion of the sub-algorithm 184 of FIG. 14.

FIG. 30 is an expansion of an alternate embodiment of the sub-algorithm 184 of FIG. 14. The processes within sub-algorithm 184 are procedures taken between blocks 180 and 188 of FIG. 31. The sub-algorithm 184 is comprised of block 184A2 in which 1-D scanline signals are examined for scanlines crossing the organ wall. Thereafter at block 184A4, the echo signals are rectified using a Hubert Transform to obtain an A-mode radio frequency (RF) envelope along scanlines crossing the organ wall. Sub-algorithm 184 continues with block 184A6 where the scanline RF envelope is examined for candidate points of inner and outer wall layers of the organ wall. Thereafter at block 184A10 the candidate points are plotted for the inner and outer wall layers of the organ wall on scanlines within the 2-D scanplanes. Finally, the sub-algorithm 184 is completed with the process described at block 184A12 in which the best candidate points are determined for the inner and outer wall layers of the organ wall being examined on scanlines using a least cost analysis algorithm previously described above.

Figure 31:
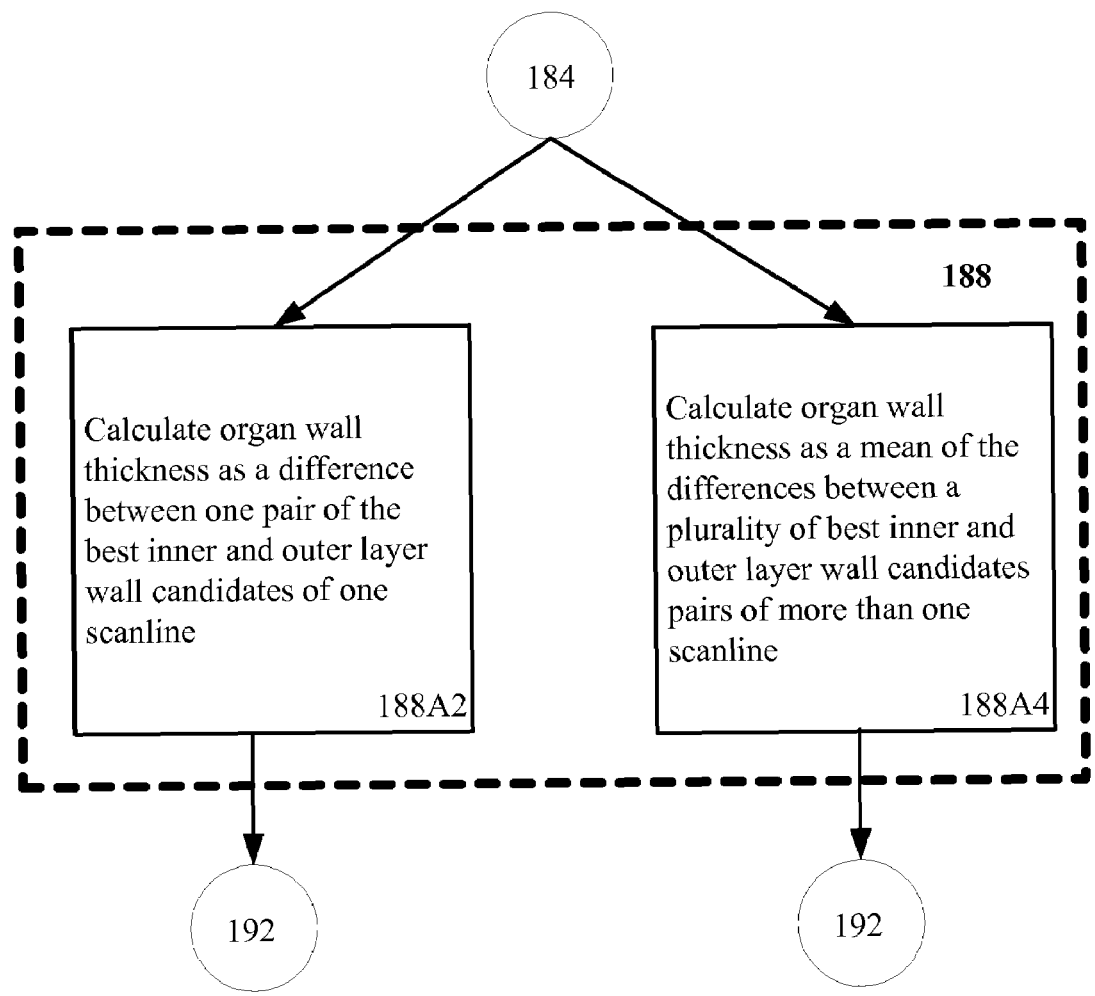
FIG. 31 is an expansion of the sub-algorithm 188 of FIG. 14.

FIG. 31 is an expansion of the sub-algorithm 188 of FIG. 14. Sub-algorithm block 188 is between sub-algorithms 184 and 192 of FIG. 14. There are two sub processes in 188 depending upon how the organ wall thickness is calculated depending upon either a single value or a group of values. For a single value at block 188A2, the organ wall thickness is calculated as a difference between one pair of best inner and outer layer wall candidates from one scanline. Alternatively, at block 188A4, the organ wall thickness is calculated as a mean of the differences between a plurality of best inner and outer wall layer candidates pairs of more than one scanline crossing the organ. Both blocks 188A2 and 188A4 are then continued to sub-algorithm 192.

Figure 32:
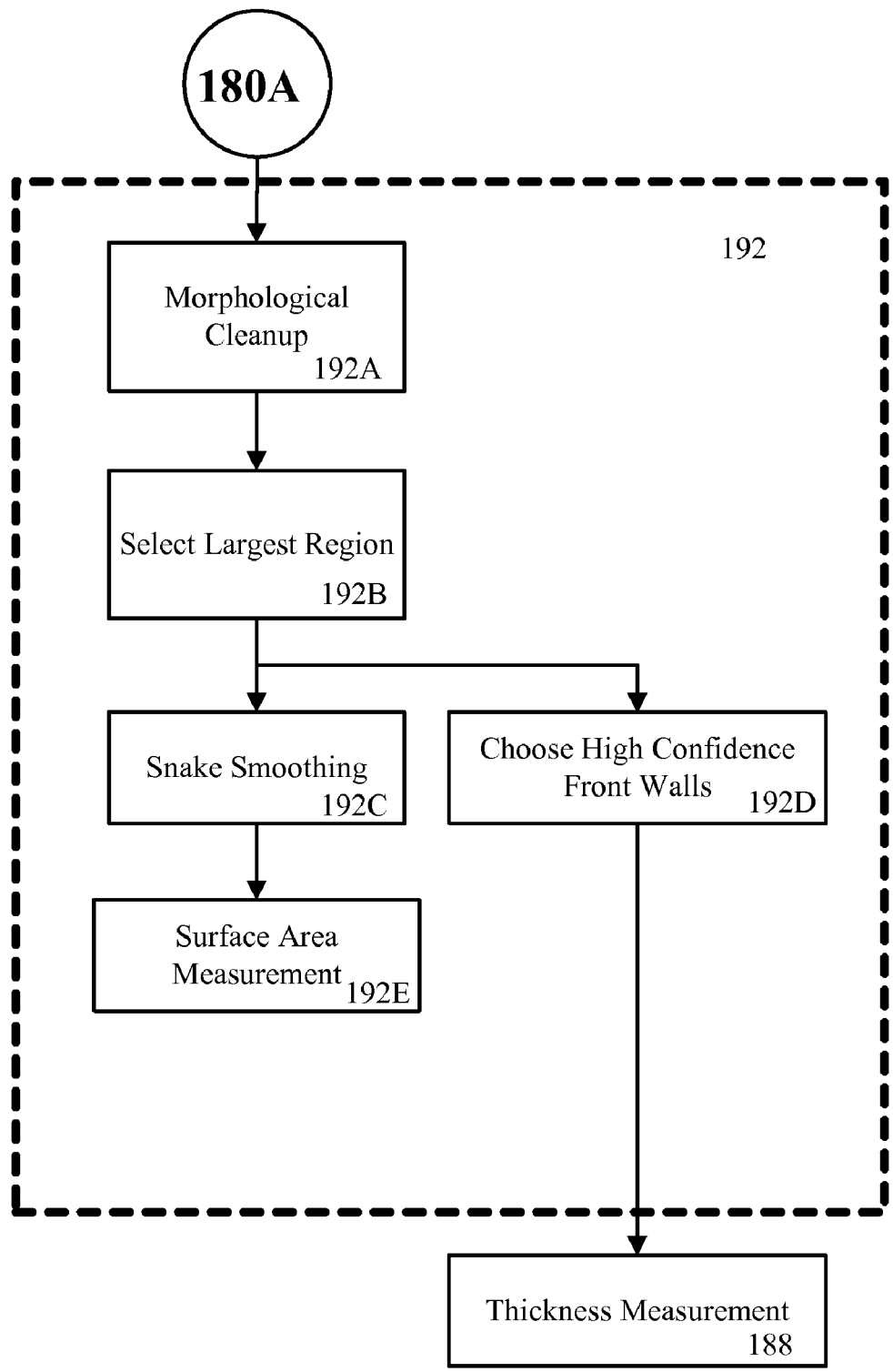
FIG. 32 is an expansion of the sub-algorithm 192 of FIG. 31.

FIG. 32 is an expansion of the sub-algorithm 192 of FIG. 31. Sub-algorithm 192 is between sub-algorithm 180A and thickness measurement 188. Sub-algorithm 192 starts with block 192A morphological cleanup. The processes of sub-algorithm 192 identifies potential front wall and back wall pairs on A-mode scanlines that potentially look like an organ of interest, for example, a bladder in which a dark region which is surrounded by bright echos on the front and of the back of the organ being viewed. The sub-algorithm 192 uses some shape and anatomical knowledge to clean up the potential front walls and back walls in the morphological cleanup block 192A. The morphological cleanup is needed because there may be missing wall pairs that appear spurious and further more are further obscured by speckle and other noise associated with ultrasound-based images. Such a speckle and other ultrasound-based noise may give a front and back walls that are unnecessarily jagged. The morphological cleanup at block 192A serves for correcting errors due to this jaggedness and for regularizing or smoothing these wall locations. The morphological cleanup block 192A uses mathematical morphology and a sequence of morphological operations that are applied to the initial wall data. The mathematical operations will be described in figures below. After execution of the morphological cleanup process at block 192A, there may be more than one potential region that represents an organ of interest say the bladder. If there is more than one region, then the largest three-dimensional region is assumed to be the bladder and is selected for further processing. This selection of the largest region occurs at the next block 192B. After the largest region selection is determined, another smoothing and cleanup process is applied at block 192C mainly a process referred to as snake smoothing. A variant of the snake-smoothing algorithm was developed and is described in the figures below. The boundary output from this snake smoothing algorithm step 192C is used to calculate the surface area of the bladder using an algorithm described below. The initial points that are used in sub-algorithm 192 are those that were already obtained to have high confidence. Those that were not high confidence wall points are filtered and removed. The high confidence front wall locations are then used to initialize the RF base thickness measurement as described above and as further elucidated below. Parallel with the snake smoothing algorithm 192C, a block 192D is implemented in which high confidence front walls are selected or chosen. After snake smoothing has been implemented at block 192E surface area measurement is then conducted.

Figure 33:
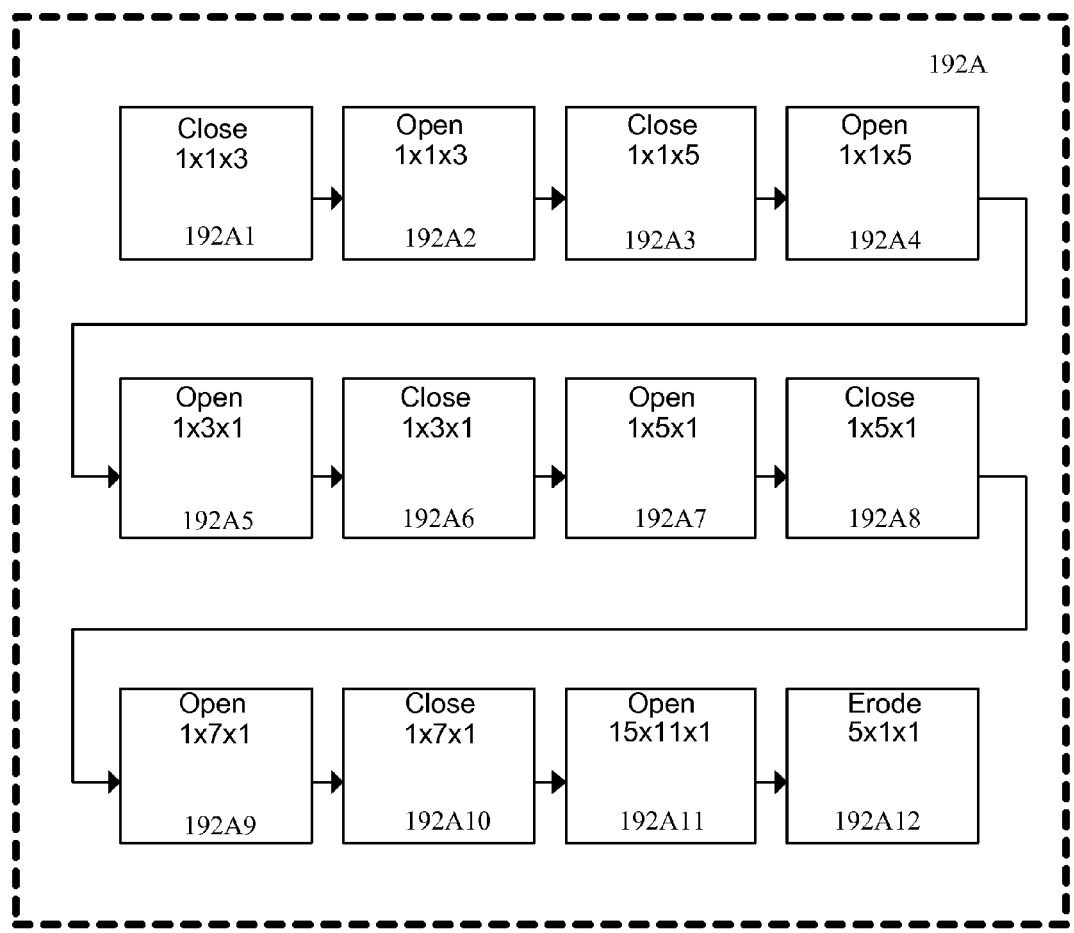
FIG. 33 is an expansion of the sub-algorithm 192A of FIG. 32.

FIG. 33 is an expansion of the sub-algorithm 192A of FIG. 32. Several steps are applied to initial wall data. A series of morphological openings and closings are used with increasingly large kernel sizes and are applied to the pre-scan converted data. This kind of filter is known as "alternating sequential filter" and further described in P. Soille and J. F. Rivest, *Principles and Applications of Morphological Image Analysis*. In the expansion of sub-algorithm 192A, gaps are filled between planes and the image sequence. As an example, the sub-algorithm 192A is represented by a series of close and open processes that are shown in eleven process boxes and conclude with an erode box. The first close process box is 192A1 which then proceeds to a first open process box 192A2 and further proceeds to the following series described below. The series of morphological openings and closings are used with increasingly large kernel sizes and are applied to the pre-scan converted data. The first operation is a closing with a structuring element 3 planes deep designated in block 192A1 as 1×1×3. This step fills in the gaps between planes that extend to less than 3 planes. Next, in open block 192A2, a structuring element 3 planes deep is opened which removes outlier regions between the planes that extend for less than 3 planes. Thereafter, at block 192A3, the data is closed in a 1×1×5 sequence and then reopened at block 192A4 in a 1×1×5 sequence. That is the structuring elements of 5 planes deep in blocks 192A3 and 192A4. The open and close algorithm continues with open block 192A5 and close block 192A6 in which this series of morphological operations aim to fill gaps and remove outliers within a plane. In open block 192A5, a small opening using a structure element 3 scanlines wide is implemented and this serves to remove outliers that are less than 3 scanlines wide. This step is then followed by block 192A6 in which a closing process is implemented that closes all gaps in the wall locations less than 3 scanlines wide. Thereafter, another open and close pair of processes are applied at open block 192A7 and close block 192A8. The open block 192A7 is of a 1×5×1 configuration and the close processing block 192A8 is of a 1×5×1 operation. Thereafter, an open and close processing is done in a 1×7×1 configuration at block 192A9 and block 192a10, respectively. In these two blocks, outliers are removed and gaps are filled for 5 and 7 scanlines, respectively. Thereafter, at open processing block 192A11, a 15×11×1 configuration is implemented in which 15 samples long and 11 scanlines wide are processed to help select for the proper points. In open block 192A11, the main purpose is to remove erroneous front wall locations that are affected by the dome reverberation artifact dissociated with ultrasound echo reverberations of the dome 20 if the transducer 10. The final step of sub-algorithm 192A is an erode processing block 192A12 in which the morphological processing erodes the front and back walls by 5 samples. That is, this is a 5×1×1 configuration in which the step shrinks the front walls and the back walls inside to allow the snake to expand and search for the best location.

Figure 34:
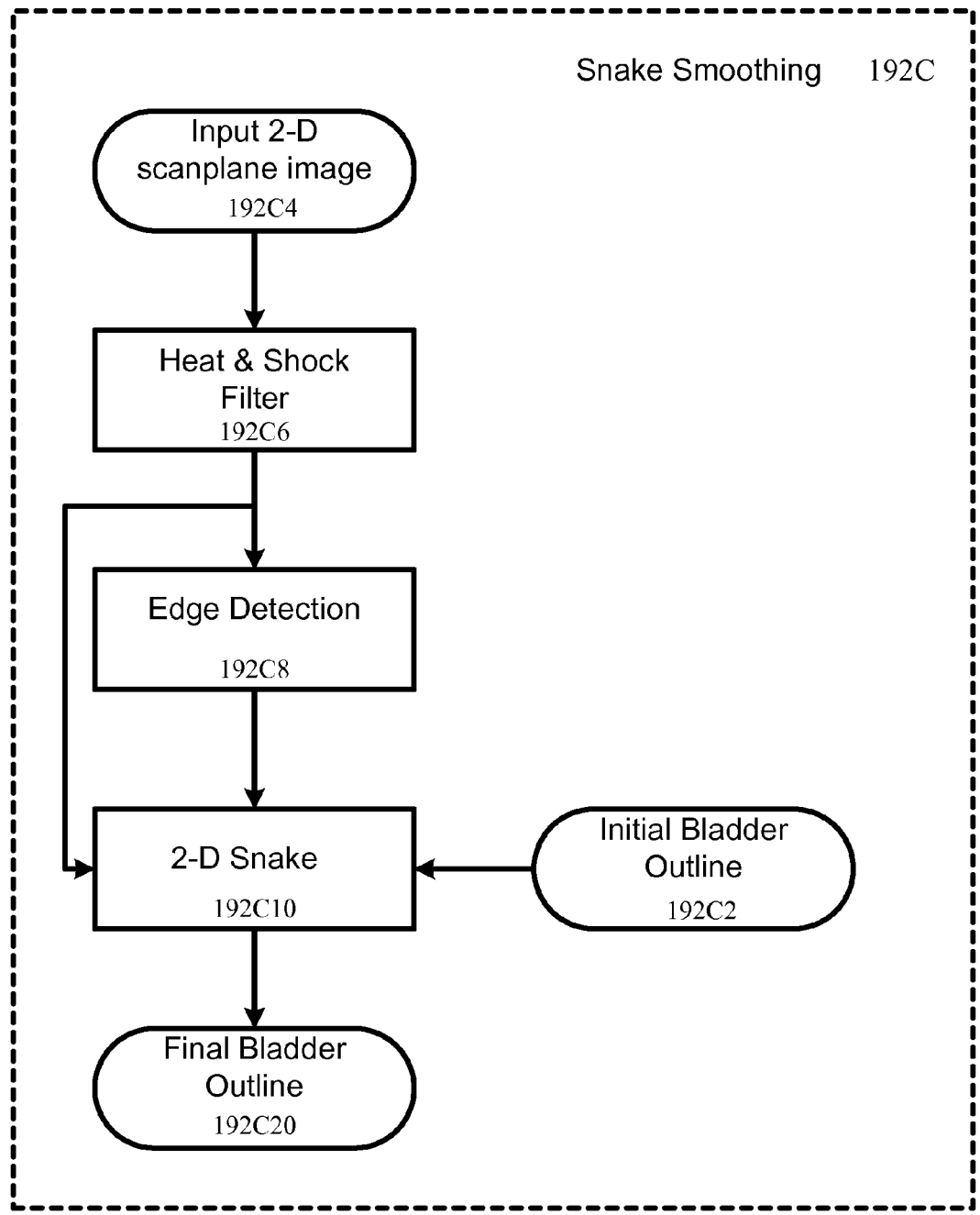
FIG. 34 is an expansion of the sub-algorithm 192C of FIG. 32.

FIG. 34 expands sub-algorithm 192C of FIG. 32. Sub-algorithm 192C is for snake smoothing and is comprised of several processing and terminator steps. Snake processing uses an active contour known as a snake and is basically a way to link edges or other image features by minimizing a cost function for a contour passing through the image features. The cost function typically includes a cost that favors contours that are close to the desired image features on the image and a cost that favors smooth and short contours.

The minimum cost contour is found by using an iterative method starting with an initial contour that is fairly close to the desired contour. This initial contour is minimized iteratively and the motion of the contour between iterations resembles the motion of a snake; therefore the name of the algorithm. The snake moves under two forces—(1) an image-based force that tries to move the contour closer to image edges, and (2) a regularizing force that tries to make the contour smooth and short. At the end of the iterations, a contour is developed which balances the two forces using the following sub-algorithms of snake smoothing algorithm 192C of FIGS. 32 and 34.

A combination of two images is used to define image-based forces. The first image is a gray scale image that is inputted at starting terminus 192C4. Thereafter, a heat and shock filter at block 192C6 is applied which respectfully serve to optimize a detection of the gray scale image. The two images are incorporated into the snake metric using the following logic. Looking along a direction normal to the snake curve, the optimal snake location has the maximum difference between the gray scale intensities outside the curve and the gray scale intensities inside the curve and it lies on a location that is identified as an edge point. This occurs at the edge detection process block 192C8. After heat and shock filtration at block 192C6 and after edge detection at 192C8, a 2-D snake algorithm is applied as described further in block 192C10 of FIG. 34. At 192C10, an initial bladder outline or other organ of interest outlined is provided to processing block 192C10. The initial bladder outline is inputted from input terminal 192C2. After application of the 2-D snake process 190C10 to the input 2-D scanplane image of 192C4, an overlay with initial bladder outline of 192C2, a final bladder outline is generated at terminus 192C20. Discussing below an amplification of the 2-D snake algorithm 192C10 is further described.

Figure 35:
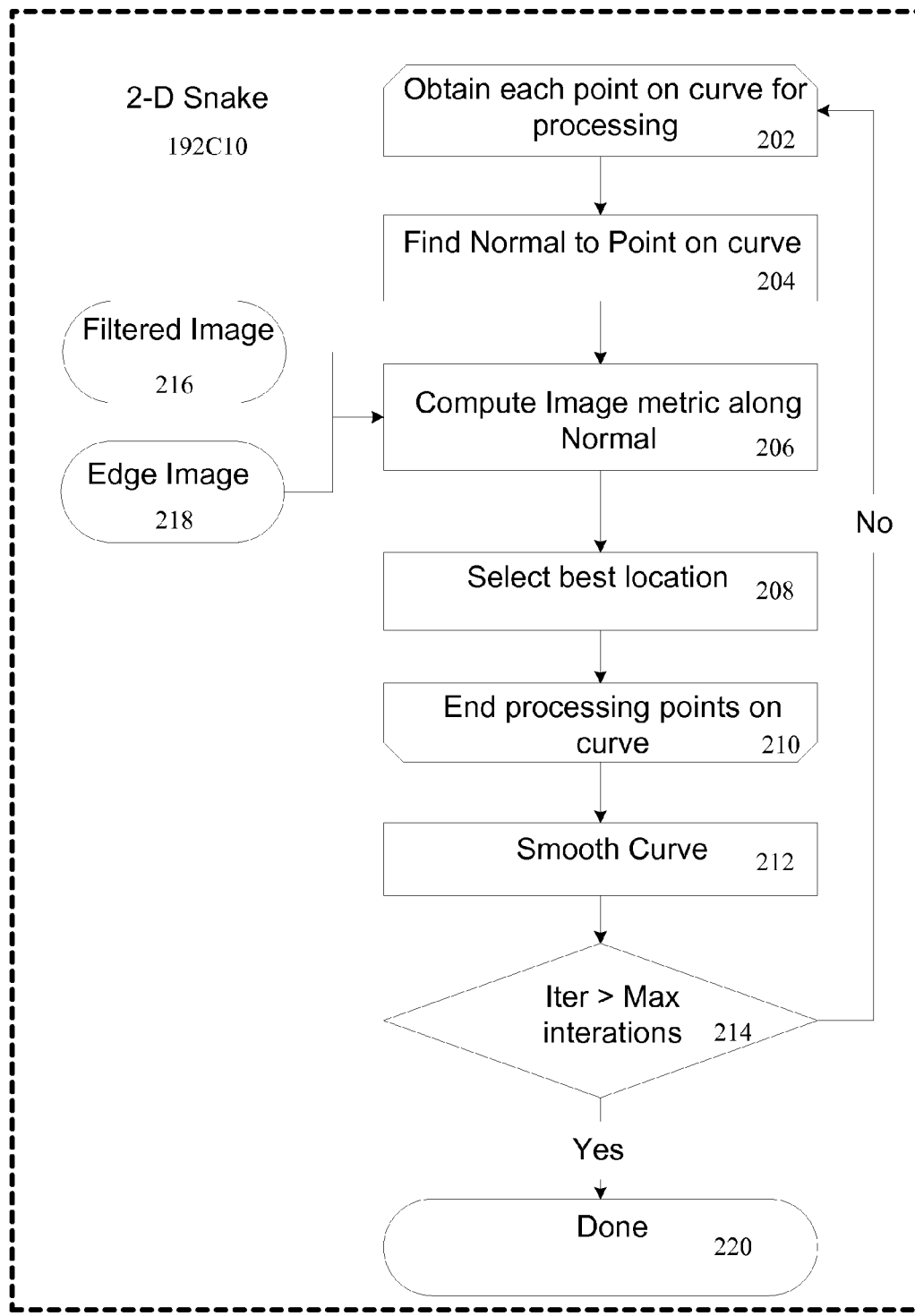
FIG. 35 is an expansion of the sub-algorithm 192C10 of FIG. 34.

FIG. 35 expands sub-algorithm 192C10 of FIG. 34. The expansion of this algorithm serves to make the snake an iterative sequence of the following two steps—(a) moving the contour in a direction normal to the contour where each normal direction that is searched becomes the best image metric, and (b) smoothing the deformed contour using regularization constraints. In the application of the sub-algorithm, each point along the curve is examined and image pixels are sampled normal to each point and the image metric is calculated at each normal location within a pre-specified search range. Thus, beginning at the loop at 202, each point of the curve is readied for processing. Thereafter at processing block 204 a normal to the point on the curve is found. Thereafter at block 206, a normal to the image metric is computed provided that filtered images from block 216 and edge image 218 are available. The image metric at each point uses the gray scale pixel intensities inside and outputs the curve and also uses the edge image obtained respectfully from the filtered image block 216 and edge image block 218. The contour point is moved to a location where the image metric is optimal, i.e., the gray scale intensity difference is maximal and the location corresponds to an edge location. This is denoted in block 208 selected best location. Thereafter, the processing loop is ended at block 210 and the processing points on the curve is completed. Next is a smoothing of a contour that is carried out at block 212, smooth curve. Of the contour, it is carried out by multiplying the vectors representing the X and Y coordinance of the contour with a smoothing matrix. Following the smooth curve 212 block is a decision diamond for the termination of the Max iterations has been reached and if it has, then the 2-D snake algorithm 192C10 is completed at terminus 220. If it has not, the procedure returns to the opening loop 202 of the sub-algorithm. Referring now to the filtered image block 216 of the edge image block 218, the snake algorithm are applied to obtain the best computed image metric along the normal block 206 based upon examining every detected front wall layer location within a small search region on the same scanline around the detected front wall layer location. If no edges are found within the search area, the wall location is considered of low confidence and is removed from the output wall locations. However, if an edge point exists within that search region, and the intensity difference between the pixels outside and inside the organ wall, for example, a bladder wall on an enhanced image is maximal, the location is considered a high confidence location. The output wall location for such a point is moved to this high confidence location.

Figure 36:
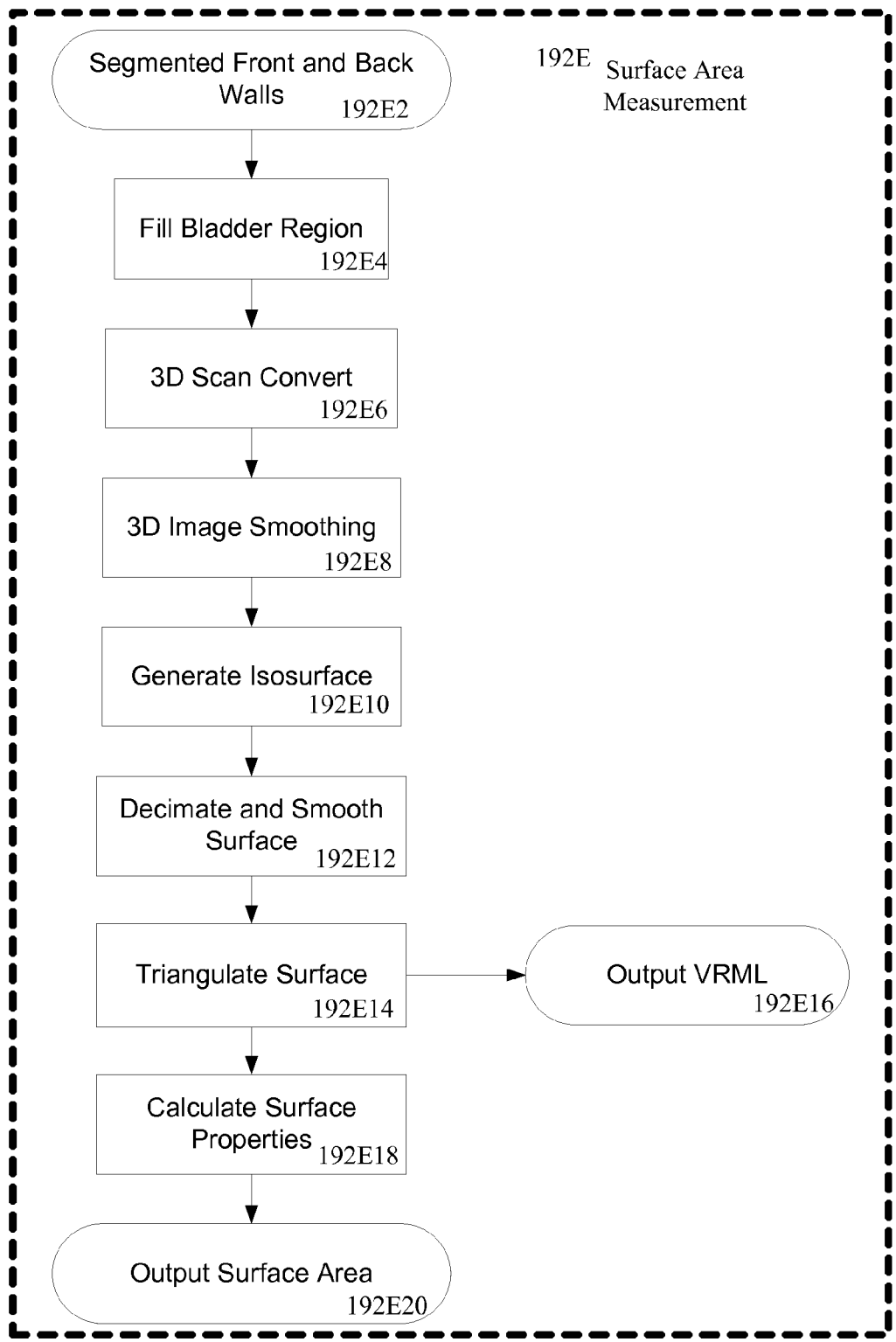
FIG. 36 is an expansion of the sub-algorithm 192E of FIG. 32.

FIG. 36 expands sub-algorithm 192E of FIG. 32. Sub-algorithm 192E concerns the procedures for obtaining a surface area measurement and comprises a series of processing steps. Starting with block 192E2, the segmented front and back walls are supplied to a fill bladder region procedure in block 192E4. The fill bladder region procedure creates a pre-scan converted, for example, in polar coordinate form, volume where all the pixels inside the bladder are filled in with a non-zero pixel value such as 255. Then all the pixels outside are set to zero. The next procedure is in block 192E6, a 3-D scan convert process. The 3-D scan convert process is a conversion procedure applied to convert the polar coordinate pre-scan image to a Cartesian coordinate system. The size of the Cartesian volume created is 150×150×150. This Cartesian volume data is then smoothed as indicated in block 192E8 3-D image smoothing. The smoothing step uses a Gaussian smoothing window of approximately 11×11×11 pixels. The kind of filtering used in the Gaussian smoothing is preferable to generate a smooth output organ surface as would be for a bladder surface. In the next block 192E10, a general iso-surface procedure is implemented. The general iso-surface procedure uses the Marching Cubes algorithm described in Lorensen and Cline (W. E. Lorensen and H. E. Cline, "Marching Cubes: A High Resolution 3D Surface Construction Algorithm," *Computer Graphics*, vol. 21, pp. 163-169, July 1987.) Marching Cubes algorithm is applied to create iso-surface of the organ region such as a bladder. An iso-value of 127.5 is used to decide where to place the iso-surface on the smooth image. Everything greater than this iso-value of 127.5 is considered inside the bladder or the organ of interest and less than this value is considered outside the bladder or organ of interest. In the next step process 192E12, the organ surface is then decimated and smoothed to reduce the number of vertices. The surface is then triangulated at process step 192E14 in order to represent the entire surface using a mesh of triangles. This triangulated surface is then outputted as a VRML for potential display and is also used for the calculation and surface area and other properties. The triangulated surface is used for surface area calculation. As shown in the FIG. 36, the triangulated surface is also output as a VRML file in terminus 192E16. The surface properties, surface area, etc. are calculated as indicated in block 192E18. Thereafter, at terminus 192E20, the surface area is outputted for report.

Figure 37A:
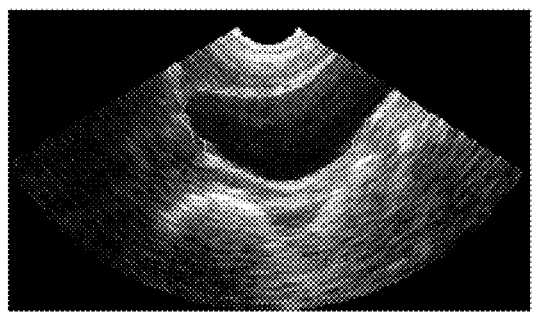
FIGS. 37A-D are B-mode scans overlaid with interface tracings.
Figure 37B:
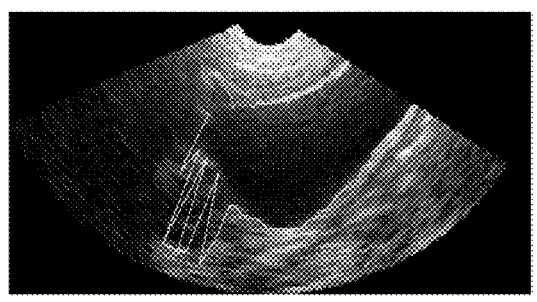
Figure 37C:
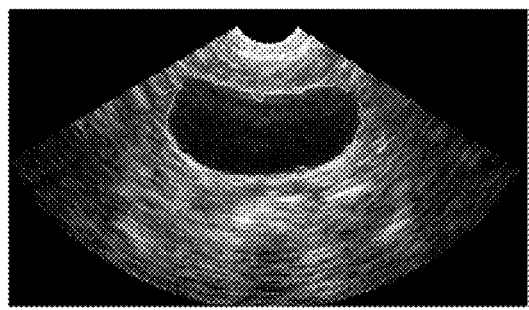
Figure 37D:
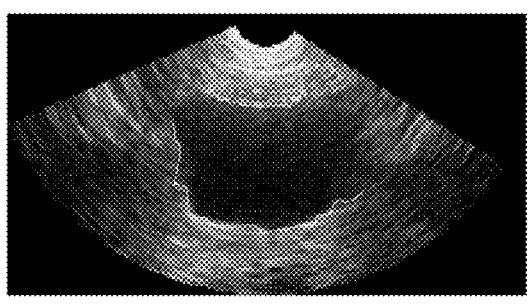
Figure 38A:
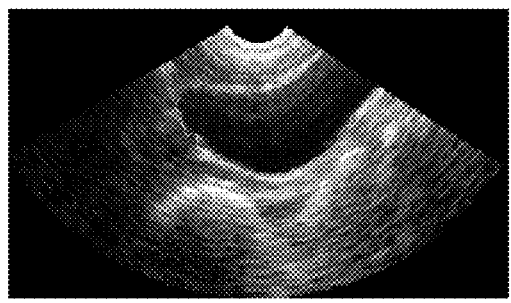
FIGS. 38A-D are B-mode scans overlaid with interface tracings.
Figure 38B:
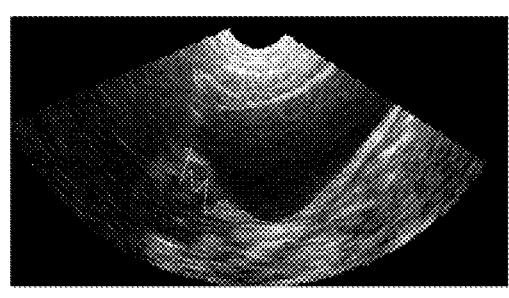
Figure 38C:
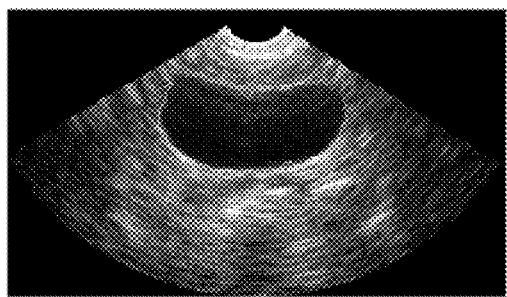
Figure 38D:
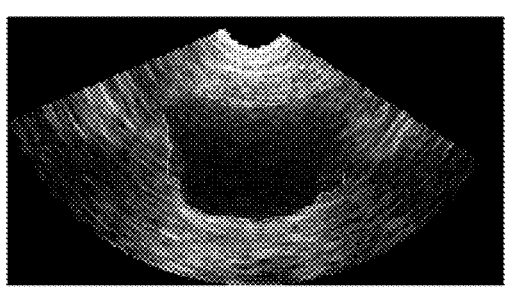
Figure 39A:
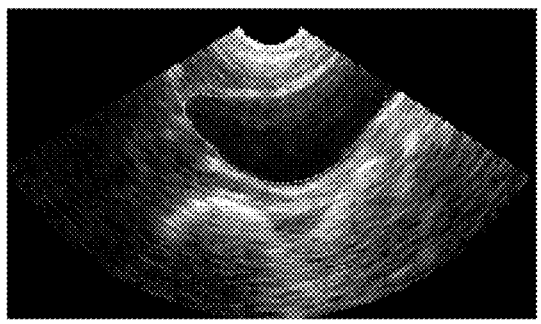
FIGS. 39A-D are B-mode scans overlaid with interface tracings.
Figure 39B:
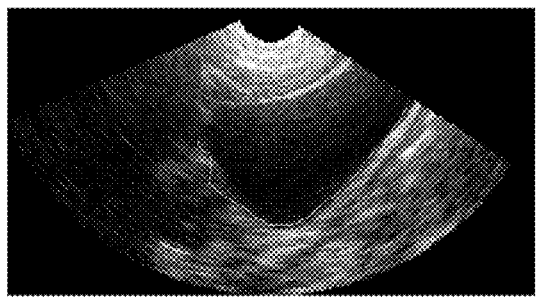
Figure 39C:
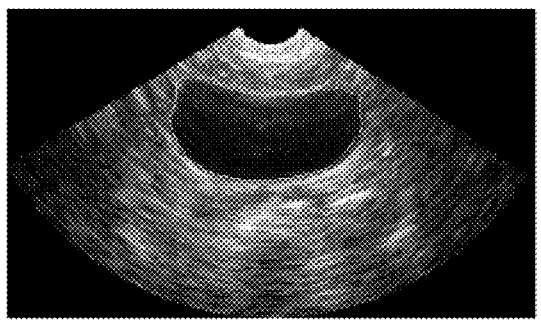
Figure 39D:
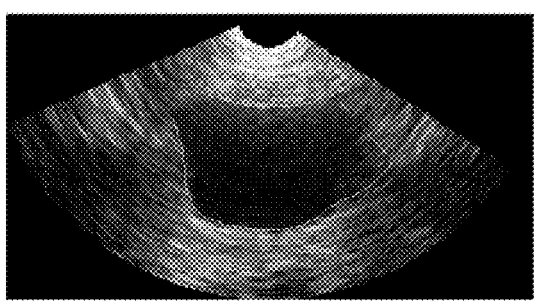

FIGS. 37A-D are B-mode scans overlaid with interface tracings obtained by the algorithms previously described. FIGS. 37A and B are sagittal plane (plane 1) images and FIGS. 37C and D are transverse images. A line along the back wall in FIG. 37A is seen and a more jagged line in FIG. 37B is shown as a consequence of noisy signals. FIGS. 37C and 37D show the cleanup of the interface tracings along the organ wall boundaries, in this case a bladder after being subjected to the morphological cleanup, sub-algorithm 192A of FIG. 32. Note the loss of the jagged interface tracings of 37B substantially smooth over and as an interface tracing 37D.

FIGS. 38A-D are B-mode scans overlaid with interface tracings before and after application of the morphological cleanup algorithms. As with FIGS. 37A-D, FIGS. 38A and B are sagittal images and FIGS. 38C and D are transverse images. Again, note the difference between FIGS. 38B whether a substantial jagging along the back wall that clearly goes into the tissue and whereas morphological cleanup there is a substantially closer interface tracing along the boundary of the organ wall, in this case, a bladder along the back wall of the bladder.

FIGS. 39A-D are B-mode scans overlaid with interface tracings. This is yet another iteration of the morphological cleanup process in which a truer fidelity is achieved demarcating in this 2-D scan images a more precise interface tracing demarcating the bladder from surrounding tissue after application of the snake algorithms.

Figure 40A:
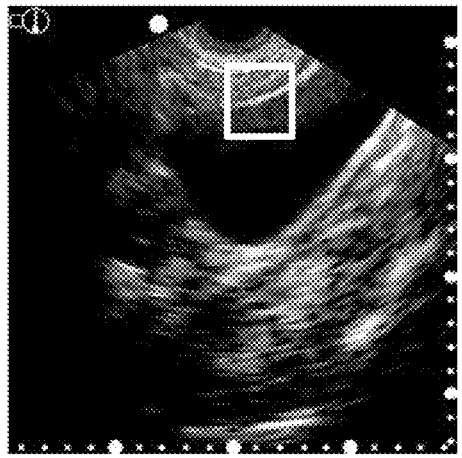
FIGS. 40A-B are normal and magnified B-mode scans overlaid with interface tracings.
Figure 40B:
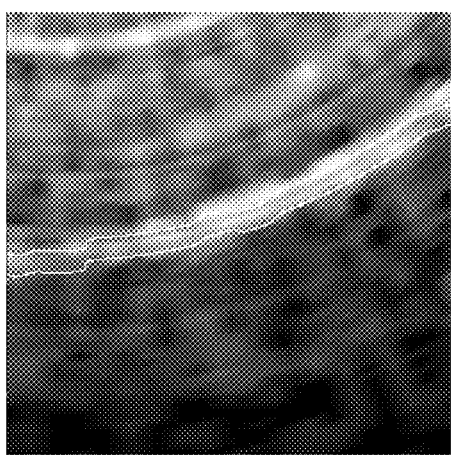

FIGS. 40A-B are normal and magnified B-mode scans overlaid with interface tracings. FIG. 40A is a normal view and has a white square looking at the bladder wall area. FIG. 40B is an expansion of the white square perimeter of FIG. 40A in which the inner and outer wall layers are shown delineated as separate tracings. There is a high degree of resolution by using the algorithms of the preceding as discussed previously.

Figure 41A:
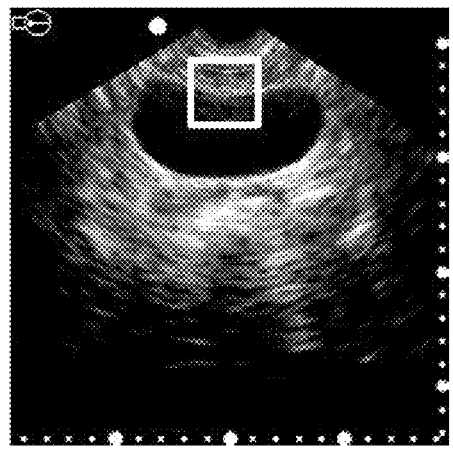
FIGS. 41A-B are normal and magnified B-mode scans overlaid with interface tracings.
Figure 41B:
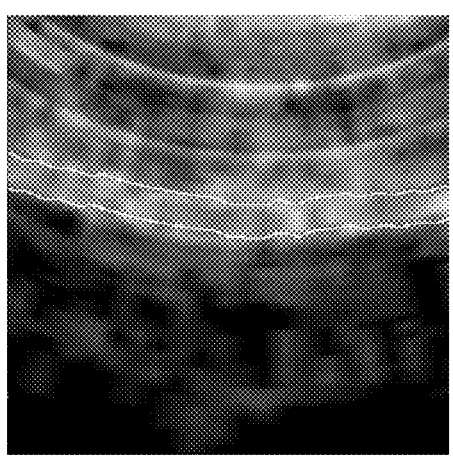

FIGS. 41A-B are normal and magnified B-mode scans overlaid with interface tracings. Similar to the tracings of FIGS. 40A and B, a normal view of FIG. 41A is shown with an enclosed square which is magnified in the FIG. 41B to show comparable high resolution interface tracings of the inner and outer wall layers of the front wall organ wall, in this case, a bladder. The front wall muscles as detected for the bladder wall in FIG. 40B and FIG. 41B are used for the thickness calculation measurements of FIG. 32.

Figure 42:
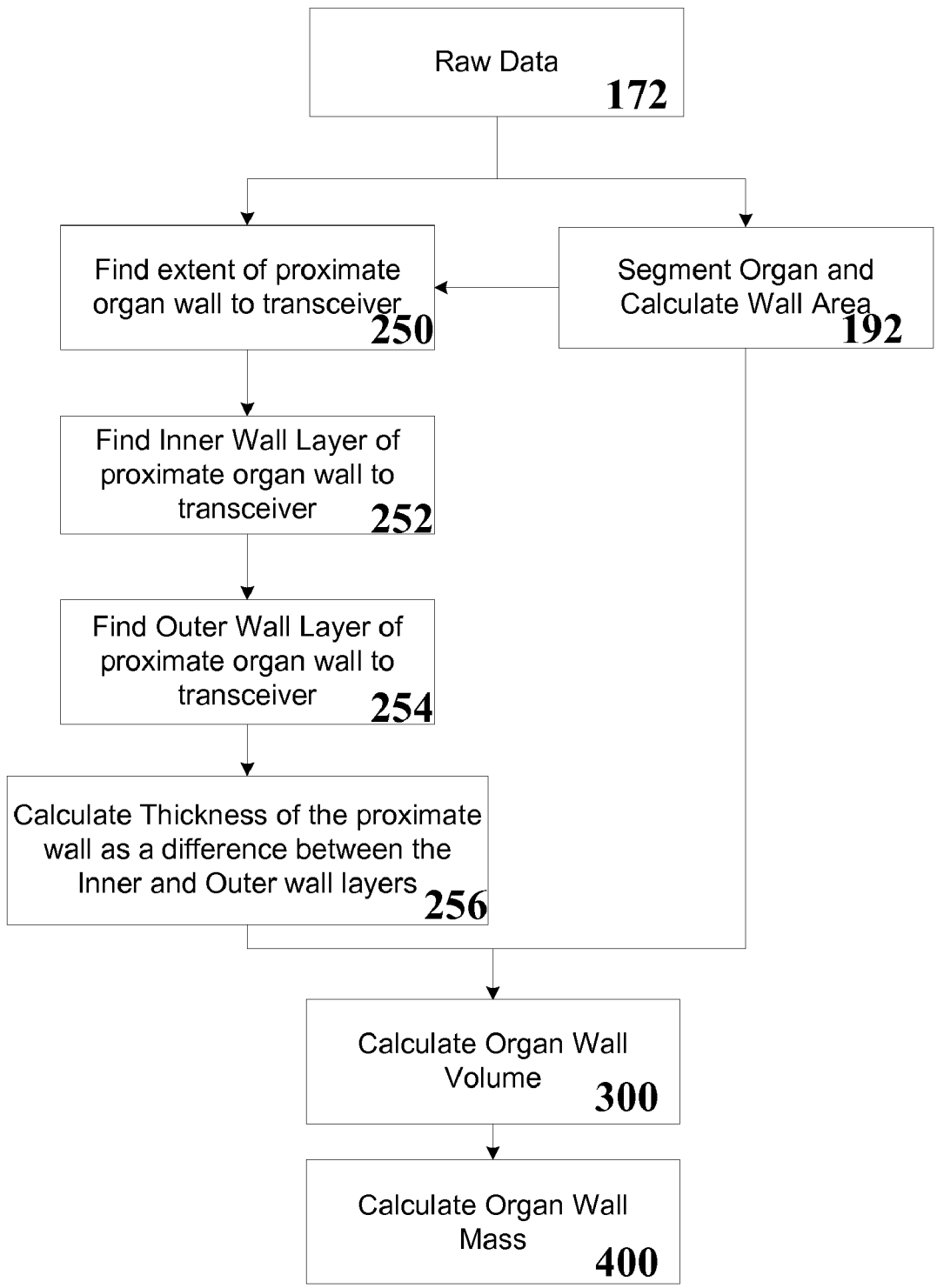
FIG. 42 is an alternative-algorithm of FIG. 15.

FIG. 42 is an alternative-algorithm of FIG. 15. Raw data is first brought under processing block 172 and thereafter the raw data is split between segmentation of the organ and calculate wall area block 192 and finding the extent (search region) of proximate organ wall to the transceiver block 250. After block 250, the inner wall layer of proximate organ wall to transceiver is achieved at block 252. Thereafter, at block 254, find outer wall layer of the proximate organ wall to transceiver is implemented. Thereafter, at block 256, the thickness of the proximate wall as a difference between the inner and outer wall layers is then calculated. Thereafter, the two parallel fracture combined merge at block 300 in which the organ wall volume is calculated and thereafter ends with block 400 in which the organ wall mass is calculated. All the processing here 250,252,254,256 is carried out on 2D or 1D data.

Figure 43A:
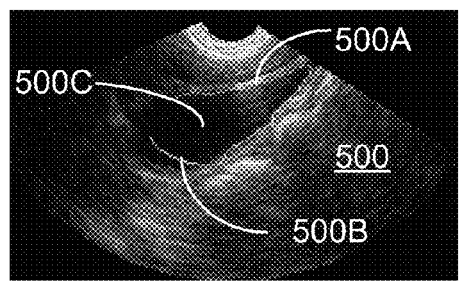
FIGS. 43A-B are B-mode scans overlaid with interface tracings.
Figure 43B:
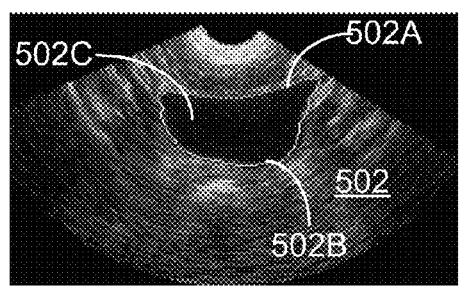

FIGS. 43A-B are B-mode scans overlaid with interface tracings. A scanplane 500 is shown having a bladder 500C which is delineated along its tissue cavity boundary by a front bladder wall 500A and a back bladder wall 500B. FIG. 43B is another scanplane from the same patient and shows the initial wall locations of a scanplane 502 about the bladder 502C in which the front wall 502A and back wall 502B is delineated by interface tracings.

Figure 44A:
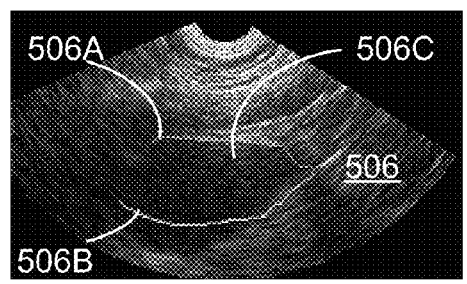
FIGS. 44A-B are B-mode scans overlaid with interface tracings.
Figure 44B:
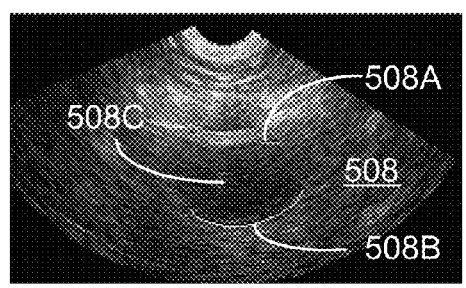

FIGS. 44A-B are B-mode scans overlaid with interface tracings. FIG. 53A is a scanplane 506 and 53B shows a scanplane 508 from the same patient. In contrast to the scanplane in FIGS. 43A and B, the boundaries are more difficult to set with the tracings and show that parts of the bladder as delineated as 506C and 508A, respectively are comparably delineated with 506A as the front wall and 506B as the back wall in scanplane 506. Similarly, the delineation of partial where only part of a front wall 508A is shown as a interface tracing and part of the rear wall 508B is shown as interface tracing. In this case here in FIGS. 43A and 43B, would receive the benefit of filling in the likely candidate points in the gaps set are between the front and rear wall interface tracings.

Figure 45A:
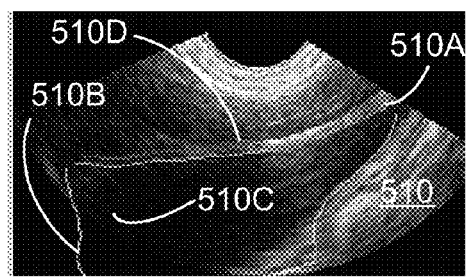
FIGS. 45A-B are B-mode scans overlaid with interface tracings.
Figure 45B:
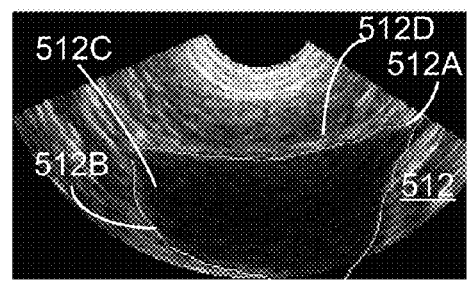

FIGS. 45A-B are B-mode scans overlaid with interface tracings. The interface tracings for scanplanes 510 and 512, respectively of FIGS. 45A and B show a partially delineated bladder that goes off scale. The bladder is respectfully represented as 510C and 512C and the figures and the respective front walls are 510A and 512A and the rear walls are 512B and 510B. Of interest to note is that using the method the algorithms of the system is that the outer wall layer and inner wall layer is more clearly delineated. The outer wall layer in scanpiane 510 is shown as 510D and the inner wall layer is shown more clearly as 510A for the front wall. The rear wall does not shown this delineation with tracings at this point.

Figure 46A:
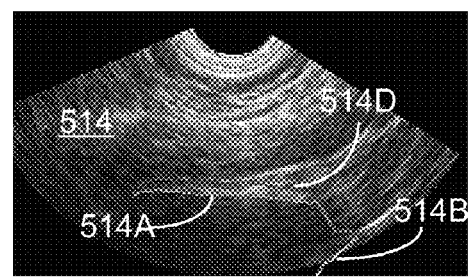
FIGS. 46A-B are B-mode scans overlaid with interface tracings.
Figure 46B:
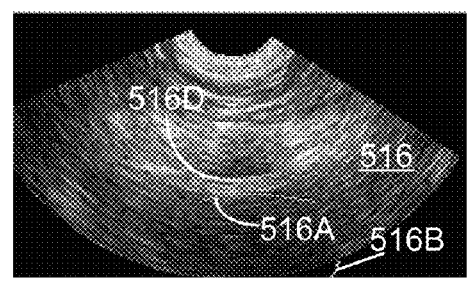

FIGS. 46A-B are B-mode scans overlaid with interface tracings. The interface tracings as shown in the previous FIGS. 46A and B show the front wall tracings for the inner and outer wall layers. In scanplane 514 of FIG. 46A, the outer wall layer of 514D is shown and inner wall layer 514A is shown of a partially revealed bladder. Also shown in scanplane 514, is the partial back wall delineation along tracing 514B. In FIG. 46B, scanplane 516 shows a slight proportion of the inner wall layer of 516A and the outer layer of 516B and only a very small portion of the back wall 516B.

Figure 47A:
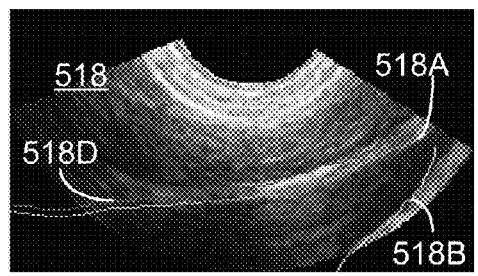
FIGS. 47A-B are B-mode scans overlaid with interface tracings.
Figure 47B:
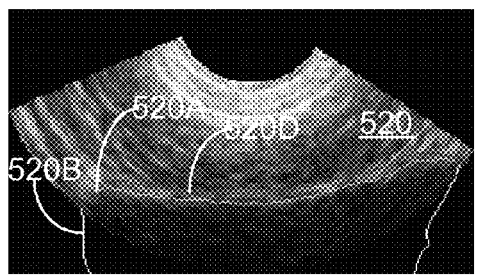

FIGS. 47A-B are B-mode scans overlaid with interface tracings. FIG. 47A concerns scanplane 518 and FIG. 47B concerns scanpiane 520. In scanplane 518, the outer layer wall of 518D may be seen traced with the inner layer wall 518A. The back wall 518B is shown partially traced. In FIG. 47B scanplane 520 is sequential with scanplane 518 of FIG. 47A and another view of the delineated bladder may be seen. Due to the differences in the scanplanes, the relatively full bladder may be seen where the proximate or forward bladder wall is seen delineated with the inner wall 520 and the outer layer wall 520D. Also, visible is the delineation for the back wall 520B that goes off image.

Figure 48A:
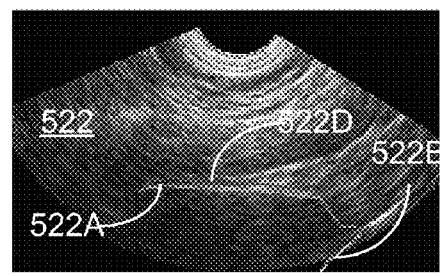
FIGS. 48A-B are B-mode scans overlaid with interface tracings.
Figure 48B:
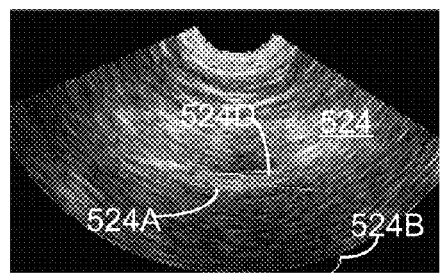

FIGS. 48A-B are B-mode scans overlaid with interface tracings using the preceding algorithms. FIG. 48A and 48B present to a sequential scanplane from a different patient with different views of the bladder available. In scanplane 522, the inner layer 522A of the proximate or forward bladder wall is shown delineated and the outer layer 522B is shown delineated with the interface tracings. The back wall 522B is shown slightly delineated and off image. Similarly, FIG. 48B shows scanplane 524A with only a portion of the bladder visible, but nevertheless the inner layer 524A is shown with the interface tracing along with the outer layer 524D with an interface tracing for the proximate forward bladder wall. Only a portion of the back wall of 524B is visible.

Figure 49:
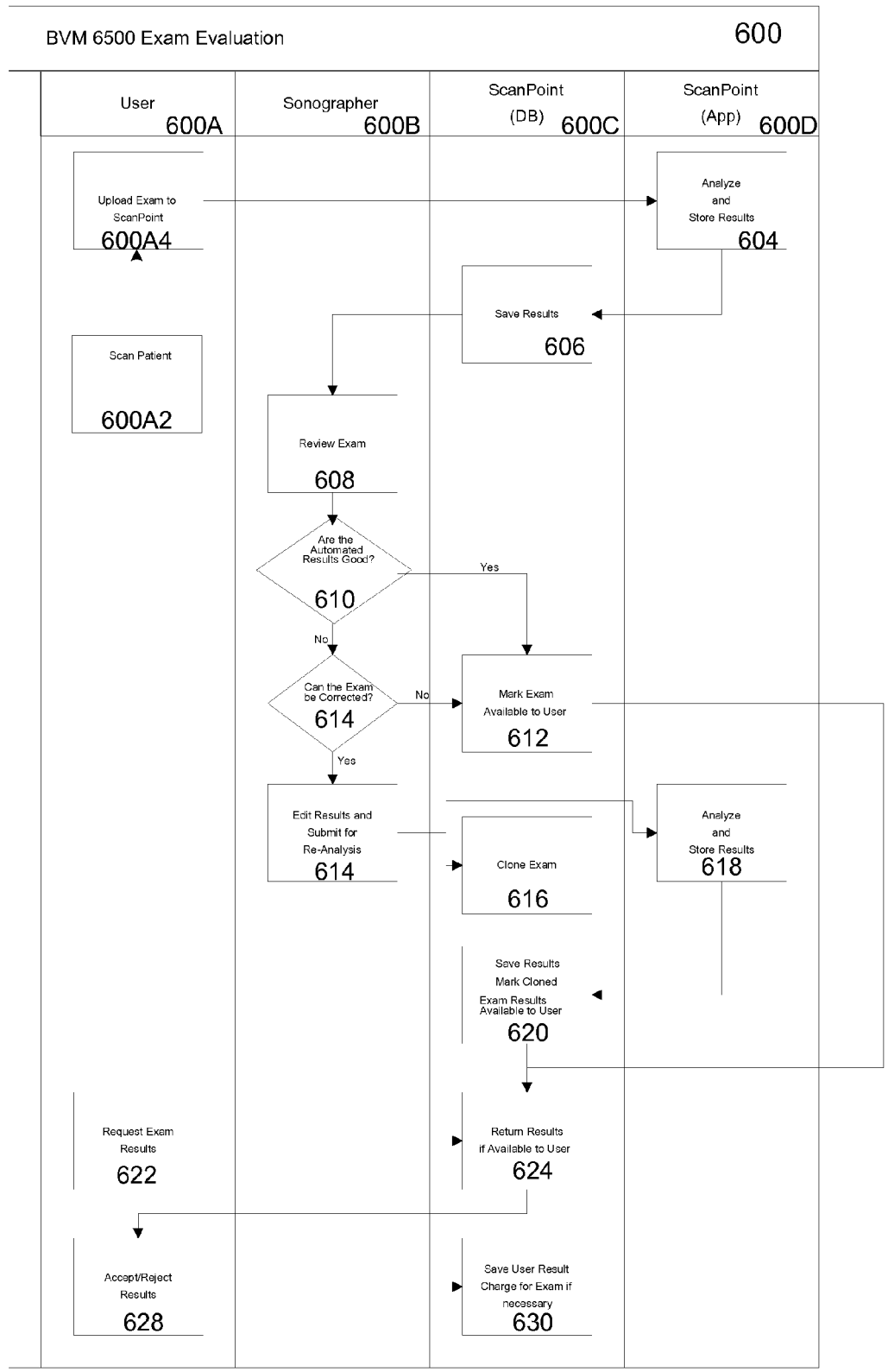
FIG. 49 is a method algorithm for the Internet System.

FIG. 49 is a method algorithm for the Internet System used to measure organ wall mass. In FIG. 49, the exam valuation is for a BVM 6500 transceiver end block 600. Block 600 is composed of a user block 600A, a sonographer block 600B, and ScanPoint database block 600C, and a ScanPoint application block 600D. The Internet system 600 uses a coordinated interplay between the user block 600A dismounted for 600B via database ScanPoint software 600C and the ScanPoint application software of 600D. The user begins the exam evaluation 600 by scanning the patient at procedural block 600A2. Thereafter, at procedural block 600A4, the exam is off-loaded to the ScanPoint server. The ScanPoint server block 604 receives the analysis and stores the results from the exam uploaded from block 600A4. Thereafter, the results are saved in the ScanPoint database 600C at procedural block 606. A sonographer experienced to review the images and results from the ScanPoint database 600C at procedural block 606 reviews the exam at block 608. Thereafter, a decision diamond 610 occurs in the sonographer column 600B where the query is as presented, "Are the automated results good?" If the answer is "no", the another decision diamond is presented at 614 with the query, "Can the exam be corrected?" If the answer is "yes" to the query in decision diamond 614, at block 615, the results are edited and submitted for re-analysis. Returning back to decision diamond 610, if the answer is "yes" to the query, "Are the automated results good?" the procedure returns to the ScanPoint database 600C column where at block 612 the exam is marked available to user. Upon successful assessment by a sonographer at decision diamond 610, and after being marked available for user at procedural block 612, the exam results are made available to the user at block 624 wherein it then becomes accepted by the user for evaluation at block 628 within the user column 600A. In block 628, the user accepts or rejects the results after the sonographer has approved it. The accepted to rejected results from procedural block 628 is then sent to the ScanPoint database and stored at procedural block 640. In the ScanPoint 600C. Returning to the sonographer, column 600B at procedural 615, there are two options that occur at ScanPoint database 600C and ScanPoint application 600D. In the ScanPoint database column 600C, a procedural block 616 for clone exam is available. In the cloned exam procedure, the exam may be repeated as desired by the sonographer. Alternatively, in the ScanPoint application software 600D at procedural block 618, the results of the scan may be analyzed and stored. Thereafter, returning to the ScanPoint column 600C, the results that are saved are marked clone and the exam results are made available to the user. Thereafter, at block 624, the exam results are made available to the user and from block 624 and the user column 600A the user then reviews the exam results at block 628 and decides to accept or reject the results. Thereafter, the user returns to the ScanPoint database column 600C and the results are saved and a charge for the exam is made if necessary procedural block 630. From preceding detailed description of the major operation processes of the exam evaluation 600, it can be seen that the bladder mass exam is deployed via the Internet system as a reviewed exam. An experienced sonographer reviews the exam and the resulting data is re-analyzed as needed. As shown in the user column 600A, the user is free to scan a patient prior to after preparing an exam in ScanPoint. In starting block 600A2, the user performs the following steps substantially similar to that described in sub-algorithm 172 of FIG. 15. First, the patient is palpated to determine the location of the symphysis pubis or the pubic bone approximately two centimeters or one inch above the patient's symphysis pubis along the patient's midline the transceiver 10 is placed. Prior to that, either a sonic gel pad is placed at this location or a ultrasound conveying gel is applied to the patient's skin. Thereafter, the transceiver 10 currently a BVM 6500 scanner is placed in the center of the gel pad or near the center of the applied gel. Then, the scan button is released to acquire the rotational array of 2-D scanplanes referred to as VMode™ scan. Once the VMode™ scan trademark is completed, the results are conveyed as indicated in the flowchart of FIG. 49. The particular embodiment to the transceiver 10 specifically the BVM 6500 scanner can notify the user, through display presented arrows, whether or not the aim of transceiver 10 needs to be adjusted to acquire the organ of interest, in this case a bladder, so as to acquire the bladder in a more reasonably centered location. Attempts to prove the aim at this point are recommended, but optional. That the organ of interest in this case, a bladder is properly centered is verified by getting consistent readings through multiple repositions. It is suggested that at least three volume readings be acquired that are consistent. As previously indicated in the Internet system method of FIG. 49, the exams uploaded to the ScanPoint software and is available soon thereafter for review by a sonographer. The sonographer reviews the raw data uploaded to the ScanPoint database and analyzes the organ volume surface area and wall mass. The sonographer can assess the results as is, reject the exam outright, or edit the exam. If the sonographer accepts or rejects the exam, the result is immediately available to the user. If the sonographer chooses to edit the exam, a new window opens on the computer display. In this window, sonographer will trace inner and outer bladder wall layers on both the sagittal plane and on the transverse plane by selecting a series of points. These measurements will be uploaded to the ScanPoint software database and ScanPoint application. The ScanPoint Internet system will clone the exam results to form a new record and raw data will be re-analyzed with the sonographer's measurement locations. The sonographer's measurement will be added to the zoom thickness measurements after this repeated analysis. After the re-analysis is complete, the results corrected by the sonographer will be presented to the user along with the original thickness measurement result. At this point, the user is free to view the results. The user may accept or reject the exam in the same manner as other exams available and the ScanPoint suite.

Figure 50:
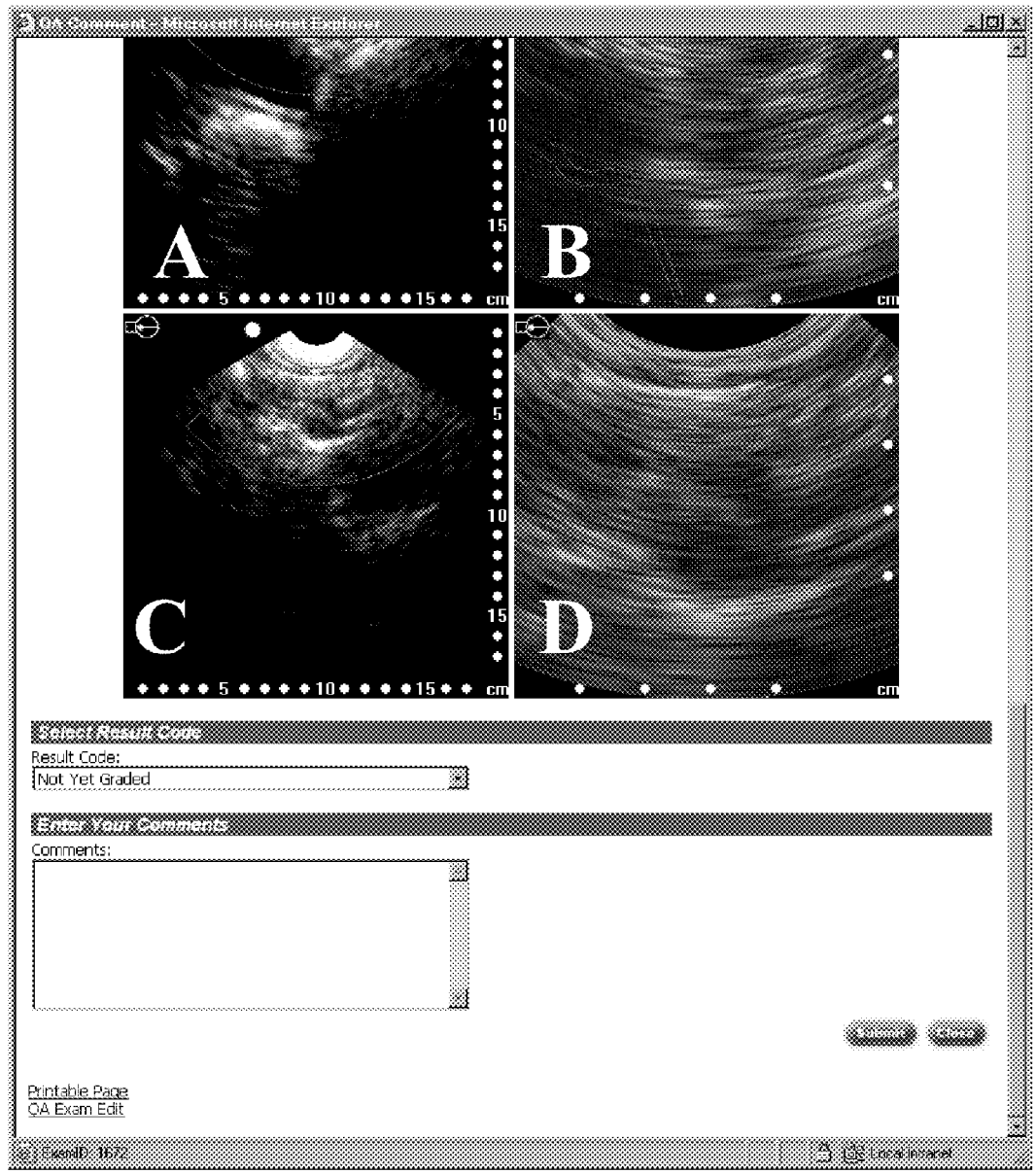
FIG. 50 is a screen shot of four image panels.

FIG. 50 is a screen shot of four image panels A-D. The screen shots are what is available to be seen by the user or sonographer after his points along the execution of the Internet algorithm as described in FIG. 49.

Figure 51:
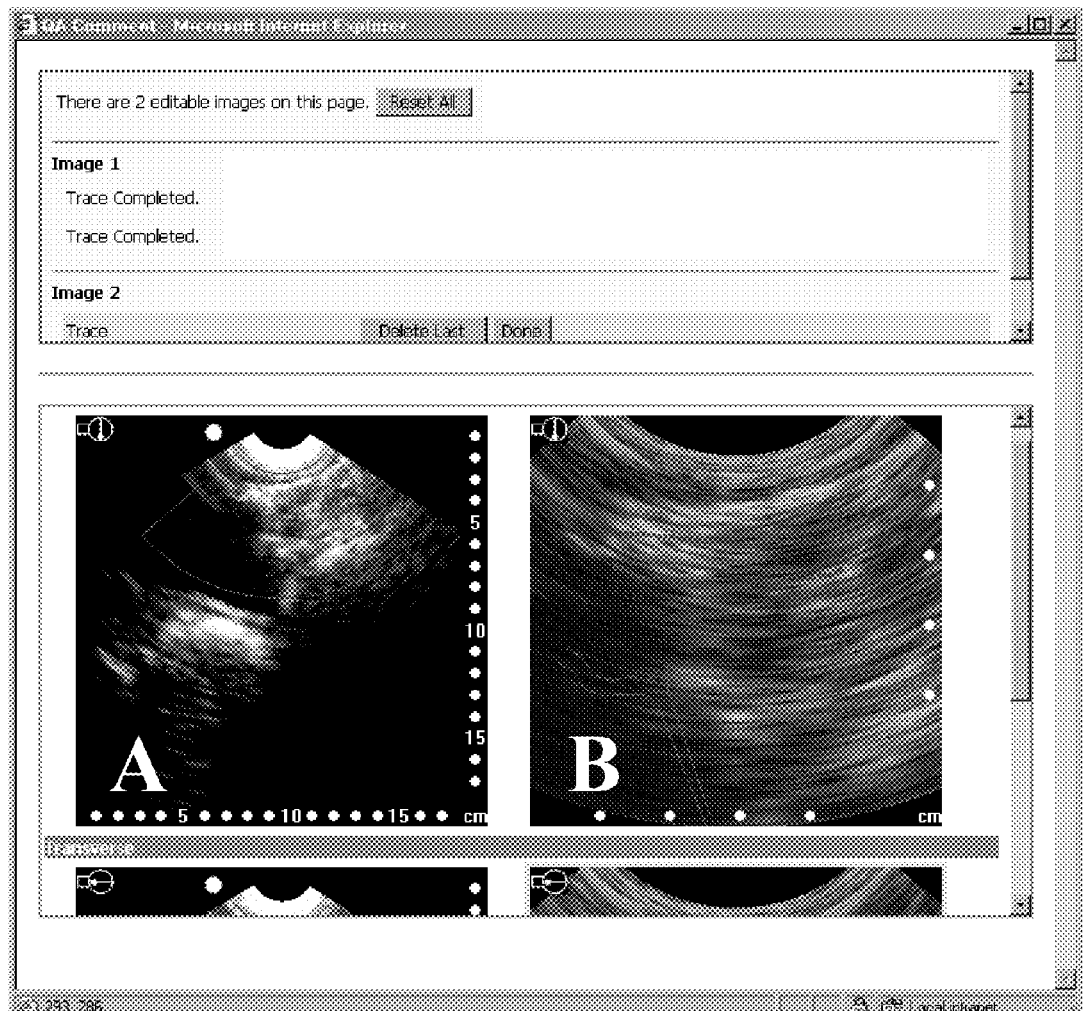
FIG. 51 is a screen shot of two image panels.

FIG. 51 is a screen shot of two image panels A and B. The screenshot as shown shows two other image panels with two inner face tracings drawn in image B. The two images here are editable as needed.

Figure 52:
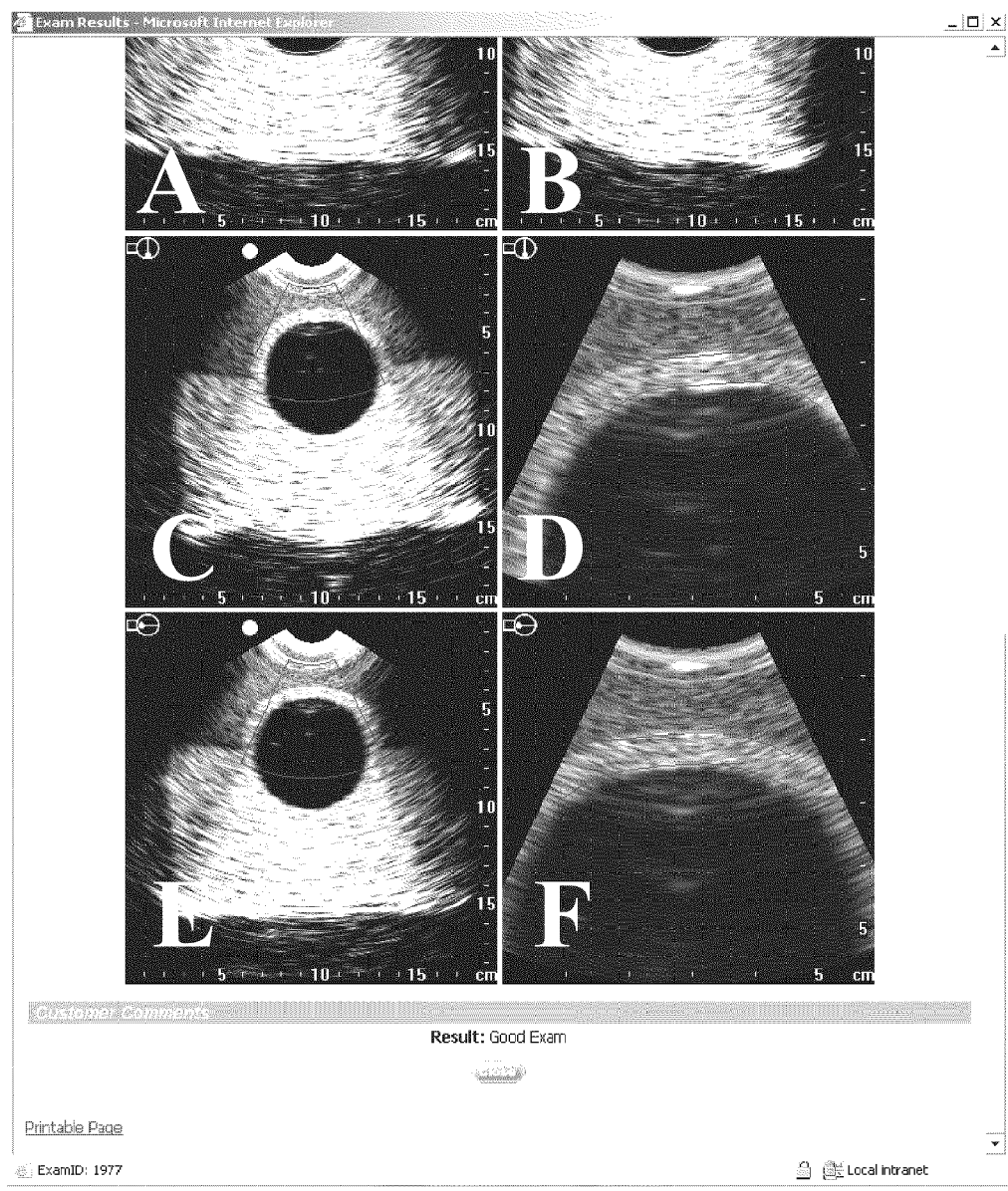
FIG. 52 is a screen shot of six image panels.

FIG. 52 is a screen shot of six image panels A-F. The six screen shots are acquired and show different degrees of image processing and overlaying of interface tracings for the outer at inner wall layers of the proximate or forward organ wall.

Figure 53:
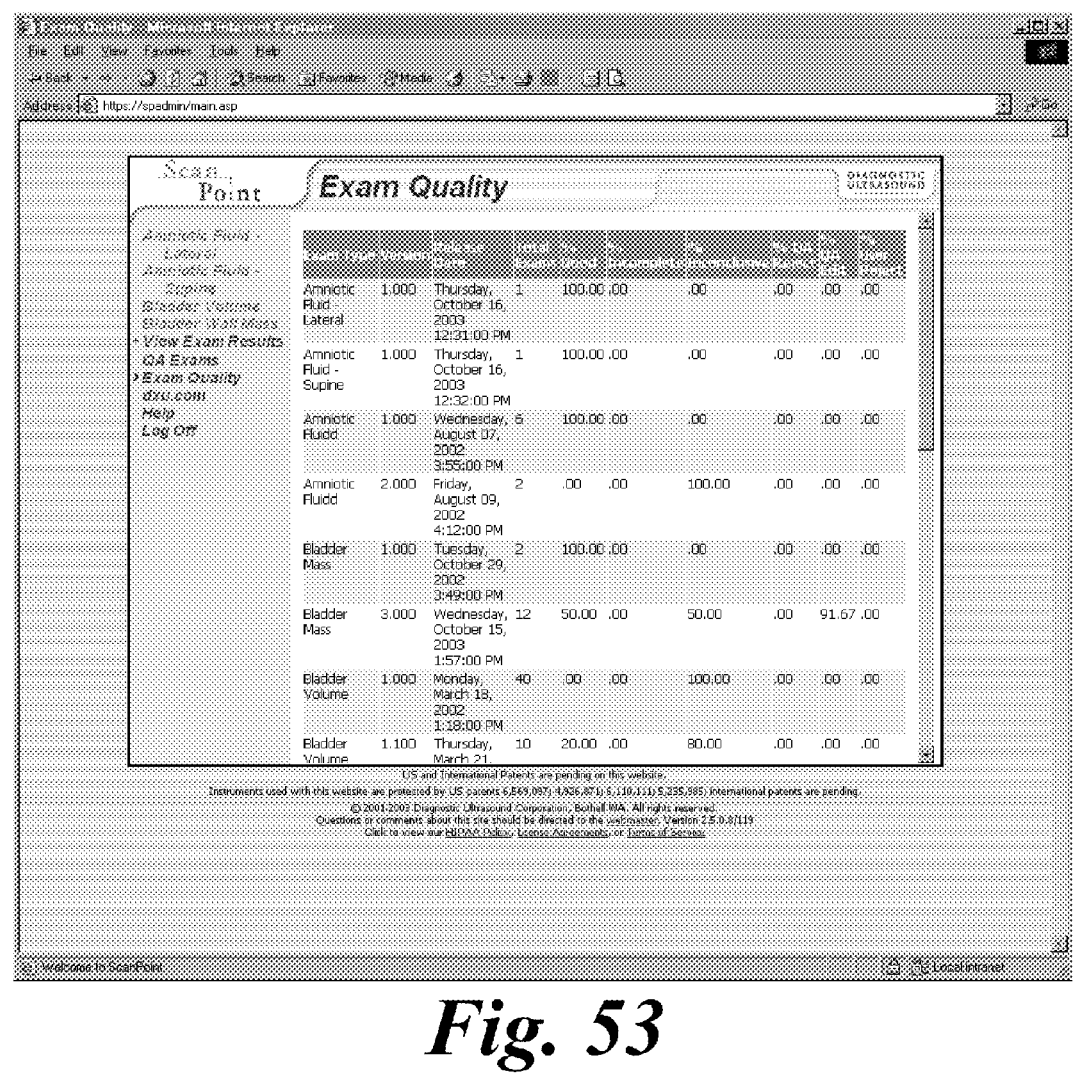

FIG. 53 is a screen shot of Exam Quality Report. The Exam Quality Report has different test options including bladder mass, bladder volume, amniotic fluid volume, etc., as well as different levels of descriptors that categorize whether the particular exam selected is % incomplete or % inconclusive, the number of exams, the percent good they were, the amount of % that are quality assurance rejected or % that are quality assurance edited, or the number in which the user has rejected.

Figure 54:
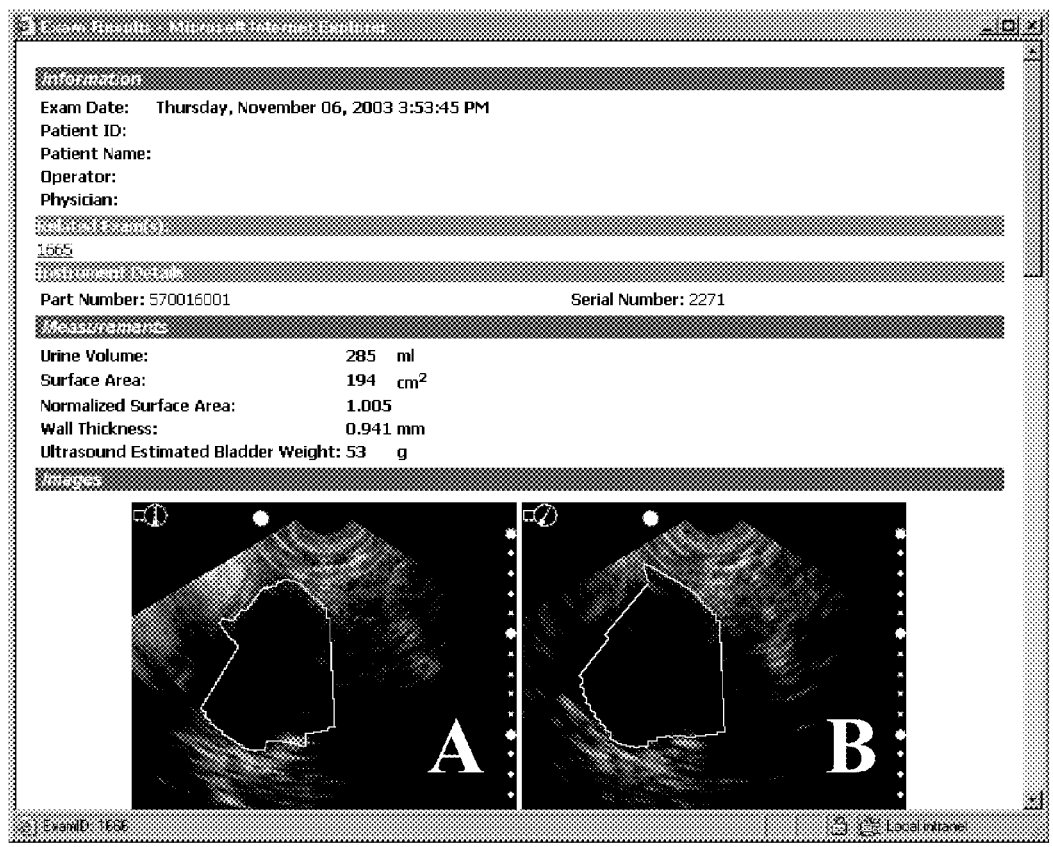
FIG. 54 is a screen shot of two image panels.

FIG. 54 is a screen shot of two image panels A and B indicating initial segmentation of a bladder. The bladder that has been segmented is an early stage of organ wall tissue interface resolution as indicated by the relative jagged interface tracings.

Figure 55:
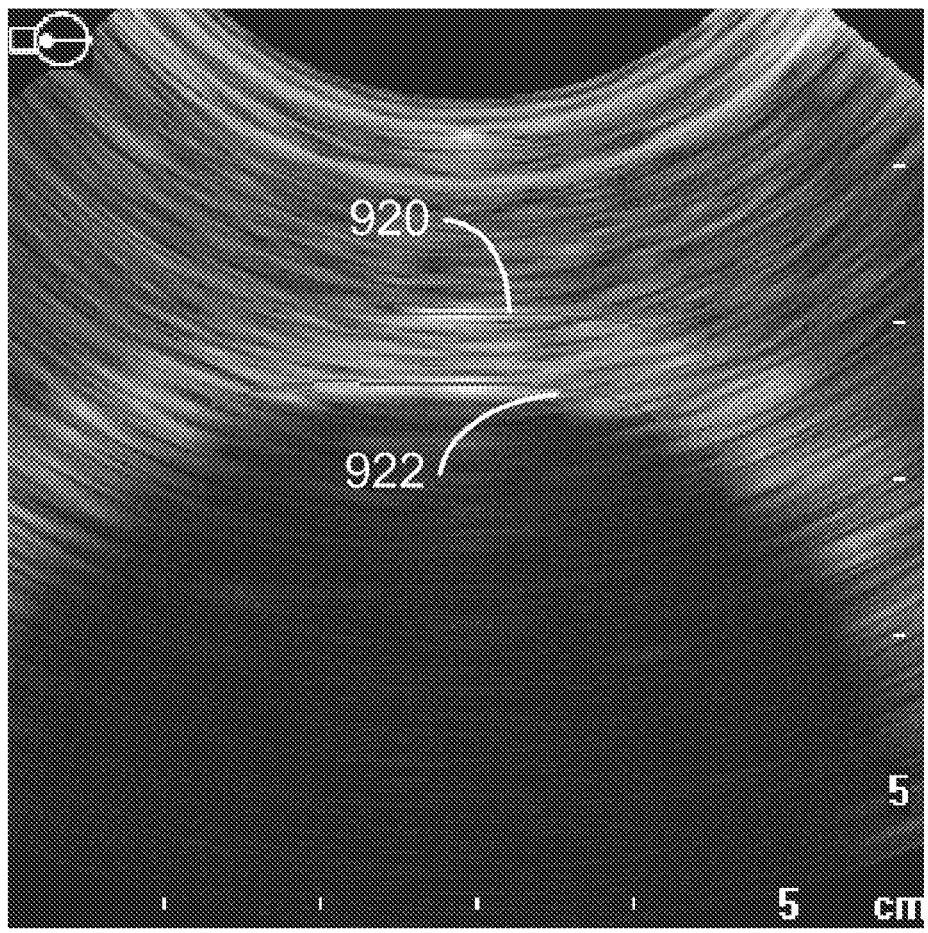
FIG. 55 is a scanplane image overlaid with inner and outer wall tracings using algorithms of the Internet System.

FIG. 55 is a scanplane image overlaid with inner and outer wall tracings using algorithms of the Internet System. An outer wall layer 920 is shown in relation to an inner wall layer tracing 922. While preferred and alternate embodiments of the invention have been illustrated and described, as noted above, many changes can be made without departing from the spirit and scope of the invention.

Figure 56:
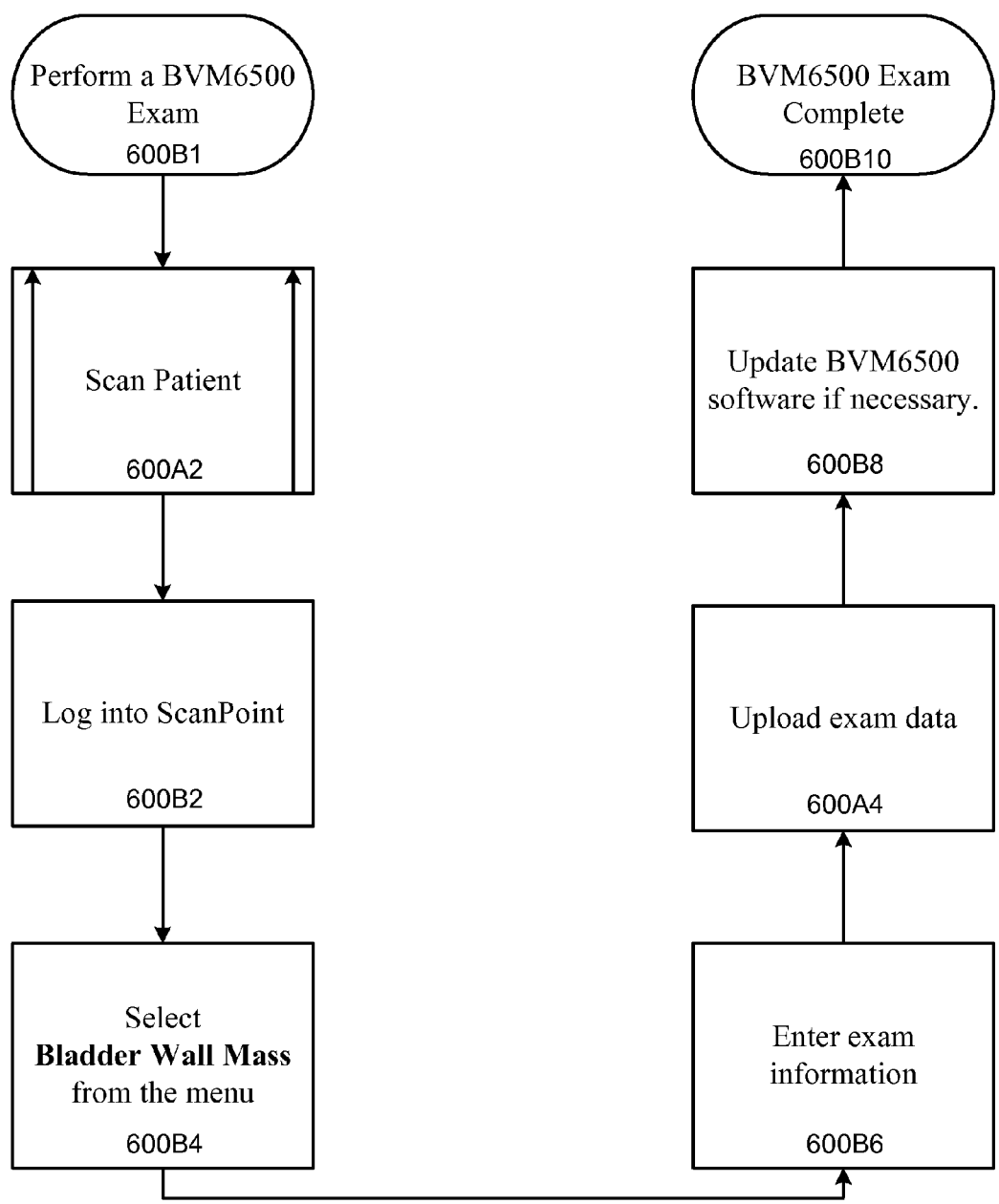
FIG. 56 is an expansion of more sub-algorithms of FIG. 46.

FIG. 56 is an expansion of the sub-algorithms of FIG. 49. Beginning with block 600B1, a decision is made to perform a BVM6500 exam. Thereafter, at block 600B2, the user logs into the ScanPoint software suite. Upon logging into the ScanPoint software suite at block 600B4, the user selects the bladder wall mass from the menu options. Upon selecting the menu options at block 600B6, the user enters exam information. Thereafter, the BVM6500 exam software is updated as necessary at block 600B8. At block 600A2, the patient is scanned as described previously. And also as described previously, the exam data is uploaded at block 600A4. Thereafter, the sub-algorithm in FIG. 49 is completed at block 600B10 in which the exam is complete for that particular section for the BVM6500 transceiver 10 particular embodiment. The sub-algorithm in FIG. 53 refers primarily to preparing the exam for scanning a patient. The procedure described is for performing an exam without preparing the patient.

Figure 57:
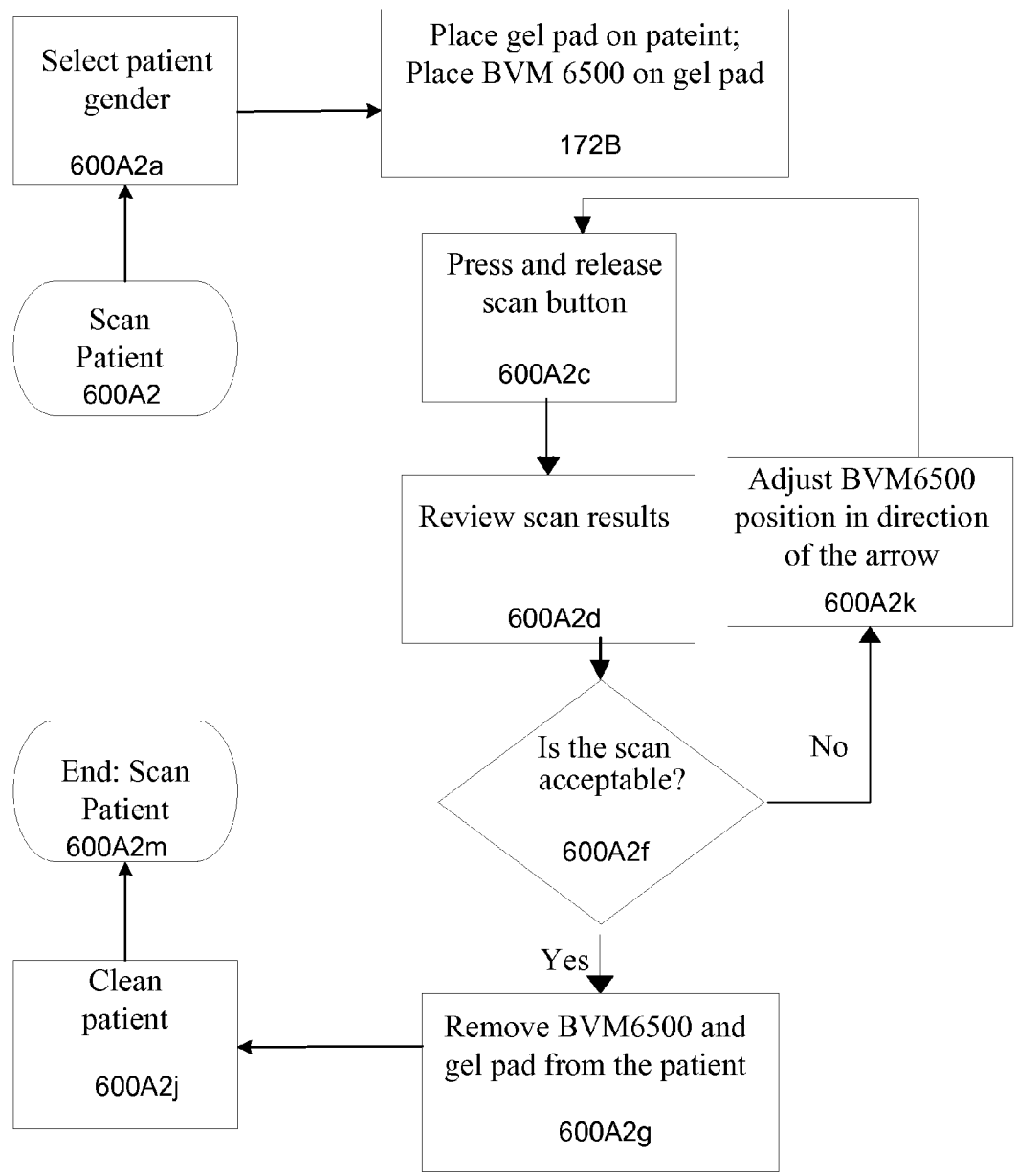
FIG. 57 is an expansion of the sub-algorithms 600A2 of FIG. 53.

FIG. 57 is an expansion of more sub-algorithms of FIG. 49. FIG. 57 describes an alternate algorithm to the sub-algorithm as described in FIG. 47. In FIG. 57, the decision is made by the user to perform a BVM6500 exam in starting block 600B1. Thereafter, the user scans the patient as previously described in block 600A2. Then the user logs into ScanPoint block 600B2 followed by selecting the bladder wall mass option from the menu at block 600B4. The user then enters the exam information at block 600B6 followed by a floating exam data at block 600A4. Then the user decides at block 600B8 to update the BVM6500 exam software if necessary and finally, the BVM6500 exam is completed at block 600B10.

FIG. 57 is an expansion of the sub-algorithms 600A2 of FIG. 49. From the 600A2 entry point, as 600A2a block the patient gender is selected on the transceiver 10 specifically the BVM6500 exam. Thereafter, as previously described at block 172B, a gel pad or sonic gel is applied directly to the patient and the BVM6500 exam is centered on the gel or on the gel pad. Then at block 600A2c, the scan button is pressed and released. At block 600A2d, scan results are reviewed and then at decision diamond 600A2f, a query is presented, "Is a scan acceptable?" If the answer is "yes" to this query at process block 600A2g, the BVM6500 is removed from the gel pad and from the patient. The patient is then cleaned at block 600A2i and the sub-algorithm ends at terminus at 600A2m for ending the scanning of the patient. Returning to, "Is the scan acceptable decision diamond 600A2f?" If the answer is no to that query, then the transceiver 10 BVM6500 particular embodiment is adjusted and is positioned as indicated by the direction of the arrows presented on the BVM6500 display. Thence, from there, the press and release scan button at block 600A2c is completed until an acceptable scan is finally reached.

Figure 58:
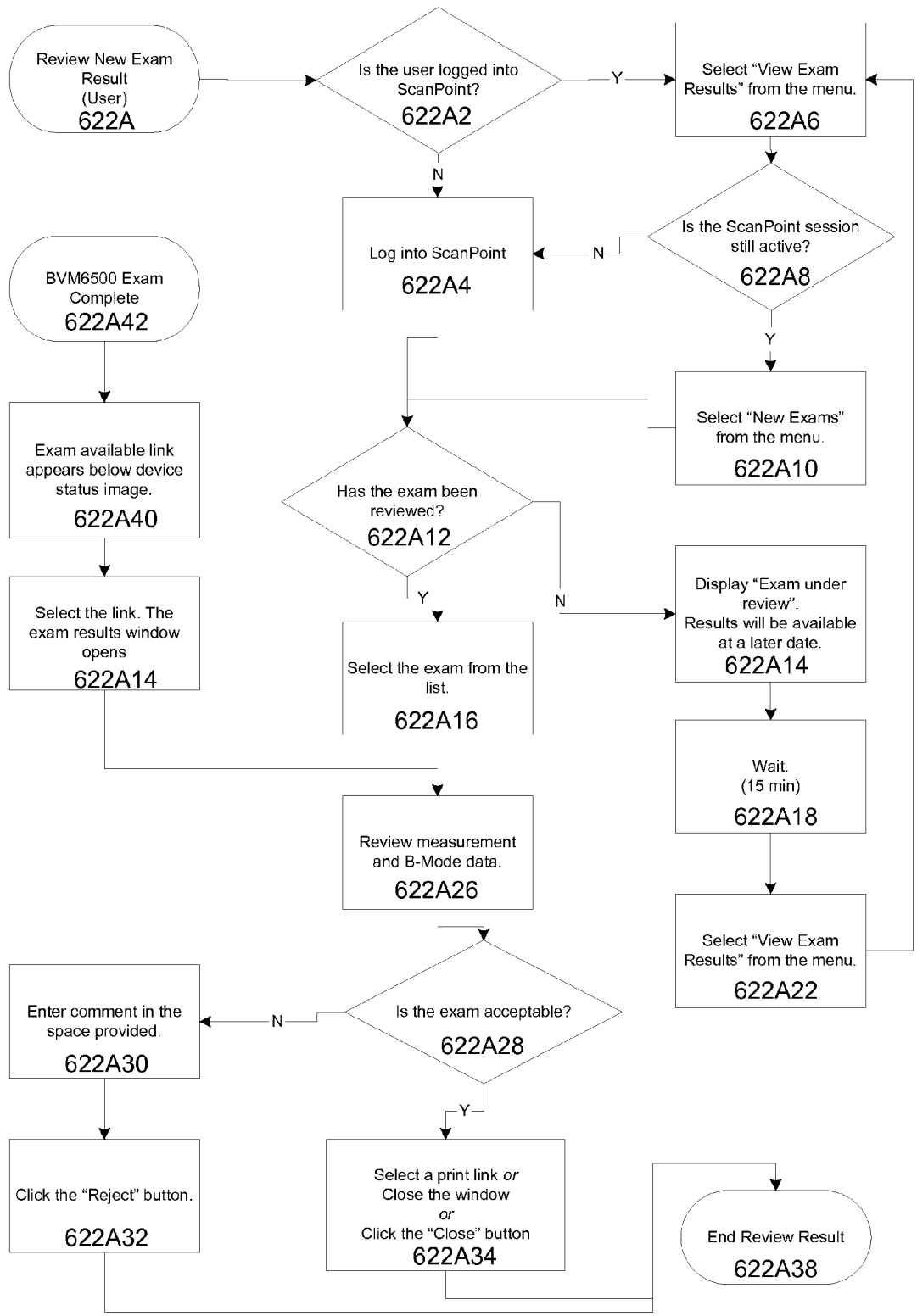
FIG. 58 is an expansion of the sub-algorithms 622 of FIG. 46.

FIG. 58 is an expansion of the sub-algorithm 622 of FIG. 49. The expansion of sub-algorithm concerns the reviewing of new exam results by a user. This sub-algorithm begins with reviewing new exam result entry point at 622A in which decision diamond 622A2, the queries presented. "Is the user logged into ScanPoint?" If the answer is "yes", the option at block 622A6 is obtained in which the process calls for selecting view exam results from the menu. If the decision at decision point 622A2 is "no", then at procedural block 622A4, the user logs into ScanPoint. Returning to block 622A6, upon selecting the view exam results from the menu, a decision diamond is reached with the query. "Is the ScanPoint session still active at decision diamond 622A?" If the answer is "no" to this query, then the user is routed to log in to ScanPoint at block 622A4. If the answer is "yes" to this query, then the user proceeds to block 622A10 to select the exams from the menu. Thereafter, from block 622A10, or alternatively from block 622A4, both converge at the next decision diamond 622A12 and are presented with the query. "Has exam been reviewed?" If the answer to this query is "no", then the next procedural block 622A14 in which the display exam under review is shown and a statement that results will be available at a later date. If the answer to the query in 622A12 is "yes", then user at block 622A16 is presented with the option to select the organ mass or bladder mass exam from a list of exam menu options. If upon selecting the bladder mass or organ mass exam at block 622A16, the user then may review the measurement and the B-mode to the data at block 622A6. Upon review of the data, another decision diamond is reached at decision diamond 622A28 with the query, "Is the exam acceptable?" If the answer is "yes", the user selects a print link or closes a window or clicks the close button at block 622A34. From here, the end of the review result is reached at block 622A38. Returning to block 622A14, after the exams are reviewed, the process continues to block 622A18 in which there is a wait period commonly 15 minutes, maybe shorter, or maybe longer. Thereafter at block 622A22, select view exam results from the menu is presented to the user and then this returns to block 622A6 to select the view exam results from the menu and the loop proceeds from that point 622A8. The ScanPoint session is still active. Returning to the decision diamond 622A28, if the exam acceptable, should the answer to this query be "no", the user at block 622A30 enter comment in the space provided. Thereafter, at block 622A32, the user may collect the reject button and then proceeds to end of review results at terminus 622A38. The reviewing new exam results by the user in FIG. 49 has another entry point which is at 622A42 in which the BV6500 exam is already complete, then that is followed by block 622A40 in which the exam available link appears below the device status image. Thereafter, at block 622A14, the link is selected and exam results window opens. After the exam window opens, the procedure follows to review measurement and B-mode data in block 622A26. From block 622A6. the decision diamond as previously described in block 622A28 is reached, is exam acceptable and the rest of the algorithm proceeds as previously described.

Figure 59:
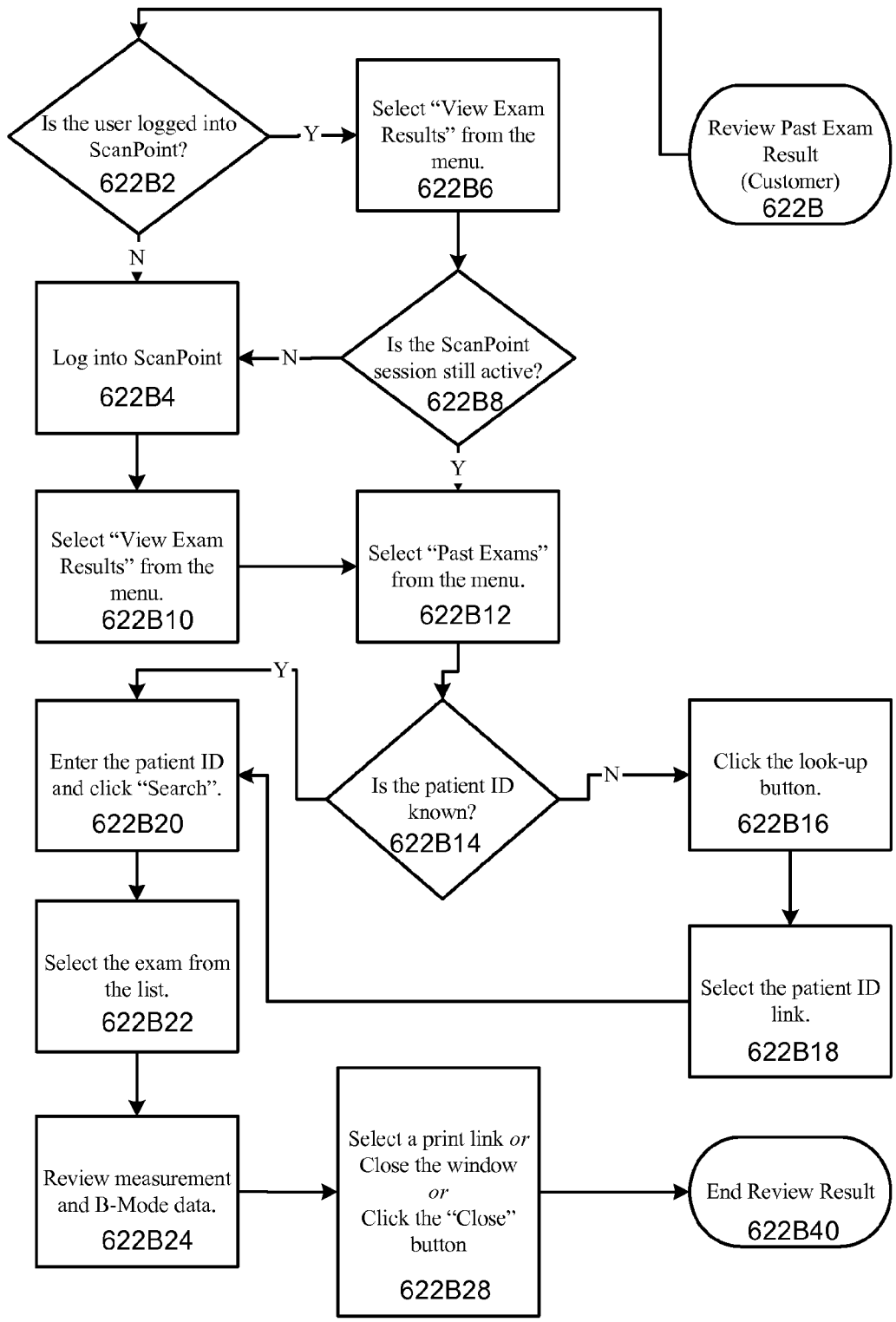
FIG. 59 is another expansion of the sub-algorithms 622 of FIG. 46.

FIG. 59 is another expansion of the sub-algorithm 622 of FIG. 49. Sub-algorithms concern reviewing past exam results by a user. Beginning at entry point 622B, review past exam results by the user or customer proceeds to a decision diamond 622B2 is the user logged into ScanPoint If the answer us "yes", then procedural block 622B6 is reached and the user selects the exam results from the menu, or if the answer to the query in 622B2 is "no", then the user has to log into ScanPoint as indicated in block 622B4. Returning to 622B6, once the user then proceeds to a decision diamond and the query as presented is ScanPoint session still active at 622B8. If the query is negative for that, then the as previously described, the user needs to log into ScanPoint at 622B4. If the answer to the query in 622B8 is "yes", then the user selects the past exams option from the menu at 622B12. Returning to 622B4, if the user needs to log into ScanPoint, thereafter at 622B10, the user selects view exam results from the menu and then proceeds to block 622B12 select past exams from the menu. Once the past exams have been selected from the menu, a decision diamond is reached at 622B14, is the patient ID "no?" If the answer to this query is "no", then the procedure continues with 622B16 where the user needs to click the look-up button. Thereafter, at 622B18, the user needs to select the patient ID link. Upon selecting the patient ID link, the next procedure is enter the patient ID and click search at block 622B20. Returning back to the decision diamond 622B14, if the answer is "yes" to the query, "Is the patient ID known?" then again, the user proceeds to block 622B20 and the patient ID is entered by clicking search. Thereafter, at block 622B22 the exam is selected from the list of other exam options. In this particular case, it would be for organ mass and configured for bladder. for example. Thereafter, at block 622B24, the B-mode data and the measurements from the B-mode data are reviewed. Thereafter, at block 622B28, the user selects a print link or close a window or clicks the close button and finally the procedure ends with the image review result at terminus 622B40.

Figure 60:
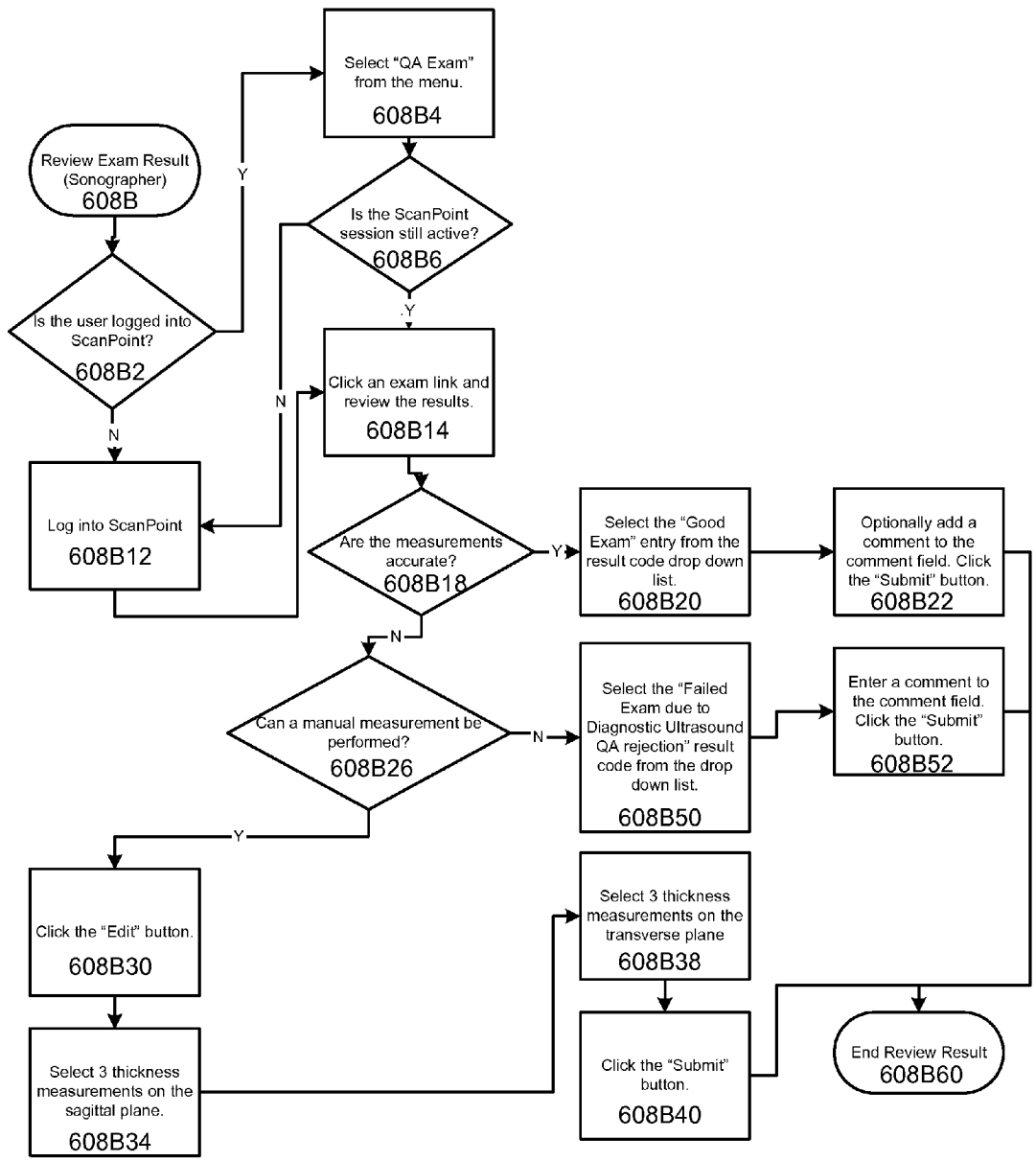
FIG. 60 is an expansion of the sub-algorithms 608 of FIG. 46.

FIG. 60 is an expansion of the sub-algorithms 608 of FIG. 49. The sub-algorithm as described in FIG. 60 concerns reviewing new exam results by the ultrasonographer. FIG. 60 begins with entry point 608B review exam results by the sonographer. The next point that is reached is a decision diamond 608B2 in which the sonographer is presented with the query "Is the user logged into ScanPoint?" If yes, then the next procedural block is 608B4 and the option is presented to select a QA exam from the menu. If the answer to the query at 608B2 is "no", then the sonographer has to make sure that ScanPoint is logged into at block 608B12. Returning to block 608B4. once the QA exam is selected from the menu, the decision diamond is reached at 608B6 with the Query, "Is the ScanPoint session still active?" If that is "no", then the log in to ScanPoint procedure is performed at block 608B12. If the answer is "yes", then block 608B14, the exam link is clicked in order to review the results. From 608B14, a decision diamond is reached with the query, "Are the measurements accurate at 608B18?" Should the answer be "no", to this query, then another decision diamond is reached at 608B26 with the query, "Can a manual measurement be performed?" If the answer is "yes" to this query, then at procedural block 608B30, the edit button is clicked. At procedural block 608B34, the option to select 3 thickness measurements on the sagittal plane is engaged. From 608B34, the next block is 608B38 in which 3 thickness measurements on the transverse plane is selected and thereafter, at block 608B40, click the submit button is engaged. Then in this direction of the sub-algorithm flowchart, the terminus is reached at 608B60 for end the review results by the sonographer. Returning to the decision diamond 608B18 with the query, "Are the measurements accurate?" Should the answer be "yes", then at procedural block 608B20, the option select the "Good Exam" entry from the result code drop down list is performed. Thereafter, at procedural block 608B22, the sonographer has the option to add comment to the comment field. The sonographer does so by clicking the submit button. From this point, the sonographer then proceeds to 608B60 for end review result as indicated in the terminus symbol. Returning to the decision diamond 608B26, "Can a manual measurement be performed?" If the answer to this query is "no", the next procedure is 608B50 in which the sonographer may select the "failed exam due to diagnostic ultrasound QA rejection" result code from the drop down list. Upon selecting the QA rejection drop down code, the next procedural block 608B52 and the sonoarapher enters a comment to the comment field by clicking a submit button. Thereafter, the end review results terminus 608B60 is reached.

Figure 61:
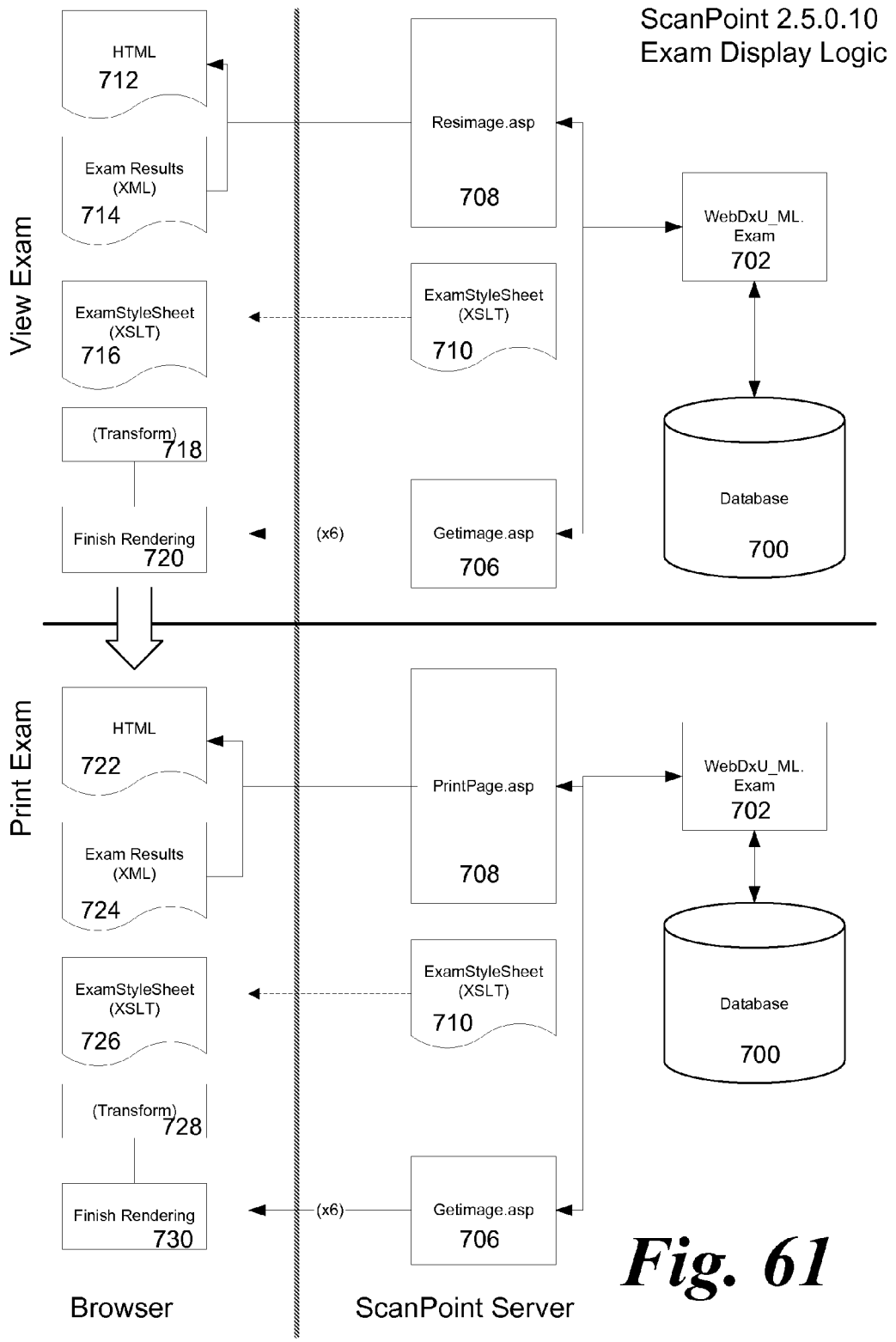
FIG. 61 is a Display Logic Flowchart of the Internet System.

FIG. 61 is a Display Logic Flowchart of the Internet System. As shown in the figure, this is for the ScanPoint version 2.5.0.10. There are two major sections, a view exam section and a print exam section that is cross-referenced with a browser and a ScanPoint server column. The view exams and the prints exams use the same part of a ScanPoint display logic flowchart both use a database 700, WebDxU_ML exam page 702, a Getimage.asp software command 706, a PrintPage.asp command 708. and an XSLT ExamStyleSheet 710. Review Exam has an html sheet 712. Exam Results XML sheets 712, an ExamStyleSheet XSLT 716 which is subjected to a transform procedure 718 and a Finish Rendering procedure 720. From the Finish Rendering 720 from the view exam side then continues to the print exam side in which an html document is printed the exams from the html document 724 is reviewed. The html document 722 is printed as a consequence of the print page command .asp 708 structure. Similarly, there is an ExamStyleSheet XSLT 726 that comes from via the database 700 via the ExamStyleSheet XSLT sheet 710. Thereafter, again under the browser print exam version, the transform process 728 and the finish rendering and it concludes with a finish rendering process 730. The Resimage.asp block 707 searches the browser DOM category for all "ing" elements containing a "DSRC" attribute. For each node encountered an attempt is made to find a matching DSRC in the image cache. If a match is found, then the source or "SRC" attributes will be set from the cache image object. If not, then a new image object is created, downloaded, and cached for a future use. This allows image cache mechanism to be invoked immediately after a document is transformed as indicated in the transform block 718 or transform block 728. A cacheable image is one that has a node name of the "ing" and contains an attribute with the name of "DSRC". The nodes do not have a "SRC" attribute. For the Getimage.asp block 706, gains a parameter of "cache="yes" and causes application specific HGTP response headers to be set to allow a cache of five minutes instead of a default which is set to expire immediately. Further explanations are provided in FIG. 65 below.

Figure 62:
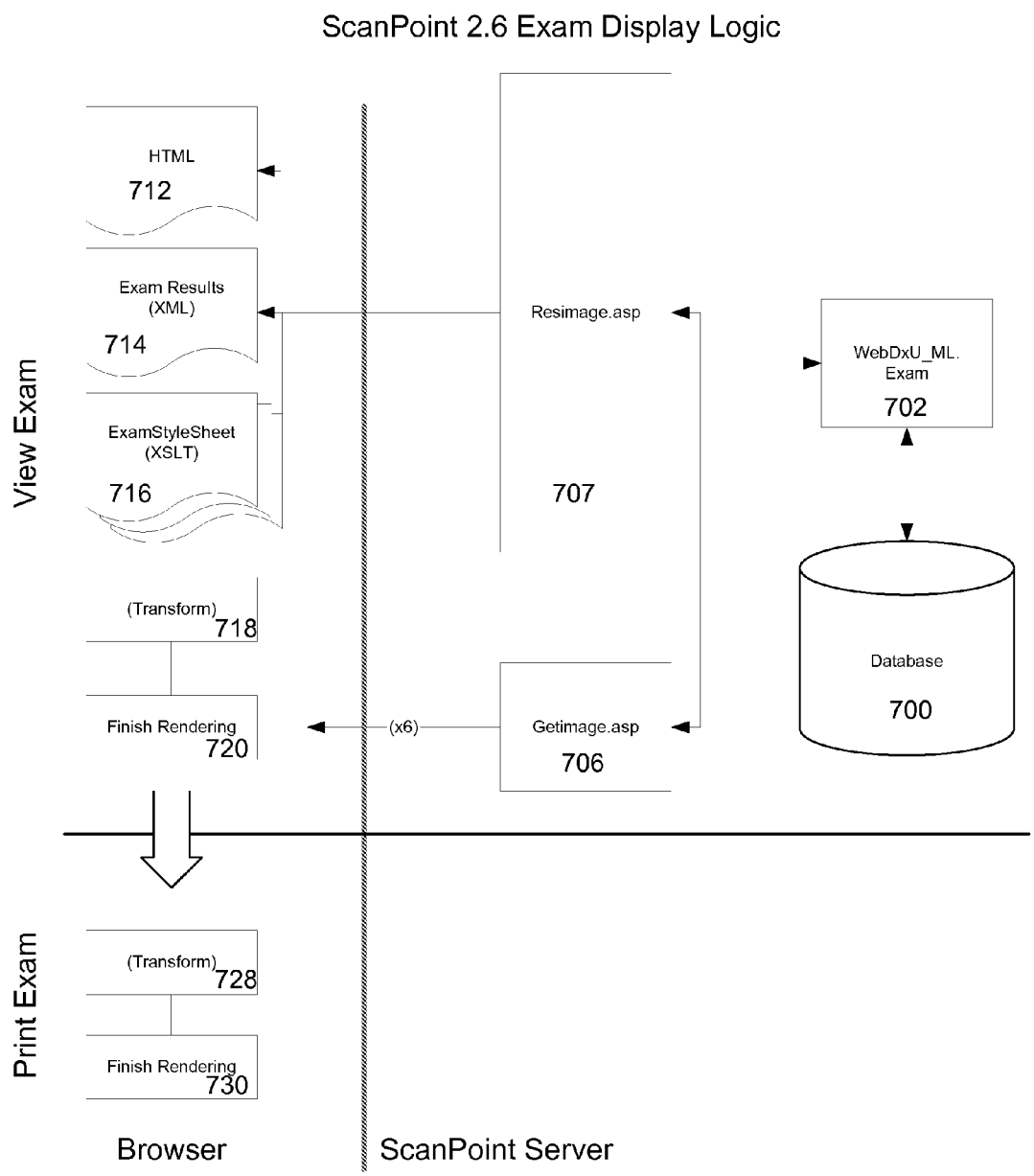
FIG. 62 is an alternative arrangement of the Display Logic Flowchart of the Internet System.

FIG. 62 is an alternative arrangement of the Exam Logic Flowchart for the Internet System. As shown in the figure, this is for the ScanPoint version 2.6. There are two major sections, a view exam section and a print exam section that is cross-referenced with a ScanPoint server column. The print exam is simplified to include only Transform the 728 and Finishing Rendering 730 processing blocks. The view exams and the prints exams use the same part of a ScanPoint display logic flowchart both used in ScanPoint version 2.5.0.10, except that a Resimage.asp 707 in version 2.6 relates directly to the Exam Results XML 714. Further explanations are provided in FIG. 66 below.

Figure 63:
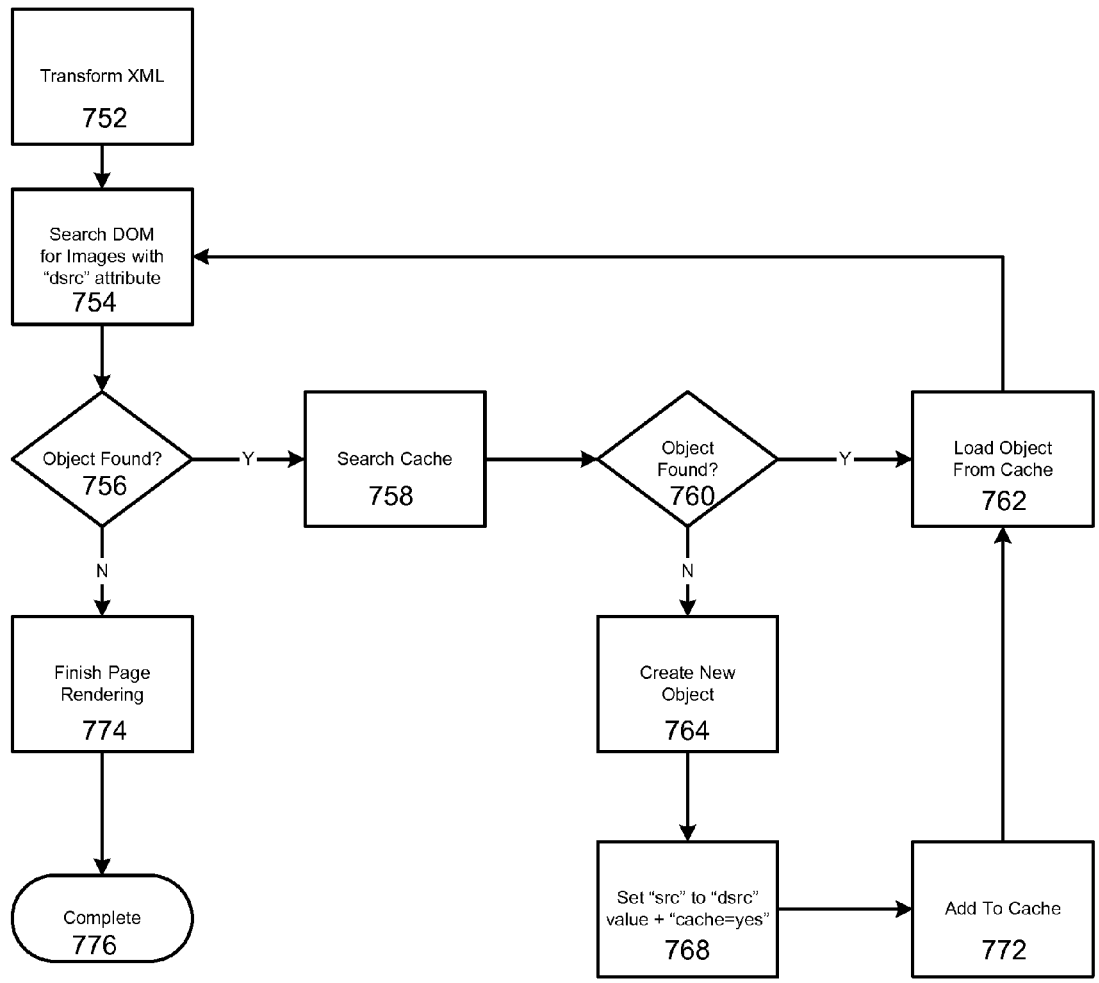
FIG. 63 is another algorithm of the Internet System.

FIG. 63 is another algorithm of the Internet System that concerns the architectural approach for the sonographer measurement edit feature. Implementation of a manual thickness measurement requirements in the ScanPoint software as generally described in FIG. 49 preferably requires a substantial amount of interaction between the analysis objects performed in the initial bladder wall mass algorithms as previously described vectors between the enduser who is reviewing the results and the sonographer who also reviews and edits the results. FIG. 61 describes in flowchart format the display logic required to place multiple asp pages and generates multiple XSLT documents. The Exam Results subsystem provides for a generic usable framework for displaying exam results, allows for a single page break logic with page headers as required, enables the manual thickness measurement requirements for the transceiver 10 and its particular embodiments as previously described, and allows for the custom collection of data from users that view the exam results. The architecture can be broken into multiple categories, one category concerns XSLT files which are stored in site-user/xml and site-admin/xml locations and also includes the attribute "Trans" to any element. The templates generate XHTML-HTML documents conforming to the XML specification, such XML specification having advantages that no adverse impact on the display of the data. The "Trans" element, very simply, identifies the node as containing text that must be localized into the user's language. Very simply identifies the node as containing text that must be localized into the user's language. The XSLT files are not necessarily referenced from the ASP pages, but may be retrieved by invoking the WebDx-U_ML.Exam method "GetTranslatedXSL" command. The command file is located and read into the MSXML DOM domain that serves to localize the text of all the nodes with the "Trans" attribute. Thereafter, it allows localized template to be returned to the requestor/user. The software used in implementing FIG. 74 has an image cache mechanism that is invoked immediately after a document is transformed. A cacheable image is one that has a node name of "ing" and contains an attribute with a name of "DSRC". This node does not have a "SRC" attribute. These attributes searches the browser document object model (DOM) for all the "ing" elements containing the "dsrc" attributes. For each node encountered, an attempt is made to find a matchable DSRC attribute in the image cache. If a match is found, then the SRC attribute will be set from the cache image object. If not found, then a new image object will be created, downloaded, and cached for future use. The algorithm begins with the process transformed XML in block 72 thereafter followed by a search domain for images with the DSRC attribute in block 74. From there, a decision diamond 756 is reached with the query object found. If "yes", then a searchable cache at block 758 is implemented. Upon implementing the searchable cache at block 758, a decision diamond 760 is encountered with the query object found. If "yes", then the object is noted as indicated in block 762, that is, the object is loaded from the cache in block 762. Thereafter, it returns to the search domain block 754 and the process is resumed. Returning to the decision diamond 756, if the answer is "no" to the query object found, then the block 774, the page is finished for vendor. Thereafter, the algorithm 74 is completed at terminal 776. Returning to the decision diamond 760, if the answer to the query object found is "no", then the block 764 is implemented for creating a new object. Once the new object is created, the next processing block is 768 and the SRC is set to a DSRC attribute and the value is set to a cache value of "yes". Thereafter, at block 772, the SRC and DSRCs are added to the cache and the process is returned to loan object from cache at block 762. The parameter of cache equal to "yes" causes the HGTP response headers to be set to allow a cache of five minutes instead of the usual default which is to "expire" immediately.

Figure 64:
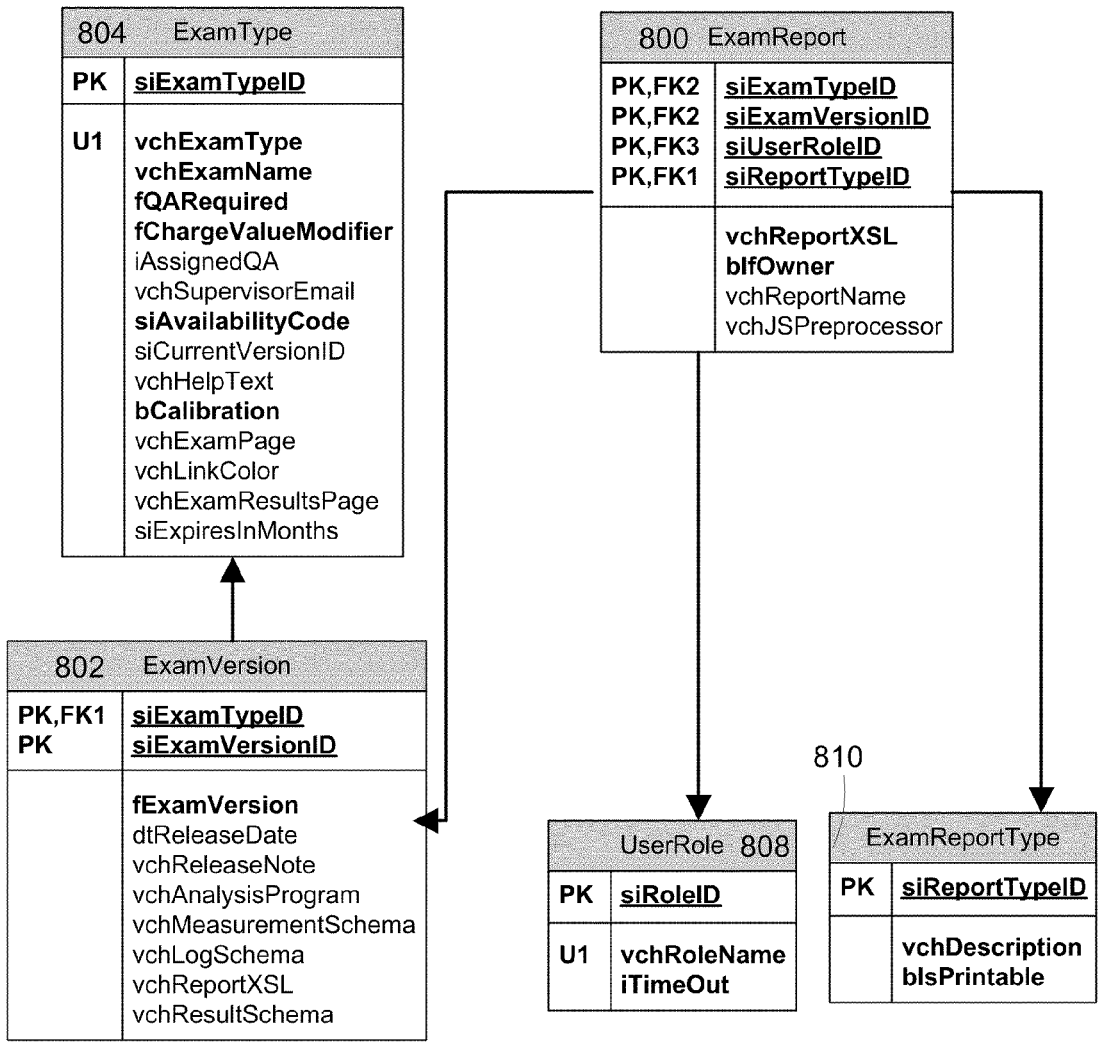
FIG. 64 is program flowchart for accessing the Internet System.

FIG. 64 represents an Image Cache Flowchart. An image cache mechanism is invoked during the transformation to XML(752). The browser will then search to match the image (754). The system will test to see if the object is found (756). If the object is found then the program will search again (758), then test to see if the image is found (760). If found it will load the object (763) and return to box 754. If the object is not found then in box 764 a new object will be created, the object will be assigned the correct properties, add to the cache (772) and load the object (762) and then execute box 754 again. If the an object is not found in box 756 then the system will finish rendering the page (774) and complete the program (776).

FIG. 64 is a database relationship map of the database 700 in the form of an entity relationship diagram (ERD) or a data flow diagram (DFD) having five tabular entities to describe how the data is formatted within the database 700 for the purposes of generating an exam report for bladder mass determination. The five tables include an Exam Report 800, an Exam Version 802, an Exam type 804, a User Role 808, and an Exam Report Type 810. Each table or tabular entity is further comprised of a number of fields or columns. In each table a unique field is designated as the primary key (PK). The PK allows the unique identification each row or record in the table. Furthermore, a table may also include a number of foreign keys (FK) from another tabular entity. The PK may also be listed in a tabular entity as a key pair (PK, $FK_n$) where n is a numerical value. For example, the table 800 has several primary key (PK)-foreign key (FK) pairs designated as PK- FK1, PK-FK2, and PK-FK3. PK-FK1 concerns the field siReportTypeID, which in turn is comprised of the PK from the examReport Type table 810. PK-FK2 concerns the field element siUserRoleID that in turn is comprised of PK in the User Role table 808.

The PK serves to define a uniquely searchable record within a given tabular entity. Adjacent to the PK-FK1-3 pairs are several fields. In order to build the exam report table 800 will be linked to four other database tables with the corresponding correct index or key code. Table 800 will link to: table 810 to generate the exam report type and table 808 to return the user role. Table 800 will link to table 802 to generate an Exam Version, this table has a sub table 804 that includes information on the exam type.

Figures 65, 66:
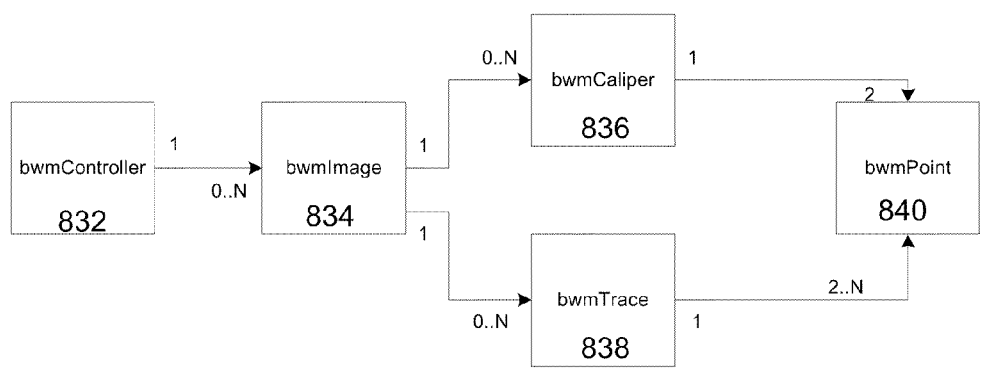
FIG. 65 is program menu for exams using the Internet System.
FIG. 66 is a program flowchart.

FIG. 65 is a program menu for exams using the Internet System. In particular, this is a software block for the clone exams 820 and includes a list of program subroutines that allows a sonographer to clone or replicate exams for subsequent modification. Included is table that contains an audit trail about any exam that is cloned in scanpoint FIG. 66 is a program flowchart for a java scripts objects with cardinality values. The flowchart begins with a block 832 having a bwmController that proceeds to a block 834 having a cardinal relationship from 0 to N, i.e., from a possibility of no relationships up to N relationships. Thereafter, there are two options that break from the bwmImage 834, a bwmCaliper 836 having a cardinal relationship from 0 to N, and a bwmTrace 838, also having a cardinal relationship from 0 to N. Thereafter, the bwmCaliper 836 has a cardinal relationship of 2 and the bwmTrace 838 having cardinal relationship from 2 to N. Both bwmCaliper 836 and bwmTrace 838 converge at a bwmPoint 840. The bwmController 832 object is responsible for parsing the browser domain after the page has been loaded to determine how to create the bwmImage objects. Every IMG element that contains the attribute of "editable" is within a value of "true" will result in a single bwmImage object created and stored by the bwmController. Once an IMG object that has been classified as "editable", it must contain a "trace" attribute or "lines" attribute, thus at objects block 838. The value of each of these attributes within the objects block 838 is the number allowed for that image. For example, if the lines are ="2" that would signify that the bwmImage object has two bwmMeasurement objects created. The bwmMeasurement object is a simple caliper tool as shown in block 836 and allows the user to select a start and end point and serves to measure the distance between the two points in pixels. If a value is specified denoting the scale of image in millimeters per pixel, the distance in millimeters will also be generated. The bwmTrace object allows 2 to N points to be selected; each point will be a node on a line. Once all the user actions have been completed, the bwmController object 832 allows the user to submit the results in XML format. Each object is capable of appending a node to an XML document object model (DOM) document containing its own results. The XML documents that are generated are modifiable with and identify the editable images. The block in FIG. 78 renders its own display to the user and is controlled by passing down nested DIV elements that are created for each object in turn.

Figure 67:
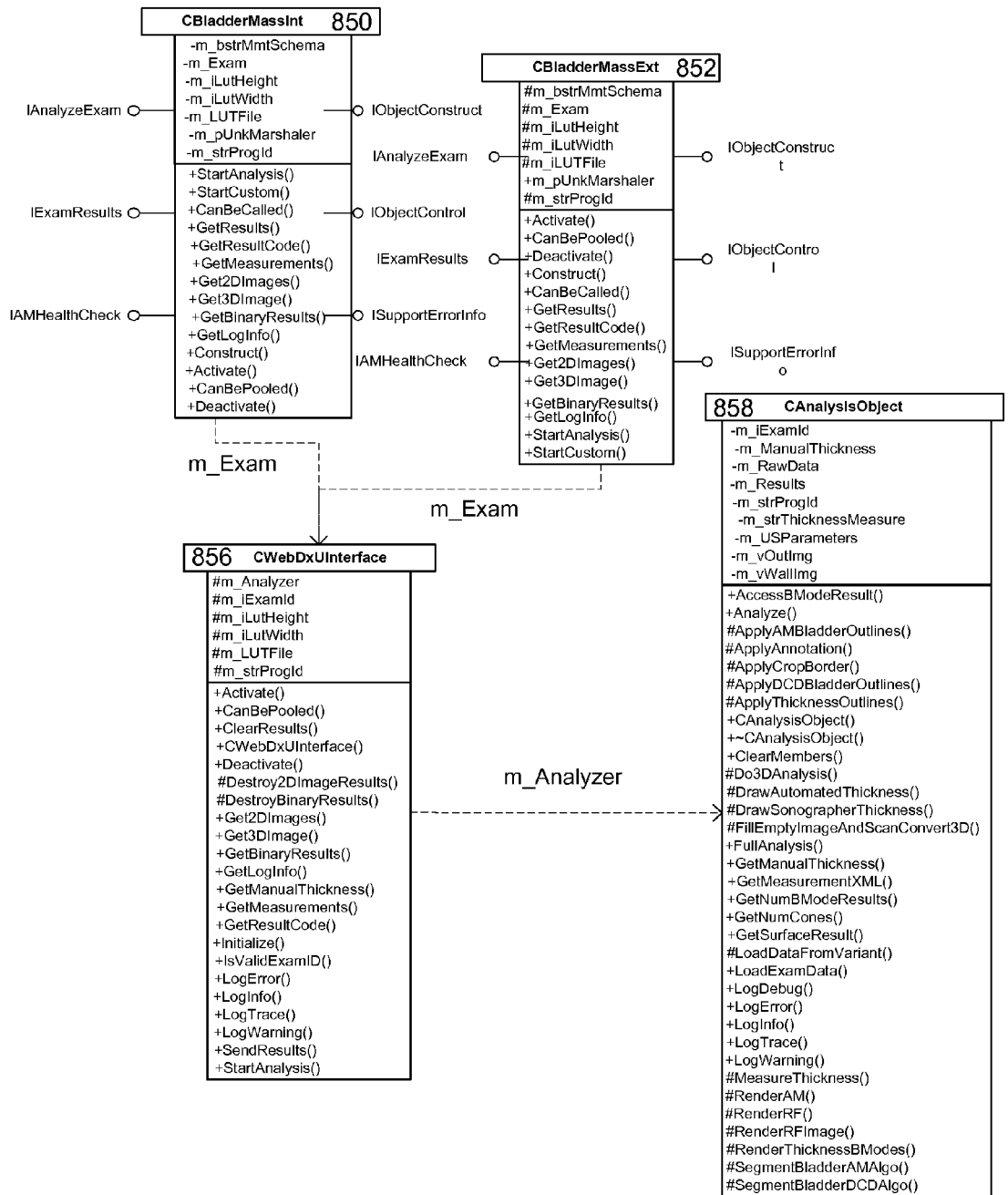
FIG. 67 is a flowchart of object listings for the Internet System.
Figure 68:
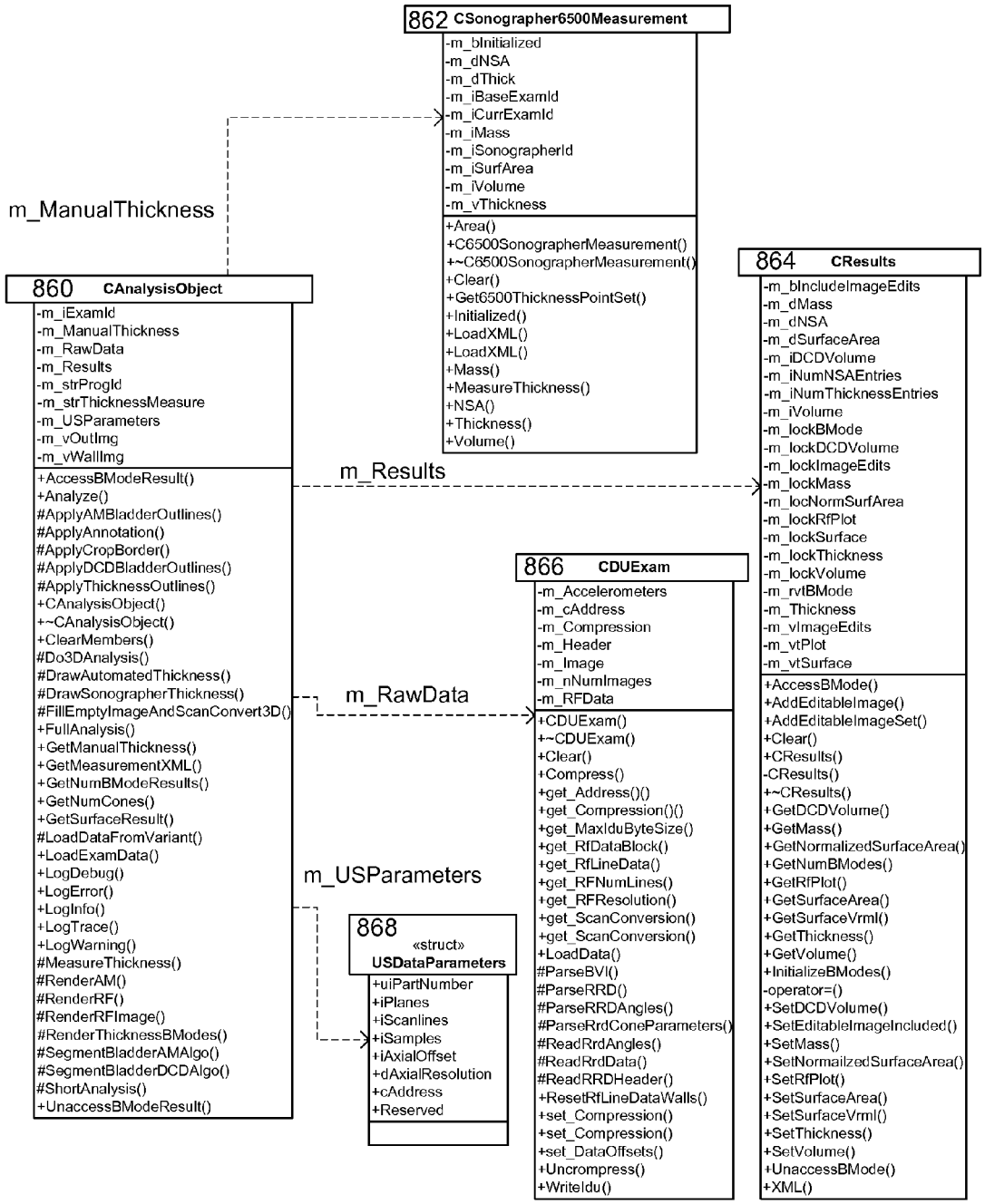
FIG. 68 is a flowchart of object listings for thickness determination using the Internet System.

FIG. 67 is a software object diagram for the Internet System analysis module 600D of the Scanware application. The software object diagram is comprised of object tables, each table having a data section and an interface function section. The tables include a CbladderMassint 850, a CbladderMassExt 852, a CwebDxuInterface 856, and a CanalyssisObject 858. Some of the object tables have interface entries in the data and interface function sections. The software object diagram illustrates how the analysis module performs the analyses of the algorithms of the particular embodiments. The software object diagram presents a collaboration of the COM interface classes and the main analysis object. Table 858 is an object that controls the collection and analysis of external data. The external analysis modules are found in table 850 and 852. Table 850 is used for the customer exam on the Scan point System. Table 852 is used for internal exams. Table 856 implements the data collection. Table 858 coordinates the analysis of the data. Table 858 performs the analysis, stores the results and provides those results to an interface. A set of classes which form the external interface of the analysis module specifically CBladderMassInt 850 and CBladderMassExt 852 supply the common object model (COM) interface implementations required for the Internet software of the ScanPoint method. The "Ext" class corresponds to the ScanPoint_AM.BladderMass interface implementation that is used for the enduser exam on the ScanPoint system. The "Int" class is used as measurement for the internal exam. The internal exam is identified with the ScanPoint_AM.BladderMassInternal progID FIG. 68 is a flowchart of object listings as a software object diagram for thickness determination using the Internet System. FIG. 68 is comprised for manual thickness of five major tables include a CAnalysisObject table 860, CSonographer 6500 measurement table 862, a CResults table 864, a CDXUExam table 8866, and a U.S. Data parameters 868 table. The flowchart of object listings illustrates a collaboration diagram between the analysis objects and helper objects used in the analysis as indicated by the direction of the arrows. The software object diagram is comprised of our object tables, each table having a data section and an interface function section.

Figure 69:
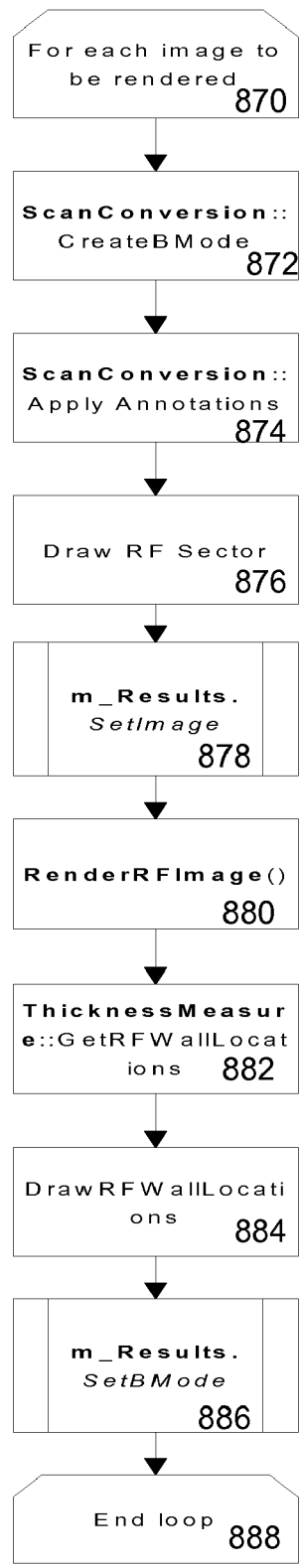
FIG. 69 is a B-mode algorithm using the Internet System.

FIG. 69 is a B-mode algorithm using the Internet System. The Internet algorithm includes opening at process 870 for each image to be rendered thereafter followed by a process 872 main scan conversion create B-mode thereafter followed by block 874 scan conversion apply annotations. After supplying annotations. the next processing block is 876 draw the radio frequency sector. In this block, the one-dimensional of the primary echo reflections are developed. Thereafter, at block 878 is a set image results block followed by a RenderRFImage block 880. Thereafter, there is a thickness measurement block 882 and a draw RF wall location block 884. Finally, there is a results set B-mode block 886 and an end loop block 888.

Figure 70:
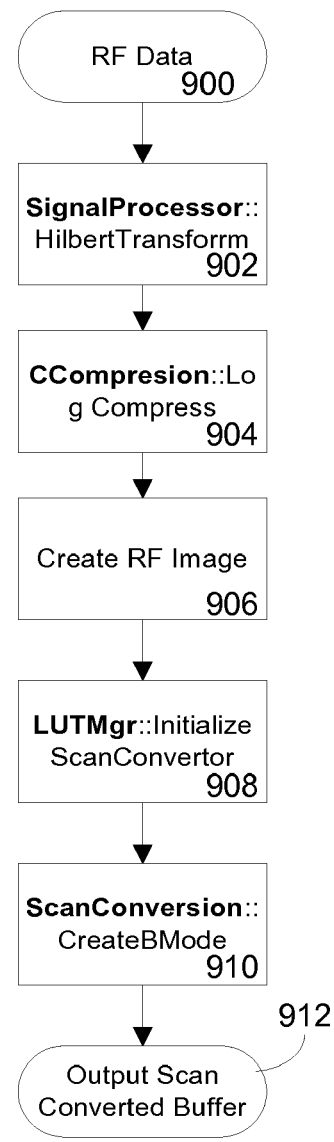
FIG. 70 is an A-mode algorithm using the Internet System.

FIG. 70 is an A-mode algorithm using the Internet System. FIG. 82 begins with entry of RF data at entry point 900. Thereafter, a process in block 902 for signal processor generate HilbertTransform. After doing a HilbertTransform, the data is compressed at block 904 with CCompression log Compress block. Once compressed, the next processing block is 906, which is referred to as Create RF Image. Thereafter, at block 908 is the LUTMgr Initialize ScanConverter processing block which in turn is followed by scan conversion create B-mode at block 910. Thereafter, the output scan is converted into buffer at terminus 912.

Accordingly, the scope of the invention is not limited by the disclosure of these preferred and alternate embodiments. Instead, the invention should be determined entirely by reference to the claims that follow.

What is claimed is:

1. A method to measure wall thickness of an organ using an ultrasound transceiver, the method comprising:
   positioning an ultrasound transceiver exterior to a patient such that at least a portion of an organ wall is within the range of the transceiver;

transmitting ultrasound pulses as scanlines to, and receiving those pulses echoed back from, the external and internal surface of the portion of the organ wall, and based on those pulses, forming at least one two-dimensional image;

selecting wall loci from the scanlines to define a first position of the organ wall crossing the scanlines from the two dimensional image;

adjusting the position of the wall loci by applying a one-dimensional analysis of the pulse echoes associated with the two-dimensional image to a second position and a third position of the organ wall by converting signals of ultrasound echoes associated with the scanlines of the two-dimensional image from a non-rectified signal pattern to a rectified signal pattern is achieved by a Hubert Transform; and determining the thickness of the organ wall by calculating the difference of the wall loci between the second and third positions crossing the scanlines of the two dimensional image, wherein peak maxima of the rectified signal pattern of each scanline of the two-dimensional image determines wall loci candidates for the second and third positions.

2. The method of claim 1, wherein a portion of the rectified signal pattern is analyzed to determine a nearest second position candidate.

3. The method of claim 2, wherein the nearest second position candidate is determined by vector analysis of each scanline's peak maxima.

4. The method of claim 3, wherein a nearest second position locus within each scanline is confirmed by candidate point cost analysis of the nearest second position locus of each scanline rectified signal pattern and the nearest second position locus of neighboring scanline rectified signal patterns.

5. The method of claim 3, wherein thickness is calculated as a difference between the nearest third position candidate and the nearest second position candidate.

6. The method of claim 1, wherein the portion of the rectified signal pattern is analyzed to determine a nearest third position candidate.

7. The method of claim 6, wherein the nearest third position candidate is determined by vector analysis of each scanline's peak maxima.

8. The method of claim 6, wherein a nearest third position locus within each scanline is confirmed by candidate point cost analysis of the nearest second position locus of each scanline rectified signal pattern and the nearest third position locus of neighboring scanline rectified signal patterns.

* * * * *